US012150642B2

(12) United States Patent
Coleman

(10) Patent No.: US 12,150,642 B2
(45) Date of Patent: Nov. 26, 2024

(54) SUTURE SLEEVE PATCH AND METHODS OF DELIVERY WITHIN AN EXISTING ARTHROSCOPIC WORKFLOW

(71) Applicant: New York Society for the Relief of the Ruptured and Crippled, Maintaining the Hospital for Special Surgery, New York, NY (US)

(72) Inventor: Struan H. Coleman, New York, NY (US)

(73) Assignee: New York Society for the Relief of the Ruptured and Crippled, Maintaining the Hospital for Special Surgery, New York, NY (US)

( * ) Notice: Subject to any disclaimer, the term of this patent is extended or adjusted under 35 U.S.C. 154(b) by 806 days.

(21) Appl. No.: 17/086,272

(22) Filed: Oct. 30, 2020

(65) Prior Publication Data
US 2021/0045734 A1   Feb. 18, 2021

Related U.S. Application Data

(63) Continuation of application No. 16/352,721, filed on Mar. 13, 2019, now Pat. No. 11,375,996, which is a
(Continued)

(51) Int. Cl.
*A61B 17/04*     (2006.01)
*A61B 17/00*     (2006.01)
(Continued)

(52) U.S. Cl.
CPC .......... *A61B 17/0482* (2013.01); *A61B 17/00* (2013.01); *A61B 17/04* (2013.01);
(Continued)

(58) Field of Classification Search
CPC ..... A61B 17/0482; A61B 17/00; A61B 17/04; A61B 17/84; A61B 17/0466;
(Continued)

(56) References Cited

U.S. PATENT DOCUMENTS 4,034,850 A   7/1977 Mandel et al.
4,092,739 A   6/1978 Clemens et al.
(Continued)

FOREIGN PATENT DOCUMENTS

AU   2015308795 A1   4/2017
BR   PI0814523 B1    2/2015
(Continued)

OTHER PUBLICATIONS

Gammage et al.; Experience with a lead fixation/suture sleeve; Pacing and Clinical Electrophysiology: 21(3); pp. 549-552; Mar. 1, 1998.
(Continued)

*Primary Examiner* — Erich G Herbermann
(74) *Attorney, Agent, or Firm* — Shay Glenn LLP

(57) ABSTRACT

Suture delivered patches adapted for interposition, augmentation or repair devices for use in tendon and ligament repair, including rotator cuff repair, have been developed as well as methods for their delivery using suture guided arthroscopic methods. The repair patches may be provided from suitable biocompatible materials. The patches may be delivered using anchored sutures already in use during a surgical repair including, open, minimally invasive, endoscopic, and arthroscopic repair procedures. Additionally, fixation of the suture delivered repair patch is secured along with the normal suture securing workflow of the one or more sutures used to deliver the patch.

25 Claims, 51 Drawing Sheets

Related U.S. Application Data continuation of application No. 15/339,782, filed on Oct. 31, 2016, now Pat. No. 10,675,016.

(60) Provisional application No. 62/248,346, filed on Oct. 30, 2015.

(51) Int. Cl.
*A61B 17/84* (2006.01)
*A61F 2/00* (2006.01)
*A61F 2/08* (2006.01)
*A61F 13/01* (2024.01)

(52) U.S. Cl.
CPC ............ *A61B 17/84* (2013.01); *A61F 2/0063* (2013.01); *A61F 2/08* (2013.01); *A61F 13/01008* (2024.01); *A61B 2017/00004* (2013.01); *A61B 2017/0414* (2013.01); *A61B 2017/044* (2013.01); *A61B 2017/0453* (2013.01); *A61B 17/0466* (2013.01); *A61B 2017/0495* (2013.01); *A61F 2002/0072* (2013.01); *A61F 2/0811* (2013.01); *A61F 2002/0829* (2013.01); *A61F 2002/0864* (2013.01); *A61F 2002/0888* (2013.01); *A61F 2210/0076* (2013.01)

(58) Field of Classification Search
CPC .. A61B 2017/00004; A61B 2017/0414; A61B 2017/044; A61B 2017/0453; A61B 2017/0495; A61F 2/0063; A61F 2/08; A61F 2/0811; A61F 13/00008; A61F 2002/0072; A61F 2002/0829; A61F 2002/0864; A61F 2002/0888; A61F 2210/0076
See application file for complete search history.

(56) References Cited

U.S. PATENT DOCUMENTS

| | | | |
|---|---|---|---|
| 4,164,046 A | 8/1979 | Cooley |
| 4,454,875 A | 6/1984 | Pratt et al. |
| 4,516,584 A | 5/1985 | Garcia |
| 4,549,545 A | 10/1985 | Levy |
| 4,585,458 A | 4/1986 | Kurland |
| 4,723,540 A | 2/1988 | Gilmer |
| 4,932,960 A | 6/1990 | Green et al. |
| 5,116,357 A | 5/1992 | Eberbach |
| 5,122,155 A | 6/1992 | Eberbach |
| 5,209,756 A | 5/1993 | Seedhom et al. |
| 5,290,217 A | 3/1994 | Campos |
| 5,336,616 A | 8/1994 | Livesey et al. |
| 5,366,460 A | 11/1994 | Eberbach |
| 5,366,480 A | 11/1994 | Corriveau et al. |
| 5,370,650 A | 12/1994 | Tovey et al. |
| 5,374,268 A | 12/1994 | Sander |
| 5,383,904 A | 1/1995 | Totakura et al. |
| 5,397,352 A | 3/1995 | Burres |
| 5,405,360 A | 4/1995 | Tovey |
| 5,425,766 A | 6/1995 | Bowald |
| 5,500,000 A | 3/1996 | Feagin et al. |
| 5,503,638 A | 4/1996 | Cooper et al. |
| 5,582,288 A | 12/1996 | Zatarga |
| 5,645,568 A | 7/1997 | Chervitz et al. |
| 5,658,313 A | 8/1997 | That |
| 5,713,374 A | 2/1998 | Pachence et al. |
| 5,733,308 A | 3/1998 | Daugherty et al. |
| 5,961,521 A | 10/1999 | Roger |
| 6,010,525 A | 1/2000 | Bonutti et al. |
| 6,059,818 A | 5/2000 | Johnson et al. |
| 6,080,192 A | 6/2000 | Demopulos et al. |
| 6,152,949 A | 11/2000 | Bonutti |
| 6,171,318 B1 | 1/2001 | Kugel et al. |
| 6,245,081 B1 | 6/2001 | Bowman et al. |
| 6,511,498 B1 | 1/2003 | Furnex |
| 6,514,274 B1 | 2/2003 | Boucher et al. |
| 6,645,211 B2 * | 11/2003 | Magana ............... A61B 17/842 606/279 |
| 7,078,615 B2 | 7/2006 | Gladfelter et al. |
| 7,082,337 B2 | 7/2006 | Sommer et al. |
| 7,303,577 B1 | 12/2007 | Dean |
| 7,357,810 B2 | 4/2008 | Koyfman et al. |
| 7,559,937 B2 | 7/2009 | de la Torre et al. |
| 7,601,165 B2 | 10/2009 | Stone |
| 7,608,098 B1 | 10/2009 | Stone et al. |
| 7,658,751 B2 | 2/2010 | Stone et al. |
| 7,749,250 B2 | 7/2010 | Stone et al. |
| 7,857,830 B2 | 12/2010 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 8,016,883 B2 | 9/2011 | Coleman et al. |
| 8,080,260 B2 | 12/2011 | Derwin et al. |
| 8,088,130 B2 | 1/2012 | Kaiser et al. |
| 8,118,836 B2 | 2/2012 | Denham et al. |
| 8,128,658 B2 | 3/2012 | Kaiser et al. |
| 8,133,501 B2 | 3/2012 | Li et al. |
| 8,137,381 B2 | 3/2012 | Foerster et al. |
| 8,137,382 B2 | 3/2012 | Denham et al. |
| 8,226,715 B2 | 7/2012 | Hwang et al. |
| 8,231,653 B2 | 7/2012 | Dreyfuss |
| 8,251,998 B2 | 8/2012 | Hoeppner et al. |
| 8,277,458 B2 | 10/2012 | Schneider |
| 8,303,604 B2 | 11/2012 | Stone et al. |
| 8,317,825 B2 | 11/2012 | Stone |
| 8,361,113 B2 | 1/2013 | Stone et al. |
| 8,562,645 B2 | 10/2013 | Stone et al. |
| 8,574,235 B2 | 11/2013 | Stone |
| 8,585,773 B1 | 11/2013 | Kucklick |
| 8,597,327 B2 | 12/2013 | Stone et al. |
| 8,649,881 B2 | 2/2014 | Helgesson |
| 8,652,171 B2 | 2/2014 | Stone et al. |
| 8,652,172 B2 | 2/2014 | Denham et al. |
| 8,672,969 B2 | 3/2014 | Stone et al. |
| 8,721,684 B2 | 5/2014 | Denham et al. |
| 8,771,316 B2 | 7/2014 | Denham et al. |
| 8,834,521 B2 | 9/2014 | Pinto et al. |
| 8,876,864 B2 | 11/2014 | Spedden et al. |
| 8,932,331 B2 | 1/2015 | Kaiser et al. |
| 8,936,621 B2 | 1/2015 | Denham et al. |
| 8,968,364 B2 | 3/2015 | Berelsman et al. |
| 8,986,378 B2 | 3/2015 | Koob |
| 8,998,949 B2 | 4/2015 | Stone et al. |
| 9,005,250 B2 | 4/2015 | Evans |
| 9,005,287 B2 | 4/2015 | Stone |
| 9,017,381 B2 | 4/2015 | Kaiser et al. |
| 9,078,644 B2 | 7/2015 | Stone |
| 9,149,267 B2 | 10/2015 | Norton et al. |
| 9,173,647 B2 | 11/2015 | Bonutti et al. |
| 9,192,365 B2 | 11/2015 | Roshanall et al. |
| 9,271,713 B2 | 3/2016 | Denham et al. |
| 9,339,369 B2 | 5/2016 | McQuillan et al. |
| 9,381,013 B2 | 7/2016 | Norton |
| 9,463,012 B2 | 10/2016 | Bonutti et al. |
| 9,468,433 B2 | 10/2016 | Denham et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,642,661 B2 | 5/2017 | Stone et al. |
| 9,763,656 B2 | 9/2017 | Stone et al. |
| 9,801,978 B2 | 10/2017 | Paulos et al. |
| 9,918,826 B2 | 3/2018 | Bereisman et al. |
| 9,918,827 B2 | 3/2018 | Berelsman et al. |
| 10,028,814 B2 | 7/2018 | Levin et al. |
| 10,076,543 B2 | 9/2018 | Wilhelmi et al. |
| 10,092,288 B2 | 10/2018 | Denham et al. |
| 10,159,722 B2 | 12/2018 | Sun et al. |
| 10,172,607 B2 | 1/2019 | Burkhart |
| 10,172,703 B2 | 1/2019 | Adams et al. |
| 10,265,155 B2 | 4/2019 | Lu et al. |
| 10,286,119 B2 | 5/2019 | Badylak et al. |
| 10,314,688 B2 | 6/2019 | Shepard et al. |
| 10,321,998 B2 * | 6/2019 | Rafiee .................. A61F 2/2418 |

(56) References Cited

U.S. PATENT DOCUMENTS

| | | |
|---|---|---|
| 10,350,049 B2 | 7/2019 | Morse et al. |
| 10,376,259 B2 | 8/2019 | Bonutti et al. |
| 10,675,016 B2 | 6/2020 | Coleman |
| 10,765,423 B2 | 9/2020 | Coleman |
| 10,835,235 B2 | 11/2020 | Coleman |
| 2001/0053913 A1 | 12/2001 | Freedland |
| 2002/0133236 A1 | 9/2002 | Rousseau |
| 2003/0023316 A1* | 1/2003 | Brown ............ A61L 27/40 623/23.72 |
| 2003/0032961 A1 | 2/2003 | Pelo et al. |
| 2003/0105519 A1 | 6/2003 | Fasol et al. |
| 2003/0130694 A1 | 7/2003 | Bojarski et al. |
| 2004/0048796 A1 | 3/2004 | Hariri et al. |
| 2004/0116963 A1 | 6/2004 | Lattouf |
| 2004/0146546 A1* | 7/2004 | Gravett ............ A61P 43/00 424/445 |
| 2004/0162580 A1 | 8/2004 | Hain |
| 2005/0192599 A1 | 9/2005 | Demarais et al. |
| 2005/0209705 A1 | 9/2005 | Niederauer et al. |
| 2005/0228448 A1 | 10/2005 | Li |
| 2005/0256532 A1 | 11/2005 | Nayak et al. |
| 2006/0029633 A1 | 2/2006 | Kaiser et al. |
| 2006/0089646 A1 | 4/2006 | Bonutti |
| 2006/0149266 A1 | 7/2006 | Cordasco |
| 2006/0190042 A1 | 8/2006 | Stone et al. |
| 2006/0286144 A1 | 12/2006 | Yang et al. |
| 2007/0088391 A1 | 4/2007 | McAlexander et al. |
| 2007/0123984 A1 | 5/2007 | Hodorek |
| 2007/0185506 A1 | 8/2007 | Jackson |
| 2007/0185532 A1 | 8/2007 | Stone et al. |
| 2007/0191849 A1 | 8/2007 | ElAttrache et al. |
| 2007/0288023 A1 | 12/2007 | Pellegrino et al. |
| 2008/0027470 A1 | 1/2008 | Hart et al. |
| 2008/0065114 A1 | 3/2008 | Stone et al. |
| 2008/0082121 A1 | 4/2008 | Chu |
| 2008/0125779 A1 | 5/2008 | Ferree |
| 2008/0167519 A1 | 7/2008 | St-Germain |
| 2008/0188874 A1 | 8/2008 | Henderson |
| 2008/0188933 A1 | 8/2008 | Koob et al. |
| 2008/0188936 A1 | 8/2008 | Ball et al. |
| 2008/0195151 A1 | 8/2008 | Ferree |
| 2008/0228271 A1 | 9/2008 | Stone et al. |
| 2008/0281422 A1 | 11/2008 | Schmieding |
| 2008/0294256 A1 | 11/2008 | Hagan et al. |
| 2009/0018655 A1 | 1/2009 | Brunelle et al. |
| 2009/0036893 A1 | 2/2009 | Kartalian et al. |
| 2009/0156986 A1 | 6/2009 | Trenhaile |
| 2009/0222039 A1 | 9/2009 | Dreyfuss et al. |
| 2009/0306711 A1 | 12/2009 | Stone et al. |
| 2010/0106194 A1 | 4/2010 | Bonutti et al. |
| 2010/0121337 A1 | 5/2010 | Pandya |
| 2010/0185219 A1 | 7/2010 | Gertzman et al. |
| 2010/0204775 A1 | 8/2010 | Edwin |
| 2010/0249834 A1 | 9/2010 | Dreyfuss |
| 2010/0262184 A1 | 10/2010 | Dreyfuss |
| 2010/0312357 A1 | 12/2010 | Levin et al. |
| 2011/0040311 A1 | 2/2011 | Levin et al. |
| 2011/0082479 A1 | 4/2011 | Friedlander |
| 2011/0091515 A1 | 4/2011 | Zilberman et al. |
| 2011/0184441 A1 | 7/2011 | St-Germain |
| 2012/0095470 A1 | 4/2012 | Kaiser et al. |
| 2012/0189707 A1 | 7/2012 | Chun et al. |
| 2012/0209401 A1 | 8/2012 | Euteneuer et al. |
| 2012/0259347 A1 | 10/2012 | Zaina et al. |
| 2012/0265219 A1 | 10/2012 | Rushdy et al. |
| 2012/0283831 A1 | 11/2012 | Murray |
| 2012/0330354 A1 | 12/2012 | Kane et al. |
| 2013/0004651 A1 | 1/2013 | Fu-Giles |
| 2013/0018395 A1 | 1/2013 | Friedlander et al. |
| 2013/0066343 A1 | 3/2013 | Park et al. |
| 2013/0066370 A1 | 3/2013 | Spedden et al. |
| 2013/0165972 A1 | 6/2013 | Sullivan |
| 2013/0178898 A1 | 7/2013 | Arnett et al. |
| 2013/0317545 A1 | 11/2013 | Gross et al. |
| 2013/0345749 A1 | 12/2013 | Sullivan et al. |
| 2014/0039503 A1 | 2/2014 | Pilgeram |
| 2014/0107675 A1 | 4/2014 | Hansen |
| 2014/0128664 A1 | 5/2014 | Ogdahl et al. |
| 2014/0155938 A1 | 6/2014 | Anderson |
| 2014/0243891 A1 | 8/2014 | Schmieding et al. |
| 2014/0277449 A1 | 9/2014 | Jones |
| 2014/0309691 A1 | 10/2014 | Brown et al. |
| 2015/0025552 A1 | 1/2015 | Stoll |
| 2015/0164498 A1 | 6/2015 | Dreyfuss et al. |
| 2015/0230913 A1* | 8/2015 | Derwin ............ A61L 27/3633 623/23.72 |
| 2015/0352257 A1 | 12/2015 | Early |
| 2017/0215864 A1 | 8/2017 | Sengun et al. |
| 2017/0215865 A1 | 8/2017 | Sengun et al. |
| 2017/0216015 A1 | 8/2017 | Sengun et al. |
| 2017/0216016 A1* | 8/2017 | Sengun ............ A61B 17/0483 |
| 2017/0273680 A1 | 9/2017 | Sengun et al. |
| 2017/0360425 A1 | 12/2017 | Stone et al. |
| 2018/0228596 A1 | 8/2018 | Wyland |
| 2018/0311411 A9 | 11/2018 | Derwin et al. |
| 2019/0015548 A1 | 1/2019 | Harrell |
| 2019/0038395 A1 | 2/2019 | Van Kampen |
| 2019/0134269 A1 | 5/2019 | Murray et al. |
| 2019/0274675 A1 | 9/2019 | Coleman |
| 2021/0068814 A1 | 3/2021 | Coleman |

FOREIGN PATENT DOCUMENTS

| | | |
|---|---|---|
| EP | 2389204 A1 | 11/2011 |
| EP | 2590691 A1 | 5/2013 |
| EP | 2700309 A1 | 2/2014 |
| EP | 2968646 A1 | 1/2016 |
| WO | WO2013/054216 A1 | 4/2013 |
| WO | WO2014/151766 A1 | 9/2014 |

OTHER PUBLICATIONS

Singh et al.; Nanoparticle-based-targeted drug delivery; Experimental and Molecular Pathology; 86(3); pp. 215-223; (Author Manuscript; 17 pgs.); Jun. 30, 2009.

\* cited by examiner

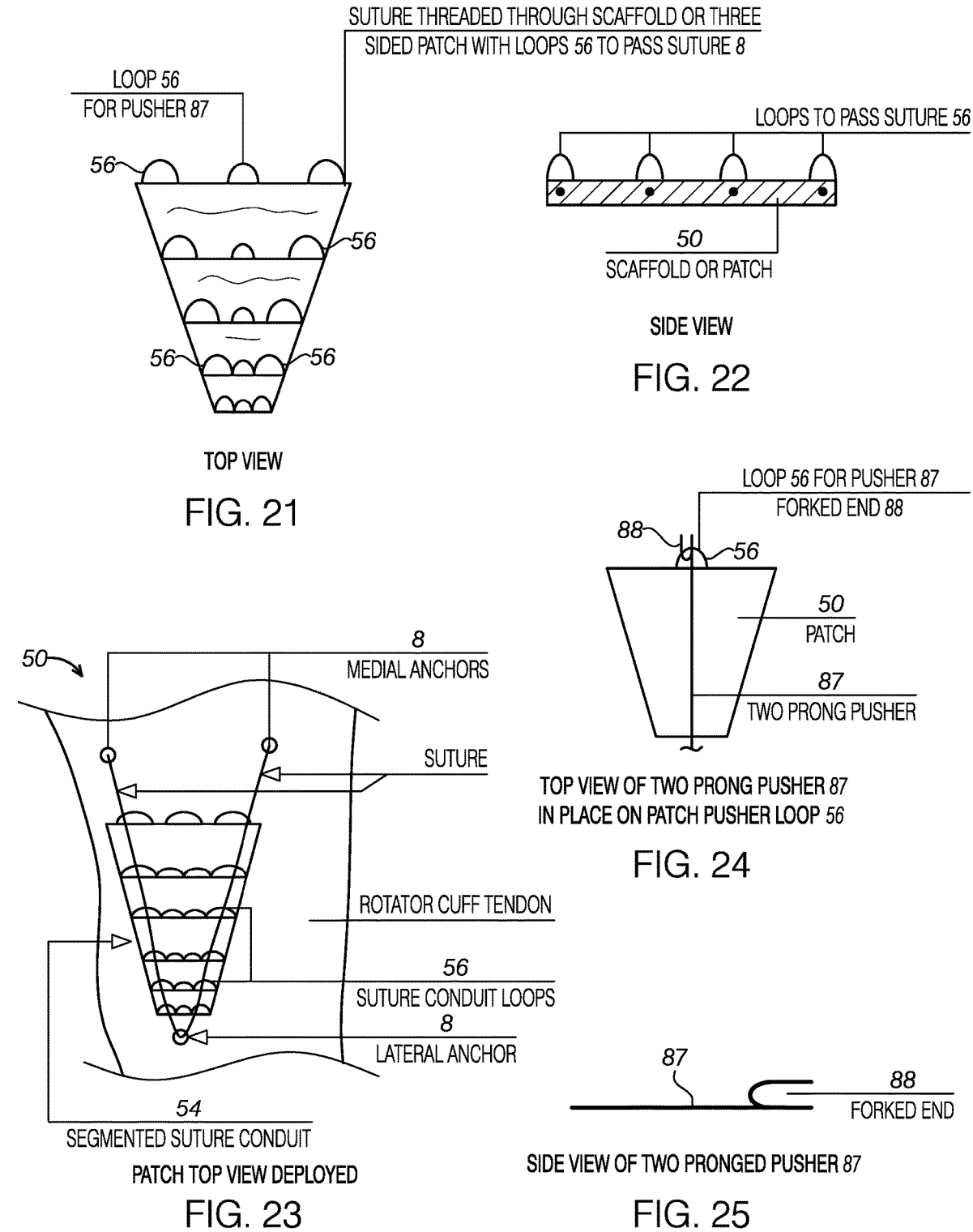

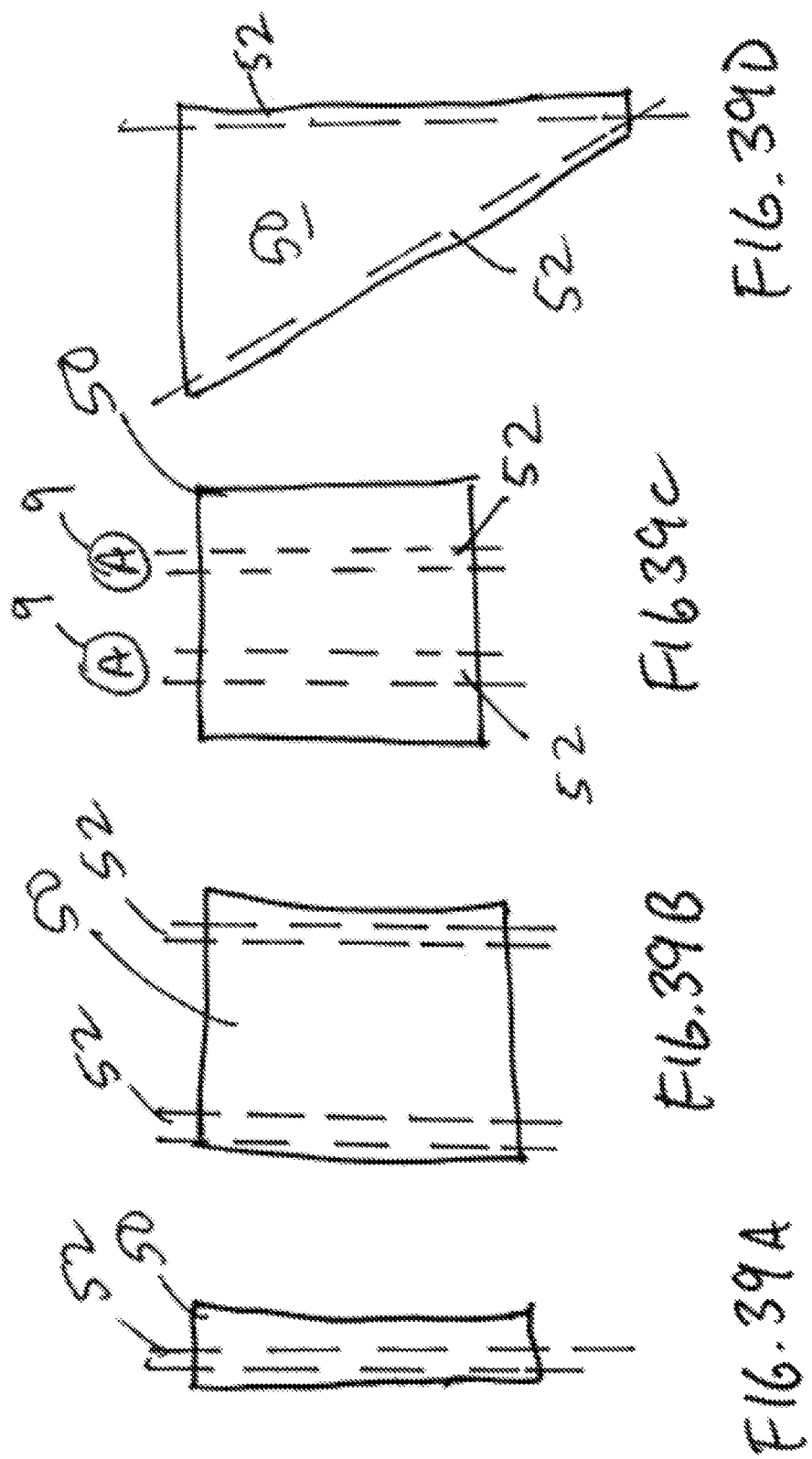

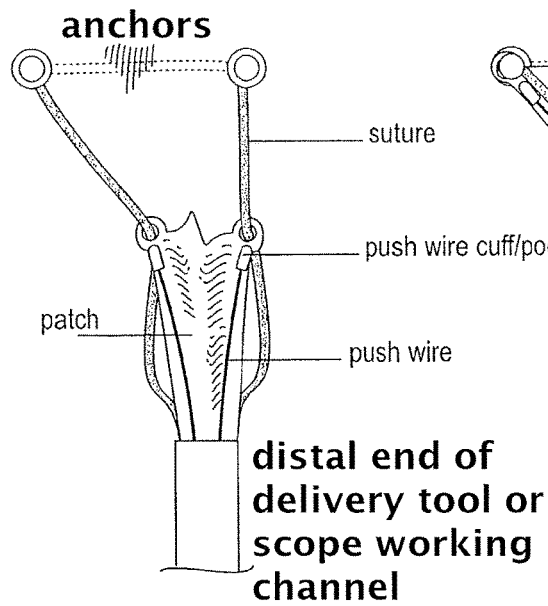
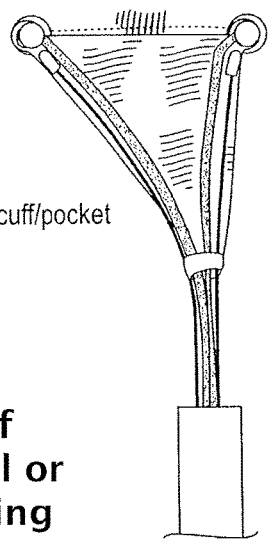
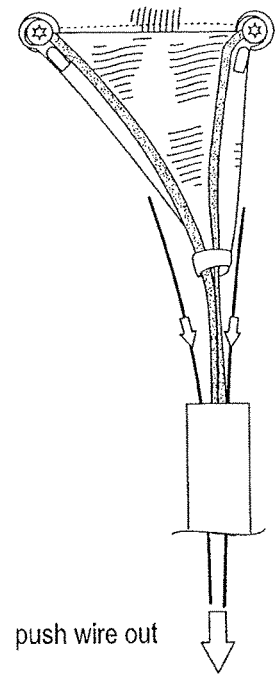
FIG. 53A
FIG. 53B
FIG. 53C
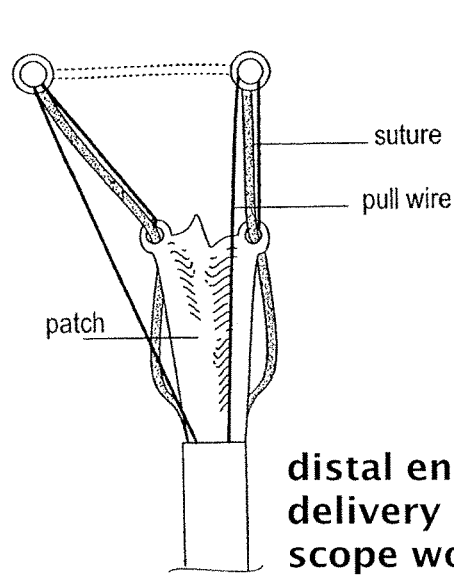
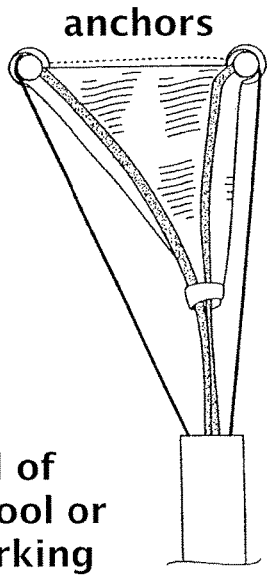
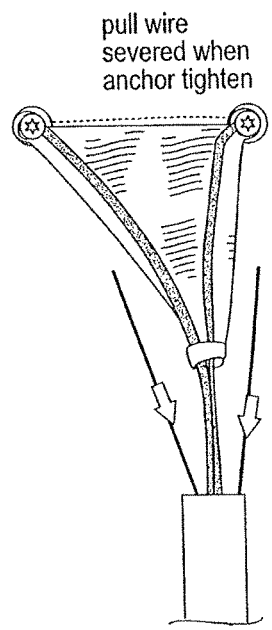
FIG. 54A
FIG. 54B
FIG. 54C

TIP MAY BE USED TO POSITION OR ADJUST PATCH

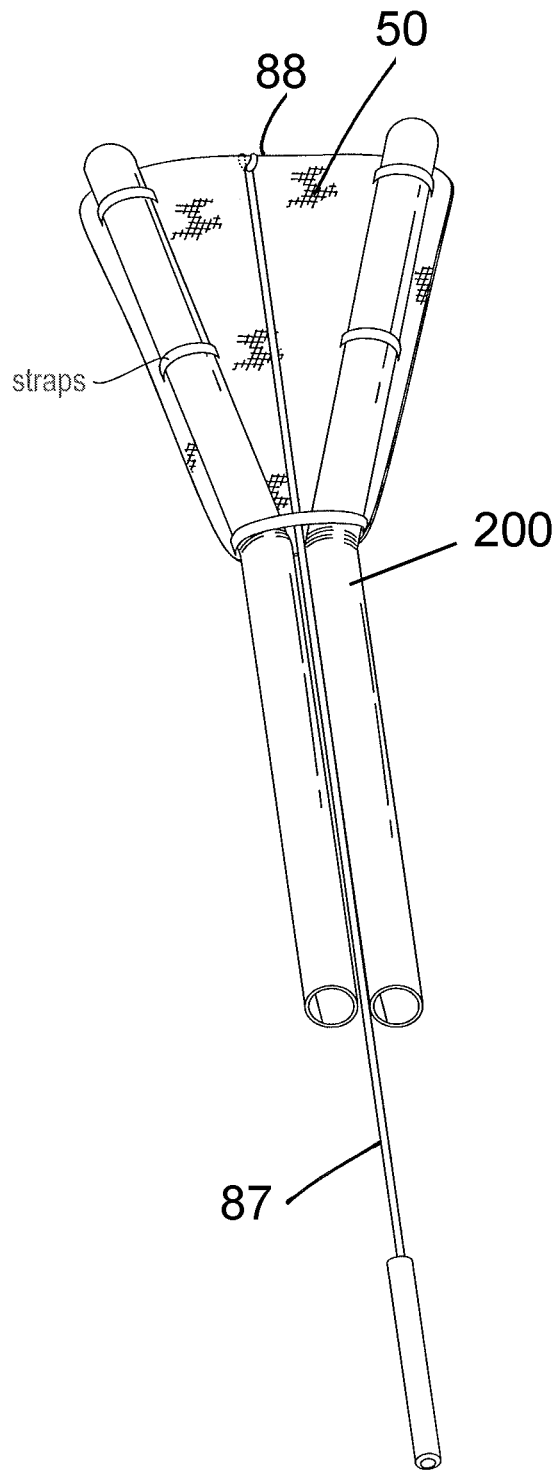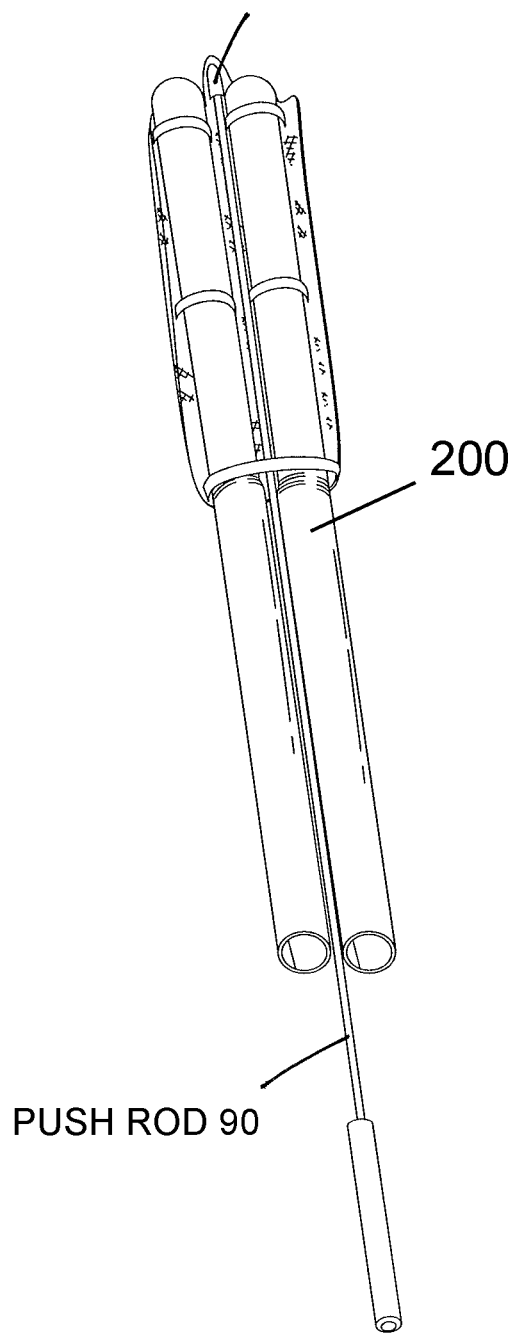
FIG. 66
FIG. 67

6800

```
┌─────────────────────────────────────────────────┐
│ Placing one or more suture anchors at a surgical site │ — 6805
└─────────────────────────────────────────────────┘
                         │
                         ▼
┌─────────────────────────────────────────────────────────────┐
│ Performing one or more steps of a suture repair procedure as needed │ — 6810
│   before placement of a suture guided patch at the surgical site    │
└─────────────────────────────────────────────────────────────┘
                         │
                         ▼
┌─────────────────────────────────────────────────┐
│ Inserting a suture used in the suture repair procedure │ — 6815
│    through a suture conduit of the suture guided patch │
└─────────────────────────────────────────────────┘
                         │
                         ▼
┌─────────────────────────────────────┐
│   Advancing the patch along the suture   │ — 6820
└─────────────────────────────────────┘
                         │
                         ▼
┌─────────────────────────────────────────────┐
│  Securing the patch in the surgical site with the suture  │ — 6825
└─────────────────────────────────────────────┘
                         │
                         ▼
┌─────────────────────────────────────────────────┐
│  Releasing from the patch at least one patch delivered material  │ — 6830
└─────────────────────────────────────────────────┘
```

FIG. 68

SUTURE SLEEVE PATCH AND METHODS OF DELIVERY WITHIN AN EXISTING ARTHROSCOPIC WORKFLOW

CROSS REFERENCE TO RELATED APPLICATIONS

This application is a continuation of U.S. patent application Ser. No. 16/352,721, filed Mar. 13, 2019, titled "SUTURE SLEEVE PATCH AND METHODS OF DELIVERY WITHIN AN EXISTING ARTHROSCOPIC WORKFLOW," now U.S. Patent Application Publication No. 2019/0274675, which is a continuation of U.S. patent application Ser. No. 15/339,782, filed Oct. 31, 2016, titled "SUTURE SLEEVE PATCH AND METHODS OF DELIVERY WITHIN AN EXISTING ARTHROSCOPIC WORKFLOW," now U.S. Pat. No. 10,675,016, which claims priority to U.S. Provisional Patent Application No. 62/248,346, filed Oct. 30, 2015, titled "SUTURE SLEEVE," which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the present invention generally relate to devices and methods for repairing ligaments and tendons, in particular embodiments for repair of rotator cuff tendons using arthroscopically delivered patches.

BACKGROUND

The rotator cuff is a confluence of tendons that connect the muscles originating around the scapula and inserting on the upper humerus. When activated, these muscles raise, lower, and rotate the arm. The rotator cuff tendons measure about 5 cm in width, on average, and together they form a cuff that encapsulates the article surface at the top of the humerus. The acromion (the bone on the top of the shoulder) forms a bony and ligamentous arch over the rotator cuff and is bordered by the acromioclavicular ligament, the coracoid (the bone in front of the shoulder), and the acromioclavicular joint.

The rotator cuff can be injured by a number of different mechanisms. For example, if a person falls and lands on his shoulder, the acromion can strike the rotator cuff causing injury to the muscles or tendons. The extent of the injury, which can be either a bruise or tear, depends on the position of the arm during the fall, the strength and flexibility of the muscles and tendons, and the geometry of the undersurface of the acromion.

When the cuff is bruised, bleeding into the tendons may occur, and the tendons can swell, causing the cuff to be compressed, given the relative narrowness of the space provided for the cuff. This condition may persist for some months and is typically characterized by weakness and pain, especially when the outstretched arm is raised to the side or rotated. Symptoms are usually self-limited after appropriate treatment.

A torn rotator cuff is a significantly more serious problem. Symptoms are similar, although nighttime pain is often more intense, and the ability of the muscle to move the arm is significantly weakened, resulting in limited motion. If the condition does not stabilize over time with rest and supportive care, surgery is often recommended (especially in cases where the cuff tear is significant, and/or in order to prevent the development of osteoarthritis). The size of the tear is typically determined using an arthrogram or by MRI.

While the surgical repair has historically been performed as an open procedure (and more recently as a "mini-open" repair), the majority of rotator cuff repairs are now repaired fully arthroscopically, with the tendon being reattached directly to the bony insertion on the lateral borer of the humerus. However, when direct reattachment is not possible, for example, because retraction of the muscle has created a large defect, interposition devices or grafts (including synthetic cuff prostheses) are used to fill the defect. Devices (or grafts) are also used as augmentation devices to strengthen a repair to prevent recurrent tears and allow for a more aggressive rehabilitation particularly in younger patients.

It is estimates that approximately 250,000 rotator cuff repair procedures are performed each year to alleviate the persistent pain and discomfort associated with shoulder injuries, and help patients regain full range of motion. There is thus a significant need for improved use and integration of devices to aid in or augment healing of a repair within an existing surgical workflow. Moreover, there remains a need for the development of such devices and integration within existing suture repair workflow.

SUMMARY OF THE DISCLOSURE

A variety of different patch structures adapted for suture delivery are described herein for rotator cuff repair should be useful in the treatment of patients with torn rotator cuffs readily since the patch is delivered within the existing surgical workflow and may be used to provide a variety of different materials to improve healing of the surgical site.

In general, in one embodiment, a device to promote healing at a suture surgical repair site includes a patch having an overall shape, a proximal end and a distal end, and a suture conduit along the patch sized to allow passage of a suture and permit relative movement of the patch along a suture disposed within the suture conduit.

This and other embodiments can include one or more of the following features. When the patch is positioned to promote healing at the surgical repair site, a suture can be disposed within the suture conduit and can extend along the patch beyond the proximal end and beyond the distal end. The suture conduit can be a continuous conduit from the proximal end to the distal end of the patch. The suture conduit can be a segmented conduit having two or more suture guide structures spaced along the patch to align the suture disposed within the two or more suture guide structures relative to the proximal end and a distal end of the patch. The two or more suture guide structures can be formed using an element used to assemble the patch. Where the element is a filament, at least a portion of the patch can be assembled by a stitching process using the filament and the two or more suture guide structures are loops of filament formed during the stitching process. The element can be a fastener having a suture guide formed thereon such that when the fastener is engage with a portion of the patch the suture guide is positioned to receive and align the suture relative to the proximal end and the distal end of the patch. The suture conduit can be an aperture formed within the patch extending from the proximal end to the distal end. The suture conduit can be an elongate hollow structure inserted into the patch. The elongate hollow member can be present only while loading the patch on to the suture or while advancing the patch to the surgical repair site. The elongate hollow member can be present when the patch is secured in place in the surgical repair site.

The overall shape of the patch can be rectangular or the overall shape of the patch can include a distal end width of the patch that is different than a proximal end width of the patch and the patch is three sided or four sided. The overall shape of the patch can be generally cylindrical with a cross section shape that is circular, oval, elliptical or rectangular. Each suture at the surgical repair site can be passed through a suture conduit. A portion of each suture used at the suture surgical repair site can be separated from a tissue or a bone of the surgical repair site by a portion of the patch.

The patch can contain a patch delivered material. The patch delivery material can be any of a therapeutic agent, a diagnostic agent, or a prophylactic agent maintained within a layer of the patch, a portion of a layer of the patch or within the patch as a liquid, a powder, a gel, a foam, a particulate media, a solid, a suspended solids, an engineered particle or a nanoparticle. The nanoparticle or the engineered particle the selected from the group consisting of polymeric nanoparticles, metal nanoparticles, gold nanoparticles, PEG coated nanoparticles, liposomes, micelles, quantum dots, dendrimers, and nanoassemblies.

The patch can be configured for designed release of the patch delivery material. The patch can include two or more layers of material. At least one of the two or more layers of material can be selected to carry a patch delivery material. When the patch is in position at the suture surgical repair site, the layer selected to carry a patch delivery material can be directly adjacent to the repair site. When the patch is in position at the suture surgical repair site, the layer selected to carry a patch delivery material can be separated from the surgical repair site by another of the two or more layers of the patch. The patch can be made from materials that are bioabsorbable. The patch can include an upper layer and a lower layer and a layer between the upper layer and the lower layer, wherein one or more of the upper layer, the lower layer and the layer between the upper layer and the lower layer is configured to maintain a patch delivery material according to a selected designed time release of the patch delivery material. The suture conduit can be on, in or within the upper layer. The suture conduit can be on, in or within the lower layer. The suture conduit can be on, in or within the layer between the upper layer and the lower layer. A suture conduit can extend along an outer surface of the patch. The device can further include one or more attachment features positioned along the patch from the proximal and to the distal end to facilitate attachment of the patch to another patch after delivery to the suture surgical repair site.

The patch can be constructed of a biodegradable material having a hybrid of a porous material and a material that provide strength construct. The patch can be formed from a PLA or PGA mesh and strips of PLA or PGA are provided for support. The patch can include a component selected for retention of patch delivered materials while another component is selected to provide strength or other functional attributes of the patch. The patch can include one or more layers of a non-woven mesh, a woven mesh or a knitted multifilament mesh. The device can further include a portion of the patch folded into a plurality of pleats. The patch can be deployed into the surgical site, and at least a portion of the plurality pleats remain. The patch can include a scaffold sandwiched between outer layers of a non-woven mesh, a woven mesh or a knitted multifilament mesh. One or more layers of the patch can be joined into a unitary structure by stitching the layers together with fibers, bioabsorbable fibers, or suture, or by joined together by cementing, bonding, embroidering or by thermal processing such as sealing or welding. The patch delivery material can be selected to promote a desired interaction including an onset, an increase, a decrease or a cessation of a related therapeutic, pharmacodynamic, biologic or other effect upon release at the surgical repair site. The patch delivery material can be selected to promote a desired interaction including stimulating tissue in-growth, promoting tissue regeneration, preventing adhesion formation, or preventing infection at the surgical site. One layer, one portion of one layer, or one portion of a patch can contain an autograft material, an allograft material, or an xenograft material selected for use at the suture surgical repair site. One layer, one portion of one layer, or one portion of a patch can be configured to a patch delivery material including an agent according to a selected designed time release of the patch delivery material. The agent can be one or more of a analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelmintic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; and oncolytic agents.

In general, in one embodiment, a device to promote healing at a suture surgical repair site includes a patch having an overall shape, a proximal end and a distal end, and a first suture conduit and a second suture conduit along the patch sized to allow passage of a suture through each of the first suture conduit and the second suture conduit and permit relative movement of the patch along a suture disposed within each of the first and the second suture conduits.

This and other embodiments can include one or more of the following features. When the patch is positioned to promote healing at the surgical repair site, a suture can be disposed within the first suture conduit and a suture can be disposed within the second suture conduit extend along the patch beyond the proximal end and beyond the distal end. The first and the second suture conduits can each form a continuous conduit from the proximal end to the distal end of the patch. The first and the second suture conduits can each form a segmented conduit having two or more suture guide structures spaced along the patch to align the suture disposed within the two or more suture guide structures of each of the first and the second suture guide conduits relative to the proximal end and a distal end of the patch. The two or more suture guide structures can be formed using an element used to assemble the patch. The device where the element can be a filament, at least a portion of the patch can be assembled by a stitching process using the filament and the two or more suture guide structures can be loops of filament formed during the stitching process. The element can be a fastener having a suture guide formed thereon such that when the fastener is engage with a portion of the patch, the suture guide can be positioned to receive and align the suture relative to the proximal end and the distal end of the patch. Each of the first suture conduit or the second suture conduit can be an aperture formed within the patch extending from the proximal end to the distal end. Each of the first suture conduit or the second suture conduit can be an elongate hollow structure inserted into the patch. The elongate hollow member can be present only while loading the patch on to the suture or while advancing the patch to the surgical repair site. The elongate hollow member can be present when the patch is secured in place in the surgical repair site. The overall shape of the patch can be rectangular or the overall shape of the patch can include a distal end width of the patch that is different than a proximal end width of the patch and the patch is three sided or four sided. The overall shape of the patch can be generally cylindrical with a cross section shape that is circular, oval, elliptical or rectangular. Each suture at the surgical repair site can be passed through a suture conduit. A portion of each suture used at the suture surgical repair site can be separated from a tissue or a bone of the surgical repair site by a portion of the patch. The patch can contain a patch delivered material. The patch delivery material can be any of a therapeutic agent, a diagnostic agent, or a prophylactic agent maintained within a layer of the patch, a portion of a layer of the patch or within the patch as a liquid, a powder, a gel, a foam, a particulate media, a solid, a suspended solids, an engineered particle or a nanoparticle. The nanoparticle or the engineered particle can be selected from the group consisting of polymeric nanoparticles, metal nanoparticles, gold nanoparticles, PEG coated nanoparticles, liposomes, micelles, quantum dots, dendrimers, and nanoassemblies. The patch can be configured for designed release of the patch delivery material. The patch can include two or more layers of material. At least one of the two or more layers of material can be selected to carry a patch delivery material. When the patch is in position at the suture surgical repair site, the layer selected to carry a patch delivery material can be directly adjacent to the repair site. When the patch is in position at the suture surgical repair site, the layer selected to carry a patch delivery material can be separated from the surgical repair site by another of the two or more layers of the patch. The patch can be made from materials that are bioabsorbable. The patch can include an upper layer and a lower layer and a layer between the upper layer and the lower layer, wherein one or more of the upper layer, the lower layer and the layer between the upper layer and the lower layer can be configured to maintain a patch delivery material according to a selected designed time release of the patch delivery material. The suture conduit can be on, in or within the upper layer. The suture conduit can be on, in or within the lower layer. The suture conduit can be on, in or within the layer between the upper layer and the lower layer. A suture conduit can extend along an outer surface of the patch. The device can further include one or more attachment features positioned along the patch from the proximal end to the distal end to facilitate attachment of the patch to another patch after delivery to the suture surgical repair site.

The patch can be constructed of a biodegradable material having a hybrid of a porous material and a material that provide strength construct. The patch can be formed from a PLA or PGA mesh and strips of PLA or PGA are provided for support. The patch can include a component selected for retention of patch delivered materials while another component is selected to provide strength or other functional attributes of the patch. The patch can include one or more layers of a non-woven mesh, a woven mesh or a knitted multifilament mesh. The device can further include a portion of the patch folded into a plurality of pleats. The patch can be deployed into the surgical site, and at least a portion of the plurality pleats remain. The patch can include a scaffold sandwiched between outer layers of a non-woven mesh, a woven mesh or a knitted multifilament mesh. One or more layers of the patch can be joined into a unitary structure by stitching the layers together with fibers, bioabsorbable fibers, or suture, or by joined together by cementing, bonding, embroidering or by thermal processing such as sealing or welding. The patch delivery material can be selected to promote a desired interaction including an onset, an increase, a decrease or a cessation of a related therapeutic, pharmacodynamic, biologic or other effect upon release at the surgical repair site. The patch delivery material can be selected to promote a desired interaction including stimulating tissue in-growth, promoting tissue regeneration, preventing adhesion formation, or preventing infection at the surgical site. One layer, one portion of one layer, or one portion of a patch can contain an autograft material, an allograft material, or an xenograft material selected for use at the suture surgical repair site. One layer, one portion of one layer, or one portion of a patch can be configured to a patch delivery material including an agent according to a selected designed time release of the patch delivery material. When the patch is in position within the surgical space, the width of the distal portion of the patch can be about the same as the spacing between two suture anchors and the distal portion of the patch is wider than the proximal portion of the patch. When the patch is in position within the surgical space, the width of the distal portion of the patch can be about the same as the spacing between two suture anchors. When the patch is in position within the surgical space, the width of the distal portion of the patch can be about the same as the spacing between the two suture anchors providing the suture positioned within the first suture conduit and the suture positioned within the second suture conduit. The suture guided patch selected for delivery into the suture surgical repair site can have a patch having a distal end width that corresponds to a spacing between two suture anchors positioned within the surgical repair site. The suture guided patch selected for delivery into the suture surgical repair site can be a patch having a proximal end width that corresponds to a spacing between two suture anchors positioned within the surgical repair site. The two suture anchors can be directly adjacent one another. A suture anchor can be between the two suture anchors. One or more patch delivered materials can be incorporated into the patch during a manufacturing step or an assembly step, during a step of a surgical preparation, before use during a surgical procedure, before placing the patch into the stowed configuration, while the patch is in a stowed configuration before loading the patch into a delivery tool, while the patch is within a suture loading cartridge, while the patch is loaded into or coupled to a suture guided patch delivery tool or prior to the patch being incorporated into a suture based surgical workflow based on an amount of time needed for adding, loading, incorporating or soaking one or more layer of a suture guided patch with a patch delivered material.

In general, in one embodiment, a method of delivering a suture guided patch to a surgical site includes: (1) placing one or more suture anchors at the surgical site; (2) inserting a suture secured to one of the one or more suture anchors through a suture conduit of the suture guided patch; (3) advancing the patch along the suture in the suture conduit; and (4) securing the patch in the surgical site using the suture in the suture conduit.

This and other embodiments can include one or more of the following features. The placing step can further include pressing or screwing a suture anchor into a bone, a tendon, a ligament, or a muscle at the surgical site. The method can further include performing one or more steps of the suture repair procedure before the inserting suture step. The method can further include delivering another suture guided patch by repeating the inserting step and the advancing step. The method can further include joining the patch to the another patch. The joining step can be performed using one or more loops provided along the patch. The method can further include coupling a modified augmentation device or a modified interposition device to the suture guided patch before or after the inserting a suture step and thereafter performing the advancing the patch step with the modified augmentation device with a modified interposition device. The method can further include performing the inserting a suture step to have a first suture in a first suture conduit and a second suture in a second suture conduit. The patch can be in a stowed configuration during at least a portion of the advancing step. The method can further include moving the patch from the stowed configuration before reaching the surgical site. The patch can move from a stowed configuration after exiting a working channel of a surgical instrument used at the surgical site. The surgical instrument can be one of an endoscope, an arthroscope, or a trocar. The method can further include moving the patch from a stowed configuration using a delivery tool. The method can further include loading the patch onto a delivery tool during the inserting step or before the advancing step. The method can further include adjusting the position of the patch at the delivery site using the delivery tool or a positioning tool provided by the delivery tool. After a step of removing the delivery tool, at least one suture can be in a suture conduit of the patch. The method can further include loading the suture guided patch onto a movable leg delivery device. The one or more sutures can be alongside the movable leg delivery device. The one or more sutures can be within a channel of the movable leg delivery device. The method can further include adding or incorporating a patch delivered material before the inserting step or while the suture guided patch is loaded onto a patch delivery device. The method can further include selecting the suture guided patch based on one or more of a suture conduit spacing, the suture conduit orientation, a number of suture conduit, a patch size, a patch shape and a designed release of a patch material. The method can further include one or more of the steps of trimming a patch, shaping a patch or folding a patch. The one or more steps of trimming, shaping or folding can be performed before the inserting step, after the inserting step, after the advancing step or after the securing step. The suture conduit spacing can be selected based on the spacing between the suture anchors of the sutures in the patch suture conduits. After securing the patch step the width of the distal most portion, the patch can be wider than a proximal portion of the patch. After the securing step, the proximal most end of the patch can be wider than the distal end of the patch. The delivery of the suture guided patch can be a step in a suture-based procedure performed wherein the surgical site includes a joint, a tendon, a bone, or a ligament. The surgical site can be accessed by an open procedure, a minimally invasive procedure, a natural orifice transluminal procedure, an endoscopic procedure, or an arthroscopic procedure. The method can further include loading, providing, incorporating, or encapsulating into the patch at least one patch delivery material. The patch delivery material can be any of a therapeutic agent, a diagnostic agent, or a prophylactic agent maintained within a layer of the patch, a portion of a layer of the patch or within the patch as a liquid, a powder, a gel, a foam, a particulate media, a solid, a suspended solids, an engineered particle or a nanoparticle. The patch delivery material can be selected to promote a desired interaction including an onset, an increase, a decrease or a cessation of a related therapeutic, pharmacodynamic, biologic or other effect upon release at the surgical repair site. The patch delivery material can be selected to promote a desired interaction including stimulating tissue in-growth, promoting tissue regeneration, preventing adhesion formation, or preventing infection at the surgical site. One layer, one portion of one layer, or one portion of a patch can contain an autograft material, an allograft material, or a xenograft material selected for use at the suture surgical repair site. One layer, one portion of one layer, or one portion of a patch can be configured to a patch delivery material including an agent according to a selected designed time release of the patch delivery material. The method can further include releasing from the patch at least one patch delivered material after the securing step. The surgical site can be a shoulder, a foot, an ankle, an elbow, a hand, a wrist, a hip, or a knee.

In general, in one embodiment, a suture guided patch delivery tool includes an elongate body having a proximal end and a distal end, a handle on a proximal end, and a pair of moveable legs on the distal end configured to receive a suture guided patch and a pair of sutures wherein when the patch and the pair of sutures are loaded onto the tool the pair of sutures are alongside the pair of movable legs.

This and other embodiments can include one or more of the following features. The handle can be configured to move the patch and the legs between a stowed condition and a deployed condition. The handle can be configured to release the suture guided patch from the moveable legs. After the release, the suture guided patch from the moveable legs the pair of sutures can remain within one or more suture conduits of the patch. The distal end of the legs can be configured to couple to a pocket or a cuff in the patch. The handle can be configured to release the suture guided patch from the moveable legs by the operation of a release button. The operation of the release button can cause a pair of patch clips or mandibles to open and release the patch from the legs. The amount of movement of the legs can be selected based on the amount of movement for the patch loaded onto the tool to move to a deployed condition. The moveable legs can be wires biased to move a patch towards a deployed condition. The moveable legs can be hollow and the sutures can be loaded into the conduit of the legs and the legs can be positioned within one or more suture loops of the patch. A distal portion of the hollow leg can be reduced to form a shoulder. The patch can include one or more suture loops sized to engage with the reduced distal portion of the hollow leg and a proximal portion of a hollow leg. The tool can further include a push rod along the elongate body and can be engaged with a portion of the patch. A portion of the elongate body can be configured to separate to permit each moveable leg to be removed individually after use. The elongate body can further include a sleeve holding the proximal portion of the delivery tool together. When the sleeve is separated, the moveable legs can be separated. The distal portion of the tool can include a port for adding a patch delivered material to a patch loaded in the tool. The distal portion of the tool can be adapted to receive a patch loading cartridge. The patch loading cartridge can include a port for adding a patch delivered material to a patch loaded in the patch loading cartridge. The proximal end or the distal end of the suture guided patch delivery tool can be adapted to a suture based surgical repair site for delivery of a sutured guided patch configured for use in repair of a shoulder, a foot, an ankle, an elbow, a hand, a wrist, a hip, or a knee.

BRIEF DESCRIPTION OF THE DRAWINGS

FIGS. 21 and 22 are top and side views respectively of a suture guided patch with 2 suture conduits in a generally triangular shape having a wide end and a narrow end.

FIG. 23 is a top view of the patch of FIGS. 21 and 22 shown deployed on a rotator cuff between medial anchors and lateral anchors where the wide portion of the patch is positioned by the medial anchors.

FIG. 24 is a top view of the patch of FIG. 21 with a two-pronged pusher tool engaged to a distal edge of the patch.

FIG. 25 is a side view of the pusher tool shown in use in FIG. 24.

FIGS. 26A, 26B and 26C also illustrate different types of segmented suture conduits.

FIG. 39A is a top view of a suture guided patch having a single suture conduit and a generally rectangular form factor.

FIG. 39B is a top view of a suture guided patch having two aligned suture conduits and a generally rectangular form factor.

FIG. 39C is a top view of a suture guided patch having two aligned suture conduits and a generally rectangular form factor where the spacing of the suture conduits is selected to coincide with the spacing of two suture anchors.

FIG. 39D is a top view of a triangular shaped suture guided patch having two divergent suture conduits generally aligned with two sides of the triangle with the suture conduits closer at the narrow end of the patch and further apart at the wider end.

FIGS. 53A, 53B and 53C are top views of a moveable biased leg patch delivery tool with a patch having a cuff or pocket to engage the distal ends of the biased legs. FIG. 53A shows the tool and patch advanced along the sutures and exiting a working channel with the biasing action of the legs moving the distal end of the patch from a stowed condition. FIG. 53B is a top view of the surgical site of FIG. 53A with the distal portions of the patch and legs of the delivery tool advanced to the suture anchors. FIG. 53C is a top view of the surgical site in FIG. 53B with the legs of the delivery device withdrawn proximally so as to disengage from the pockets or cuffs of the patch.

FIGS. 54A, 54B and 54C are top views of a delivery tool configured to utilize a suture arranged about a portion of an anchor acting as a pulley. The pulling suture is wrapped about the anchor and attached to a distal portion of the patch as best seen in FIG. 54A. FIG. 54A also shows the tool and patch advanced along the sutures and exiting a working channel with the patch moving from a stowed condition. FIG. 54B is a top view of the surgical site of FIG. 54A with the distal portions of the patch advanced to the suture anchors. FIG. 54C is a top view of the surgical site in FIG. 54B with the pull suture separated from the anchor and withdrawn proximally leaving the distal portion of the patch at the medial anchors.

FIG. 55B illustrates the hollow leg device and patch in a stowed condition. FIG. 55A illustrates the hollow leg device and patch in a deployed condition.

FIG. 65A illustrates the sleeve having a perforated segment between each of the proximal portions of the tool. FIG. 65B illustrates a rip cord provided in the sleeve being pulled to separate the legs for removal.

FIG. 66 is a top down view of a hollow leg delivery device that includes a positioning tool or rod. This view shows the delivery tool and patch in a deployed condition with the positioning tool coupled to a distal portion of the patch.

FIG. 67 is a top down view of a hollow leg delivery device that includes a positioning tool or rod adapted to engage with a pocket or cuff provided on the patch as shown in FIGS. 53A-53C. This view shows the delivery tool and patch in a stowed condition with the positioning tool within the pocket or cuff of the patch.

FIG. 68 is a flow chart of an exemplary surgical method for placing a suture guided patch in a surgical site.

DETAILED DESCRIPTION

Embodiments of the present method and apparatus can be used to repair and reconstruct torn ligaments and tendons in a variety of locations of the body. The rotator cuff muscles were selected for the exemplary embodiments because of the complexity of the human shoulder. It will be appreciated that the methods and apparatus according to embodiments of the present invention may have many other possible applications.

Figure 1:
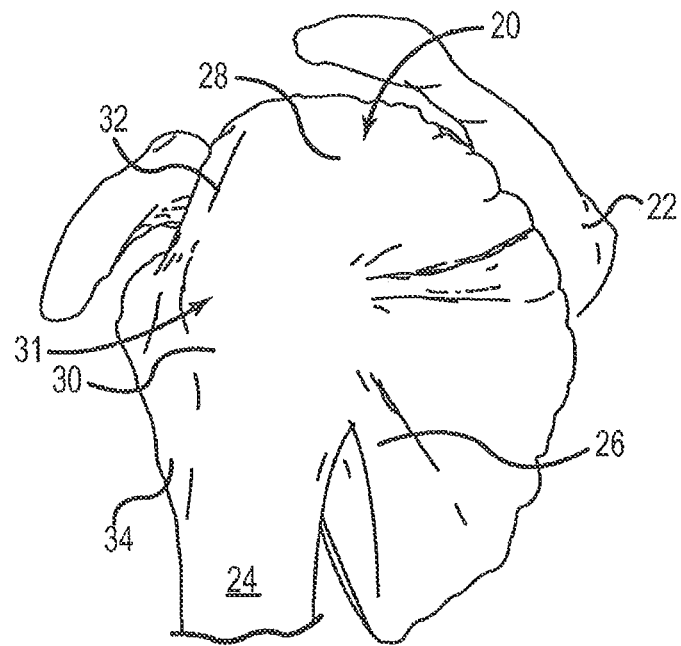
FIG. 1 is a posterior-lateral anatomical view of an anatomical human shoulder.

FIGS. 1-5 are taken from U.S. Patent Application Publication Number 2008/0188936, published on Aug. 7, 2008, which is incorporated by reference herein in its entirety. As illustrated in FIG. 1, the rotator cuff 20 is the complex of four muscles that arise from the scapula 22 and whose tendons blend in with the subjacent capsule as they attach to the tuberosities of the humerus 24. The subscapularis 26 arises from the anterior aspect of the scapula 20 and attaches over much of the lesser tuberosity. The supraspinatus muscle 28 arises from the supraspinatus fossa of the posterior scapula, passes beneath the acromion and the acromioclavicular joint, and attaches to the superior aspect of the greater tuberosity 30. The infraspinatus muscle 32 arises from the infraspinous fossa of the posterior scapula and attaches to the posterolateral aspect of the greater tuberosity 30. The teres minor 34 arises from the lower lateral aspect of the scapula 20 and attaches to the lower aspect of the greater tuberosity 30. Proper functioning of the rotator, 3 to 4 millimeters thick, depends on the fundamental centering and stabilizing role of the humeral head 31 with respect to sliding action during anterior and lateral lifting and rotation movements of the arm.

The insertion of these tendons as a continuous cuff 20 around the humeral head 31 permits the cuff muscles to provide an infinite variety of moments to rotate the humerus 24 and to oppose unwanted components of the deltoid and pectoralis muscle forces. The insertion of the infraspinatus 32 overlaps that of the supraspinatus 28 to some extent. Each of the other tendons 26, 34 also interlaces its fibers to some extent with its neighbor's tendons. The tendons splay out and interdigitate to form a common continuous insertion on the humerus 24. The biceps tendon is ensheathed by interwoven fibers derived from the subscapularis and supraspinatus.

The mechanics of the rotator cuff 20 is complex. The cuff muscles 20 rotate the humerus 24 with respect to the scapula 22, compress the humeral head 31 into the glenoid fossa providing a critical stabilizing mechanism to the shoulder (known as concavity compression), and provide muscular balance. The supraspinatus and infraspinatus provide forty-five percent of abduction and ninety percent of external rotation strength. The supraspinatus and deltoid muscles are equally responsible for producing torque about the shoulder joint in the functional planes of motion.

The rotator cuff muscles 20 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. As another example, use of the latissimus dorsi in a movement of pure internal rotation requires that its adduction moment be neutralized by the superior cuff and deltoid. Conversely, use of the latissimus in a movement of pure adduction requires that its internal rotation moment be neutralized by the posterior cuff and posterior deltoid muscles.

The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action.

By contrast, muscles in the knee generate torques primarily about a single axis of flexion-extension. If the quadriceps pull is a bit off-center, the knee still extends. Consequently, the human shoulder is a good tool to illustrate the present method and apparatus.

Figure 2:
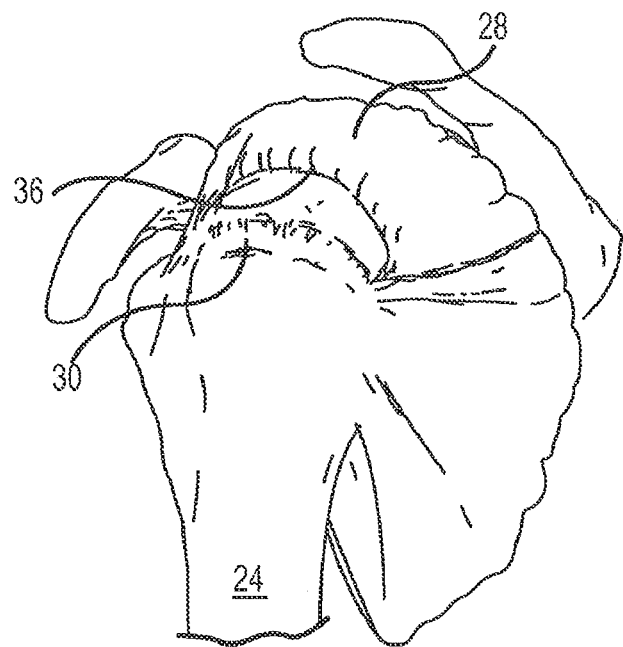
FIG. 2 is a posterior-lateral anatomical view of a left human shoulder with a torn supraspinatus tendon.
Figure 3:
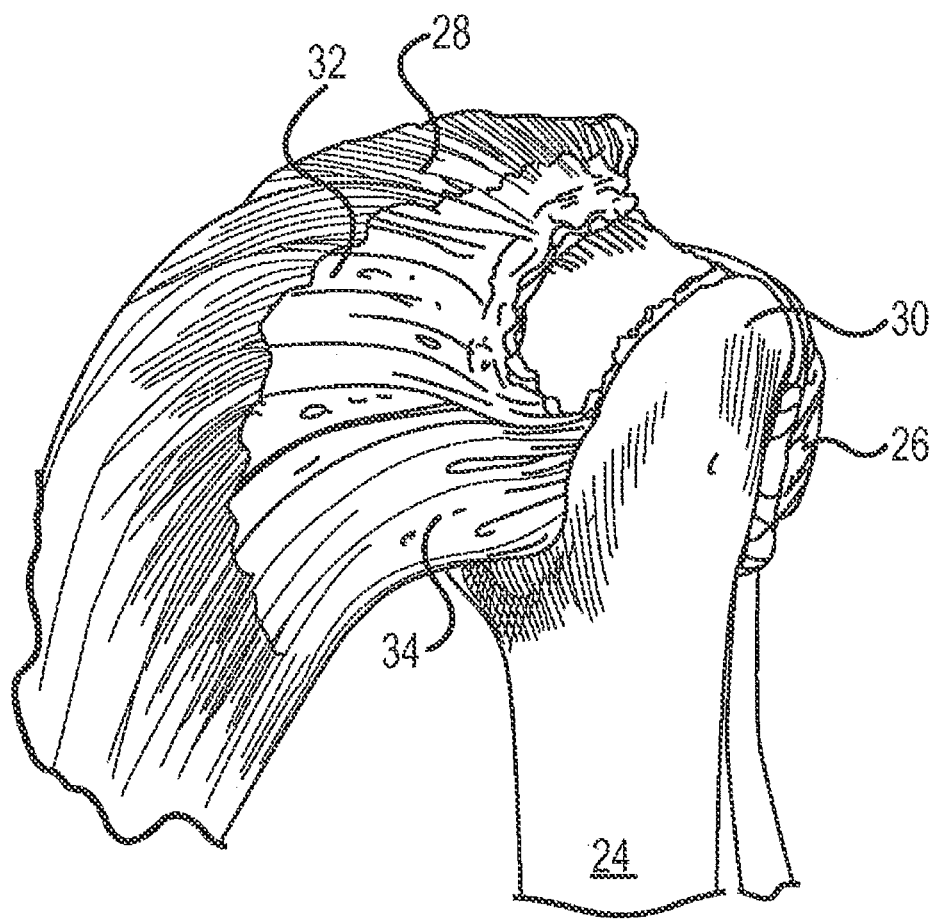
FIG. 3 is a posterior anatomical view of a right human shoulder with a torn supraspinatus tendon.

The suprasinatus 28 frequently tears away from the humerus 24 due to high stress activity or traumatic injury. FIG. 2 is an anterior view of a human left shoulder with a torn supraspinatus tendon 28. FIG. 3 is a posterior view of a human right shoulder with a torn supraspinatus tendon 28. The supraspinatus 28 has separated from the humerus 24 along its lateral edge 36 away from its attachment surface or "footprint" in the greater tuberosity 30.

Surgical repair is usually accomplished by reattaching the tendon back in apposition to the region of bone from which it tore. For the supraspinatus tendon 28 this attachment region, commonly called the "footprint", occurs in a feature of the humerus 24 called the greater tuberosity 30. Repair is generally accomplished by sutured fixation of the tendon 28 directly to holes or tunnels created in the bone, or to anchoring devices embedded in the bone surface. The methods and patches described herein may be adapted according to the surgical procedure used as well as surgeon preference.

Figure 4:
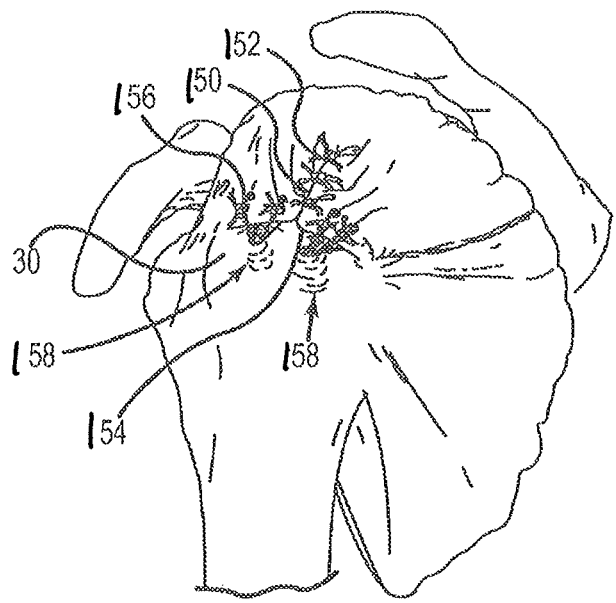
FIG. 4 is a posterior-lateral anatomical view of a left human shoulder with a prior art arthroscopic repair of a torn supraspinatus tendon.

FIG. 4 shows a conventional arthroscopic repair of the torn suprasinatus tendon 28. The margins of the tear have been brought together at a convergence line 150 and closed by tendon-to-tendon stitches 152. The lateral edge 154 has been brought into apposition with the greater tuberosity 30 and secured in place through the use of four sutures 156 secured to two bone anchors 158 driven into the bone in the vicinity of the greater tuberosity 30. This state-of-the-art repair is subject to a 20-60% failure rate, primarily due to suture tear-out from poor quality tendon tissue.

Figure 5:
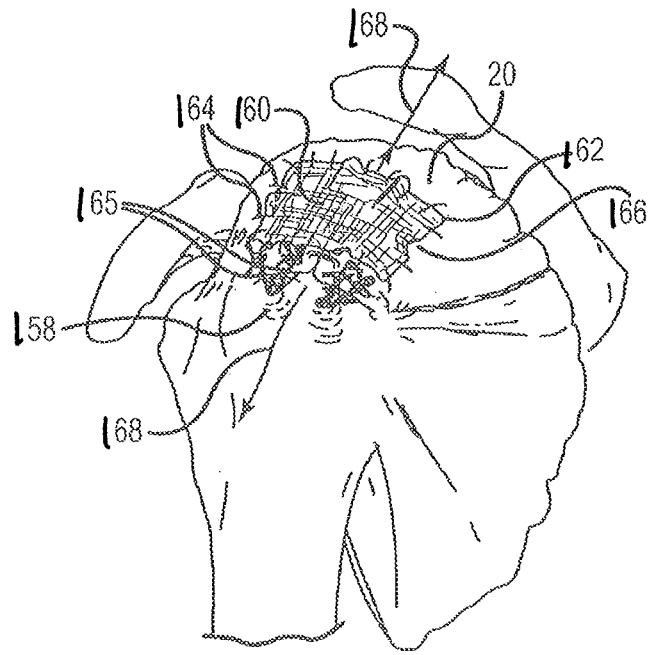
FIG. 5 is a posterior-lateral anatomical view of a left human shoulder with a prior art patch repair of a torn supraspinatus tendon.

FIG. 5 shows an improvement to the repair of FIG. 4 with the addition of a conventional patch augmenting the repair. The edges 162 of the substantially planar patch 160 are attached to the rotator cuff tendon 20 by sutures 164. As is the typical practice, the sutures used in the repair of FIG. 4 are not used to deliver patch 160. Similarly, patch 160 is delivered separately from sutures 164 used to secure the patches.

The surgical repair of a damaged tendon to bone, either performed arthroscopically or utilizing an open technique, is not always successful. This is especially true in a chronic setting in which the muscle is atrophied or the tendon is retracted away from its bony attachment site or both. For this reason, a number of groups have reported on the perioperative use of substances thought to enhance the healing of a tendon to bone following surgical repair. Substances reportedly used for this purpose include bone marrow cells, cellular growth factors (such as interleukins) and platelets and combinations of these and other like substances. The challenge for the surgeon is delivering these substances in a manner that optimizes the length of time that these substances remain in the surgical repair site. Embodiments of the patch described herein provide solutions to the aforementioned challenge.

Figures 19, 20:
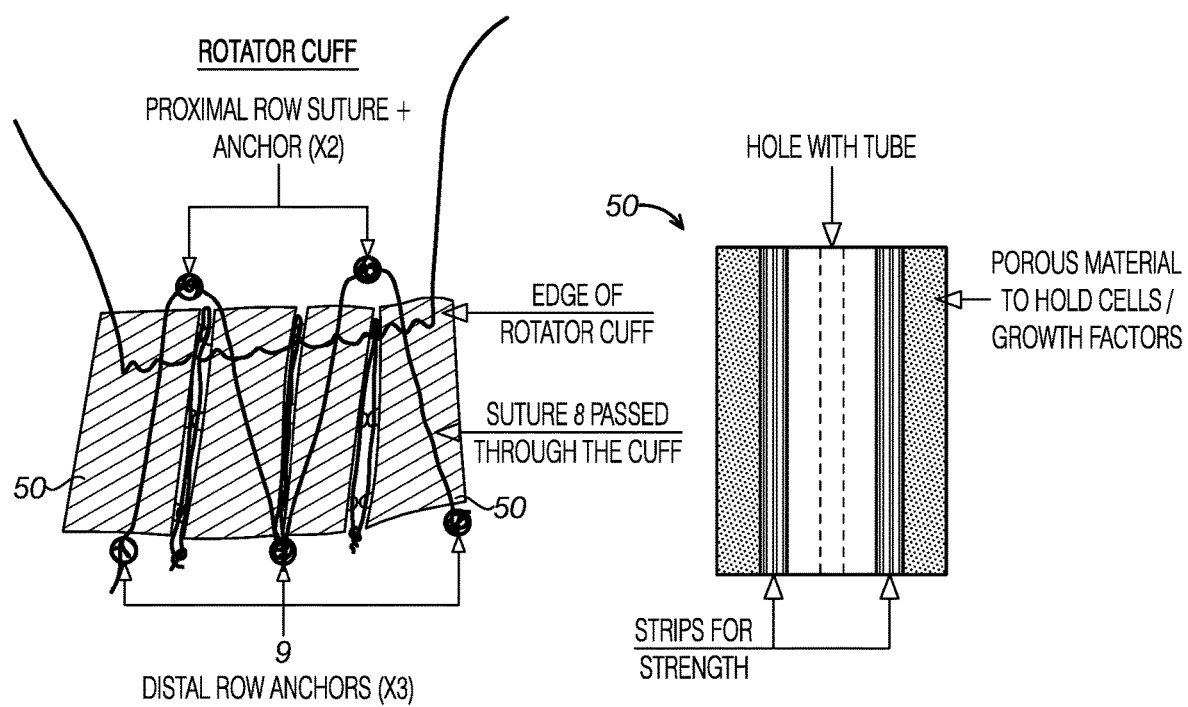
FIG. 19 is a top view of two suture patches attached to sutures between medial and lateral row anchors on a rotator cuff. The patches are shown aligned to permit side by side engagement.
FIG. 20 is a top view of a suture patch of hybrid construction of an array of strips having one material that is porous for holding patch delivered materials and another material selected to provide overall structure and strength to the construct.
Figure 36:
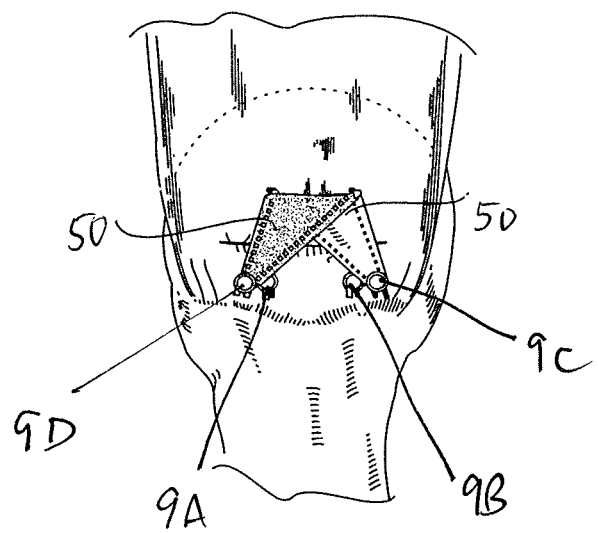
FIG. 36 is a top view of the surgical site of a suture guided patch based rotator cuff repair of FIG. 35 where the suture strands have been trimmed back to or otherwise secured in the surgical site.
Figure 38:
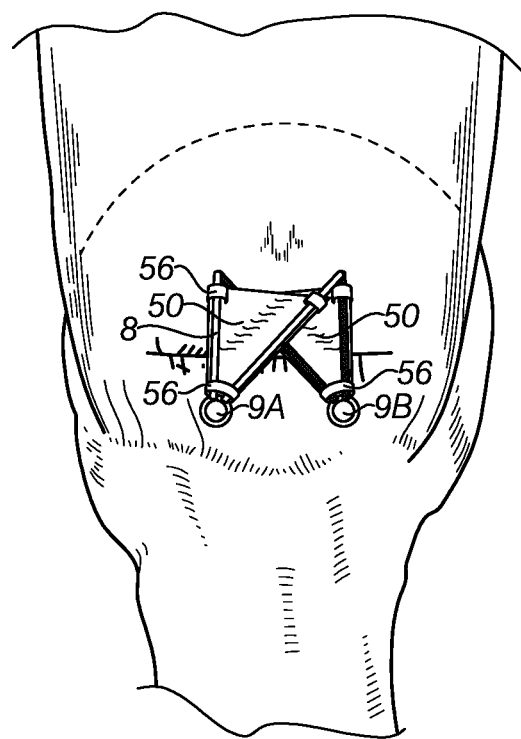
FIG. 38 is a top down view at the conclusion of the alternative suture patch repair of FIG. 37 with two suture guided patches on the rotator cuff repair. This view also illustrates the suture within the segmented suture conduits of both patches as well as the use of the lateral row anchors instead of adding third anchors as in FIG. 36.

In various aspects, this application provides new medical devices for suture based repairs that can be delivered via existing sutures used in a procedure. Embodiments of the inventive suture delivered patch devices are delivered using suture guided techniques along an existing anchored suture. The suture is provided within an "in progress" surgical workflow. A suture patch includes at least one suture channel that is positioned relative to the patch so that after movement of the suture patch along the suture and delivery and deployment into the surgical site the patch is in the desired orientation relative to the suture, the suture anchor, the surgical site and other suture patches (if used) or any augmentation or interposition device (if used). As a result, the patch may be used to augment the repair of the human rotator cuff and other soft tissue structures. Patch may be constructed from a biodegradable material having a hybrid of a porous material and a material that provide strength construct. In one example, the patch is formed from a PLA or PGA mesh and strips of PLA or PGA are provided for support. In other words, the patch may include components selected based on for retention of patch delivered materials while other components may be selected to provide strength or other functional attributes of the patch. One or more patches may be linked together at the surgical site as best seen in FIG. 19, or places in overlapping arrangements as best seen in FIGS. 36 & 38. Additionally or optionally, the patches may be used alone. Still further, and discussed in greater detail below, the patch may be preloaded with a patch delivered material designed to promote healing of the tissue or material and/or cells may be added prior to use.

A patch adapted for suture delivery using the techniques described herein includes patches of a wide array of different size, shape, composition and construction. A patch may have a unitary construction of one or substantially one mostly unitary material, a composite or mixed material, formed of one or multiple layers including "sandwiched" or repeating or alternating stacks of different types of layer materials and hybrid designs including combinations of the above.

Suture guided patches, referred to generally as patches, for advantageous delivery using the suture-based delivery techniques may, in certain embodiments, be formed from absorbable polymers, biocompatible and bioabsorbable polymer fibers and other materials which are absorbable and suited to the repair of rotator cuff tears and other tendon or ligament repairs. In one aspect, a patch comprises absorbable polymer or polymer fiber or structures that provide sufficient initial strength and shape retention to move from stowed to deployed, expand into deployed shape and retain deployed shape at the surgical site, withstand forces relative to the suture including the relative movement along the suture during deployment, loading forces for repair provided by the use of the suture (i.e., tightening), to stand loading of the suture once anchored in place and remaining in place and with enough shape retention during the ongoing healing process at the surgical site and the movement of the joint or repaired surface as a result of physical therapy and/or increased activity post-surgery. As such, it is to be appreciated that with regard to the strength of materials used to join and hold the surgical repair, the suture delivered patch devices provide an insubstantial amount of assistance or, more correctly, when compared to compared to the loads of the suture, are of no consequence to the forces to maintained in a successful surgical repair.

In contrast to conventional suture delivery techniques where patches are pulled through working channels, inventive techniques described herein are similar to those delivery techniques used in vascular surgery through the use of guide wires and designs of devices that may be stowed in a compact form and then deployed into a larger size, shape when delivered to the appropriate surgical site. In much the same way, various alternative designs of suture guided patches place the suture in the position of a guidewire with patches designed for delivery through the working channel of instruments and then for a controlled release at or while being delivered to the surgical site. The use of multiple smaller, overlapping patches replaces the conventional approach (i.e., "one repair-one patch") where a single large patch sized to nearly completely cover the repair is used. As a result, the suture delivered patches along with the variety of patch delivered materials provides methods for easier to deliver patches that integrate into the existing surgical workflow also providing greater ease in adapting patch size, surgical repair coverage, as well as patient specific patch delivered material combinations for greater surgical options and flexibility.

The patch should have sufficient structural integrity to allow them to be retained by sutures without tearing. The patch should also have sufficient initial strength to retain the shape of a suture conduit and to prevent a tear as a result of movement of the patch along the suture. Additionally, the patch should have sufficient initial strength to support movement of the patch in a stowed configuration with respect to the surgical delivery system or associated delivery tool. In one aspect, a patch is provided in one of a number of pre-determined widths such as 1.0 cm, 1.5 cm or 2.0 cm to accommodate estimated anchors or surgical site spacing ranging between 0.8 cm-1.5 cm. In still another aspect, a patch width is selected to approximate a spacing between suture anchors. The dimensions of a specific patch embodiment will vary according to the particular use of the patch. The patch may be selected to be wider than the estimated spacing or contain pleats. As such, the actual patch width is fully deployed (i.e., laid flat) would be wider than the deployed span at the surgical site. In one embodiment, a patch may have a pre-set length ranging from 1.5-2.0-2.5 cm or other pre-set lengths depending on use.

(The patch should be designed to retain strength long enough for delivery and movement/manipulation during implantation at the surgical site as well as to remain in place during long enough to allow the body to heal, and permit the patient to begin physical therapy and return to normal activity. The patches should ultimately be absorbed completely or substantially in relation to the delivery or substantially complete delivery of the patch delivered materials provided by the patch. The time period for the substantial absorption of the devices is less critical than the patch having sufficient strength retention to remain in place until the full material payload is delivered to the surgical site.

In one specific embodiment, the suture delivery patch includes a composition of the device having a non-woven scaffold of sandwiched between outer layers of a knitted multifilament mesh. In one additional embodiment, the device is prepared from multifilament yarn. In one aspect, the patch is pleated to provide additional material at the surgical site. In one aspects the pleats formed in the patch are of sufficient number or size that a portion of the pleats remain in a pleated condition after the patch is deployed in the surgical site and released from the delivery tool or device. In another aspect, all or substantially all of the pleats formed in a patch device are removed when the patch is deployed in the surgical site and released from the delivery tool.

In one aspect, a suture patch is assembled by sandwiching a non-woven mesh between knitted multifilament meshes to form a 3-ply construct and thereafter modifying the construct as described herein to provide a suture channel as well as provide for appropriate attachment to and delivery using a patch delivery device. Other combinations of the non-woven mesh and knitted multifilament mesh may also be used, including, but not limited to, a 2-ply construct comprising a knitted multifilament mesh with a non-woven mesh in multiple different numbers of piles alternating between different types such as non-woven, woven, knitted and the like. The thickness, order, size, dimension and orientation of each layer relative to the overall patch and adjacent layers may be adjusted depending upon the design characteristics of particular patch (see FIGS. 40A, 40B). Still further, a patch may also be formed from other fiber-based constructs, including monofilament meshes and terrycloth constructs. In these and in other variations, the various layers of the patch may be held together, for example, by stitching the layers with fibers, bioabsorbable fibers, or suture, or by other suitable methods such as bonding, embroidering or thermal welding depending upon the design characteristics of a patch. If desired, the patch may be further reinforced with mono- or multifilament fibers. Similar techniques may be used to provide or form on a patch one or more segmented suture channels (see FIGS. 42C, 42D and 42E), form or affix one or more continuous suture channels as best seen in FIGS. 41A-41D or provide loops suited for joining patches together (see FIGS. 17 and 18) or as a process to join a suture guided patch to an modified augmentation device or modified interposition device as described above.

In one aspect, the suture delivered patch has enough structure so that the patch does not bind or bunch in a stowed condition nor tear when moving to a deployed condition. Embodiments of the suture delivered patch will fold and unfold without tearing and will retain shape through the loading delivery and deployment process. Additionally, the patch is not bulky and may be compressed when in a stowed condition so that it may be delivered using the various arthroscopic or minimally invasive techniques described herein. The patch is a controlled release reservoir for the patch delivered materials and as such may be thinner and have a lower strength properties than other implanted patch materials, or as found in conventional augmentation devices and interposition devices. Additionally, the patch may remain in the deployed condition when unloaded with enough strength and structural integrity to remain unloaded but still be pliable and formable by the surgeon to adjust the location of the patch at the surgical site. The various patch designs also remain in a deployed condition over time as joint healing and recovery begins. As described above, the sutures carry the load of the repaired tissue. As such, the patch needs only sufficient strength of sufficient duration to remain in position while the joint begins to move and the loading state changes as the patient undergoes physical therapy and the joint healing process progresses. Still further, the degradation or bio absorption of the support structure of the patch is selected and adjusted according to the rate of delivery of the material loaded into the patch as well as the rate of designed release of the materials from the patch. It is to be appreciated that the patch support structure while bioabsorbable remains with sufficient integrity in order to support the structure, matrix or portion of the patch that is loaded with the patch delivery material.

Additional characteristics of the inventive suture delivered patch include: ability to hold and release in a controlled fashion the loaded patch delivered material; ability to move relative to suture during delivery without tearing or shredding; ability to carry no more than 10% of loading from tension of the suture; aid in repair process including the growth of tissue; has enough structural integrity to be positioned accurately during deployment not so flimsy that it simply peels up or so then that it tears rather than unfolds on delivery. Still further, as between the patch and the suture, the suture is performing the repair by maintaining the bone and soft tissue in apposition while the patch aids in the healing process.

A number of different patch form factors are provided by the various different embodiments of the suture patch. One form factor is that of a patch which will work alone or be employed with similar patch configurations but each one operating independently at the surgical site. Another form factor relates to various ways of joining together separate patches after delivery to the surgical site. In one aspect, loops or other structure provided alongside the adjacent portions of the patches may be used to join the patches together, typically by an additional suture operation. Still another form factor relates to the placement of the suture conduit relative to the patch. In one form factor, the conduit runs through the entire length of the patch. The suture conduit may be formed by simply making an appropriate opening in the patch. In another embodiment, a suture conduit is provided by inserting a separate conduit or tube into and along the patch to provide a guide channel for the suture. In still others, the suture conduit is non-continuous or segmented whereby hoops, loops of suture or other guides are provided at a spacing along the patch and thereafter used to hold the suture or a delivery tool used with the suture. Still another form factor includes a suture delivered patch with a suture conduit that is attached, joined, stitched or otherwise provided with an augmentation device or an interposition device whereby the patch provides for suture-based delivery of the augmentation or interposition device "Biocompatible" as used herein means the biological response to the material or device is appropriate for the device's intended application in vivo. Any metabolizes of these materials should be biocompatible.

"Strength retention" as used herein refers to the amount of strength that a material maintains over a period of time following implantation into a human or animal. For example, if the tensile strength of an absorbable mesh or fiber decreases by half over three months when implanted into an animal or human, the mesh or fiber's strength retention at 3 months would be 50%. As described herein, the strength of the patch is related to its ability to withstand delivery along the suture and the movement of the surgical site post-surgery. In contrast to other patches, and joining structures designed for providing strength to the surgical repair, embodiments of the inventive suture guided patch do not play a significant role in providing the force needed or to bear the load imparted in a surgical repair. Typically, the suture used to deliver the suture guided patch-often in combination with one or more other sutures-bear the loads and holds the repaired tissue, bone, ligament, tendon as required at the surgical site. The suture delivered patch assists in promoting the healing process after surgery.

Absorbable as used herein means the complete or substantially complete degradation of a material in vivo, and elimination of its metabolites from an animal or human.

The suture delivery surgical repair patches are adapted for use with suture anchors. Suture anchors are available in a wide array of designs. The devices and methods of patch placement described herein are adaptable to virtually any approved suture anchoring system including smooth or threaded metallic or polymer bone fixation fastener. A suture anchor is intended to reattach soft tissue to bone in orthopedic surgical procedures. The system may be used in either arthroscopic or open surgical procedures. After the anchor is deployed in the bone, the floating sutures provided by the suture anchor can be used to reattach soft tissue, such as ligaments, tendons, or joint capsules to the bone. According to the various embodiments of the present methods, the anchored sutures thereafter act like a guide wire to provide for delivery of embodiments of suture patches into the surgical site while spanning between two implanted anchors. As a result, the suture anchor system thereby stabilizes the damaged soft tissue, in conjunction with appropriate postoperative immobilization, throughout the healing period while also providing one or more arthroscopically delivered patches. Advantageously, embodiments of the inventive patches described herein are adapted and configured for delivery along existing anchored sutures in the existing surgical workflow. In some embodiments, the patches delivered using existing anchored sutures are secured to the surgical site when the sutures themselves are secured in the surgical site. The suture anchors described herein are intended to be used for the reattachment of soft tissue to bone and the sutures provided for this purpose are employed as described in embodiments of the inventive surgical repair patch methods to also secure the surgical repair patch. In some embodiments the sutures are secured into the surgical field using a friction fit into the target bony anatomy. Exemplary suture anchors include solid core anchors or hollow core style anchors or variable interior anchor materials of a hybrid design.

The suture anchor size may be selected upon a number of factors suited to the surgical site and procedure being performed. Similarly, the size and type of sutures provided with the anchor may be selected based on the estimated suture length needed for the repair along with any considerations for anchoring the repair patch. In one aspect, there is provided a pair of floating sutures on each suture anchor provided into the surgical site. In one aspect two floating sutures are provided on each anchor and the colors and types of sutures may be selected from two different solid colors, two different braided colors, a co-braid color combination such as black/white, blue/white, green/white, or other combinations suited to surgeon preference or adaptation of the patch repair method to a particular patient or surgical site or procedure.

In a number of different alternative embodiments, a variety of different types and constructs of the inventive patches described herein may be used with any of a number of different commercially available suture anchors and sutures. In one or more different embodiments, the suture provided by the suture anchor is a nonabsorbable suture or an absorbable suture and is provided as a single filament, multifilament or braided construction. Additionally or optionally, sutures can be comprised of single polymers or polymer blends. Nonabsorbable sutures are made from inert materials including, for example, nylon (available commercially as Dermalon, Monosol, Surgilon, Nurolon and Ethilon), polybutester (available commercially as Novafil, and Vascufil), polyester (available commercially as Surgidae, Ticron and Cottony II), polyethylene (available commercially asMaxBraid, Mersilene and Ethibond), and poly propylene (available commercially as Surgipro, Deklene and Prolene). In other embodiments, an absorbable suture is fabricated from one or one or more biodegradable polymers. Common biodegradable polymers used in sutures include polyglycolic acid (available as Dexon S), PLLA, PDO (available as Monodek and Ethicon) and poly-D, L. lactic acid and their copolymers. Still further, in some embodiments, an absorbable suture can include modifications to improve know tying properties and tensile strength, for example, PGA with a polycaprolactone PGA coating (such as Bondek Plus), poliglecaprone 25 (available as Monocryl), polycaprolate (available as Dexon II), PDO with polyglactin 910 coating (such as Vieryl) and polyglytone (such as Caprosyn).

In still other alternative embodiments, the suture anchors provide floating sutures having monofilament or braided suture structures. In one aspect, a braided polyester suture may be coated with polybutylene for a slicker outer surface to improve arthroscopic knot tying. Other braided structures may also include a coating of PTFE as is common in the commercially available Tevdek and Polydek sutures. In still other aspects, the braided suture may include a core material with the braid wrapped around core. The suture may also be an ultra high molecular weight polyethylene (UHMWPE) surrounded by a polyester braid as is available in a Fiber Wire suture. Additionally or optionally, a braided suture may be provided composed entirely of an ultra high molecular weight polyethylene such as is available as ForceFiber, MagnumWire, Ultrabraid and Hi-Fi. Orthocord is another UHMWPE suture with a PDO core and a coating of polyglactin 910. Any of the above described sutures may also be coated with an appropriate antimicrobial coating to inhibit bacterial growth within the suture material structure.

In various alternatives, a suitable suture anchor may be provided depending upon the needs of the damaged tissue being repaired. The anchor is pre-loaded with a suture at the time of manufacture or at the time of surgery via an eyelet or other aperture or suitable technique to join one or more sutures to the anchor for delivery to the surgical site. In general, a suture anchor may be described as a screw or threaded anchor or an impaction or thread less anchor based on the way an anchor is fixed to the target bone. Still further, a suture anchor may also be classified based on how sutures are tightened, typically, as normal anchors or knotless anchors. Knotless anchors include an eyelet-suture system rendering knot tying unnecessary. Still another way of categorizing suture anchors is based on material. In some embodiments, the suture anchors may be formed from bioinert and biocompatible metals such as titanium, stainless steel and alloys thereof. In some embodiments, the suture anchor is made of a bioabsorbable material or combination. Exemplary materials include PGA, polylactic acid (PLA) a copolymer of PLA and PGA (PLGA) or a combination of the two. Additional alternatives include anchors that are bio- composites having a bioabsorbable polymer and an osteoconductive bioceramic or such materials in combination to accelerate bone formation and mineralization by the timed degradation of the ceramic along with the polymer. Still another alternative suture anchor material is polyetheretherketone (PEEK).

The suture delivered patches are implanted during surgery, at or in place of the damaged tissue, via delivery using the existing sutures already in use during the repair procedure. As such, an embodiment of the suture patch based device may be deployed into the surgical site in a guided and direct manner during any of a wide variety of surgical procedures such as an open procedure, a "mini-open" procedure, a minimally invasive surgical procedure, a natural orifice transluminal surgical procedure (i.e., any of the various NOTES procedures), a single port access procedure, an endoscopic procedure, an arthroscopic procedure or any other scope based procedure by utilizing one or more sutures already in use during the procedure, anchored in place within the surgical site, or provided as part of the surgical workflow. By utilizing the advantageous designs of the inventive path, the one or more sutures already provided are used like guidewires to direct movement of the patch to the desired location within the surgical site, provide for proper placement and alignment with respect to the surgical repair site or other patches if more than one patch is used. In one aspect, especially for any scope delivered procedure such as by an endoscopic or an arthroscopic delivery, the suture patch and delivery tool is readily closed into a stowed condition where the device is closed or in reduced profile with the patch suitably compressed, rolled or folded alongside the delivery device to a size dimensioned to permit passage through a working channel of the scope and to the surgical site. In one aspect, a delivery tool and a patch are threaded onto one or more sutures, placed into a stowed condition and advanced through a working channel of a scope while remaining in the stowed configuration and advancing along the one or more sutures towards the surgical site. In some embodiments, one or more or a combination of patch delivered materials, including therapeutic, diagnostic, and/or prophylactic agents, cells or whole tissues, are added for incorporation into and subsequent designed release or delivery to the surgical site using the suture patch. By way of example, patch delivered materials are incorporated into the patch during manufacturing or assembly or as part of a surgical preparation or before use procedure or before placing the patch into the stowed configuration or while in a stowed configuration before loading the patch into a delivery tool or while waiting to be incorporated into the surgical workflow. In various alternative embodiments, these materials can be used, for example, to render the suture delivered devices radio-opaque, simulate tissue in-growth, promote tissue regeneration, prevent adhesion formation, prevent infection, provide additional reinforcement, to another suture delivered patch.

Additional examples of patch delivered materials, include therapeutic, diagnostic, and/or prophylactic agents, cells or whole tissues, regardless of form, whether in liquid, powder, gel, foam, particulate media, solids or suspended solids, including engineered particles or nanoparticles designed to release one or more of the materials, including various types of encapsulation as well as factors for designed release of material at the surgical site.

As used herein, nanoparticles relate to a form of structures with sizes in the nanometer (nm) range. In principle any collection of atoms bonded together with a structural radius of <100 nm can be considered nanoparticles. In various embodiments of suture guided patch, nanotechnology based materials or structures are provided in order that the interaction of the patch and the surgical site may take advantage of any of a variety of biological and medical processes that occur at nanometer scales. It is generally believed that among the approaches for exploiting nanotechnology in medicine, nanoparticles offer some unique advantages as sensing, image enhancement, and delivery agents. Several varieties of nanoparticles that may be adapted and configured for use in patch delivered materials, include by way of example, polymeric nanoparticles, metal nanoparticles, gold nanoparticles, PEG coated nanoparticles, liposomes, micelles, quantum dots, dendrimers, and nano-assemblies. Various alternative embodiments of suture guided patches include various aspects of nanoparticles or nanoparticles based material delivery including additional details provided in published United States Patent Application Publication Number US 20130004651 and "Nanoparticle—based targeted drug delivery" by R. Singh and J. Lillard, Jr. (Exp Mol Pathol. 2009 June: 86(3): 215-223, published online on Jan. 7, 2009.

Those of ordinary skill will appreciate the cooperative manner with which the embodiment or characteristics of a patch are modified based upon the type of patch delivered material selected, suitable structures for incorporation of the material into the patch, the designed controlled release curve or delivery profile and the like. Designed time release or modified release of patch delivered materials is a deliberate modification of the release rate of patch delivered materials based on a number of factors including, for example, the surgical and patient specific circumstances where the suture patch will be used, the desired interaction with the surgical site, including onset, increase, decrease or cessation of a related therapeutic, pharmacodynamic, biologic or other effect. Accordingly, designed release, as used herein, relates to the manner by which patch delivered materials are introduced to the surgical site according to any of a variety of widely used delivery modes including controlled-release, modified release, extended-release, delayed-release, targeted release or other forms of material introduction based on release technology along with associated mechanisms of action appropriate to suture patch delivered materials. In some embodiments, designed time release also takes into consideration the composition and structure of a suture guided patch, including for example the degradation profile of structural materials used in the patch, along with the structure and properties of the portion of the patch used to store and release the patch delivered materials.

As a result, a wide array of different patch delivered materials-alone or in combination-may be incorporated into and released by design from the various embodiments of the suture delivered patch. Still further, these materials can be used, for example, to render the patches radio-opaque, stimulate tissue in-growth, promote tissue regeneration, prevent adhesion formation, prevent infection, and the like depending upon, for example, patient needs, type of surgery, surgeon preference and the like.

Exemplary agents that are part of patch delivered materials include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelmintic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarryhythmic agents; central nervous system stimulants; diuretics; genetic materials; hormonolytics; hypnotics; hypoglycemic agents; immunosuppressie agents; muscle relaxants; narcotic antagonists; nicotine; nutritional agents; parasympatholytics; peptide drugs; psychostimulants; sedatives; sialagogues, steriods; smoking cessation agents; sympathomimetics; tranquilizers; vasodilators; beta-agonist; and tocolytic agents.

For example, an antibiotic may be added to the patches to prevent or treat an infection. In one embodiment, the suture delivered patch contains a biologically derived implant material. Various different embodiments of the inventive suture guided patch may also incorporate autograft, allograft, and/or xenograft materials. Exemplary biologically derived implant materials have been developed, including allografts, (e.g. Wright Medical GraftJacket™ [Human Dermis]) and xenografts, (e.g. Depuy Restore™ (Porcine SIS), Arthrotek Cuff Patch™ [Porcine SIS], Stryker TissueMend™ [Fetal Bovine Dermis], Zimmer Permacol™ [Porcine Dermis], Pegasus Orthadapt™ [Equine Pericardium], Kensey Nash BioBlanket™ [Collagen], CryoLife ProPatch™ [Bovine Pericardium]). In addition to providing structural reinforcement, these materials are intended to repopulate the host ligament or tendon tissue with appropriate ligament or tendon cells as they are absorbed by the body.

Figure 6:
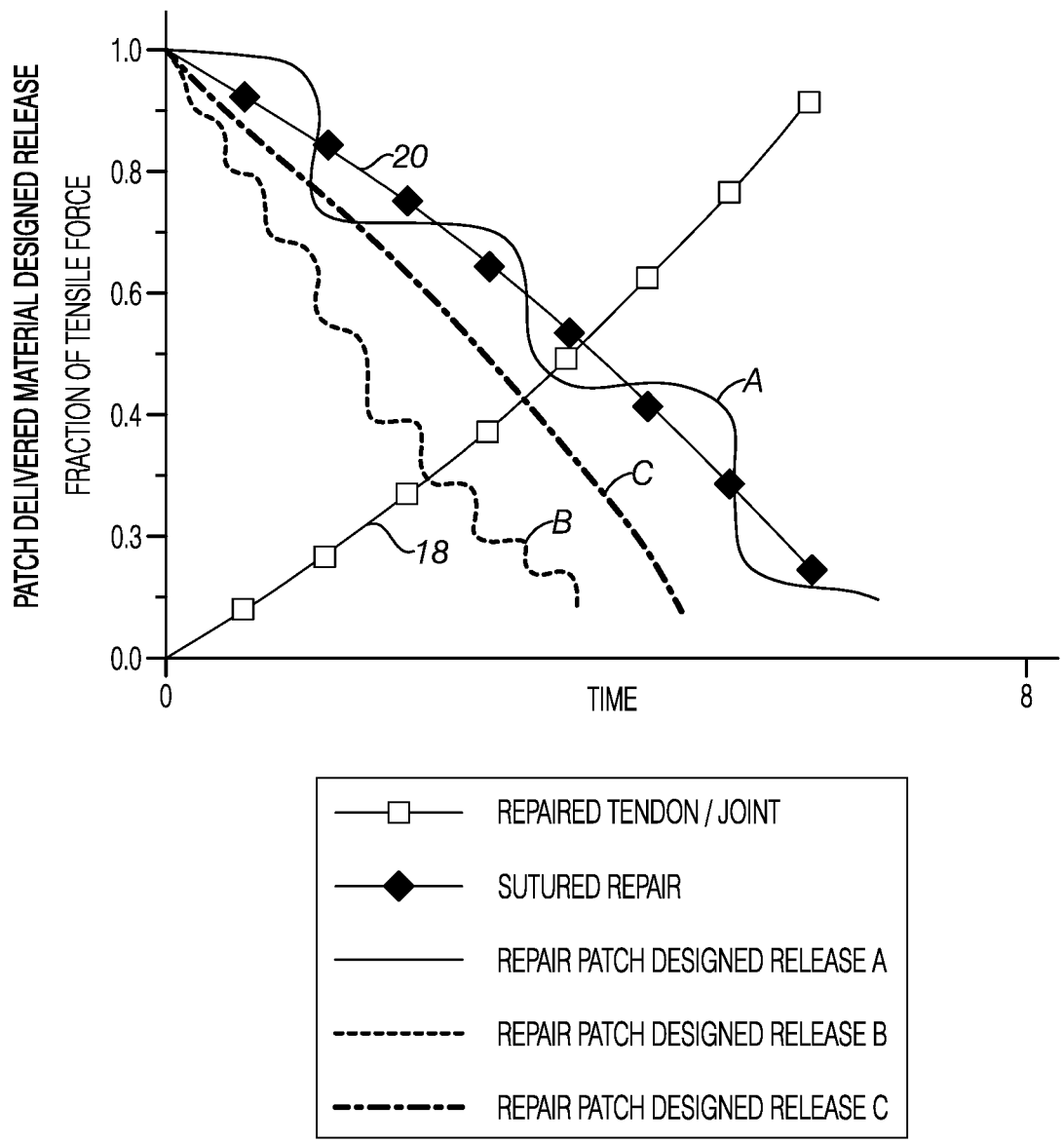
FIG. 6 is a graph illustrating exemplary changes in fraction of tension force born by the repaired tissue and the suture repair along with three representative patch delivery designed release profile during an exemplary 8 week time period.

FIG. 6 is a graph illustrating exemplary changes in fraction of tension force born by the repaired tissue and the suture repair along with three representative patch delivery designed release profile during an exemplary 8 week time period. In use, the various embodiments of the suture guided patch are prepared with both the structural bio absorption of the patch material itself as well as the designed release of the patch delivered material. FIG. 6 is a graph at provides an exemplary representation of the absorption rate of sutures used in the procedure as indicated by the relative strength of the sutures (line 20) to the just repaired tendon or structure (line 18). As can be seen in these illustrative curves, the tension loads are born by the sutures at time t=0 but then shift to the repaired structure gradually as the site heals and the sutures are absorbed. FIG. 6 also shows three different exemplary designed release rates of patch delivered materials. A specific embodiment of a suture guided patch may be designed to provide a designed release in any of a number of different profiles. Curve A illustrates a time delayed release of patch delivered materials at a longer time interval or several days to once a week. Curve B illustrates another time release of patch delivered materials with smaller and more frequent doses than shown in Curve A. In contrast to Curves A and B, Curve C illustrates an exemplary designed release of patch delivered materials that is nearly constant over a sustained period such as the first few weeks after surgery. Curves A, B and C along with curves 18 and 20 are illustrative only to show how the designed release of patch delivered materials may correspond to the bioabsorption of suture or other structure used in the repair of tissue as described herein.

Figure 7:
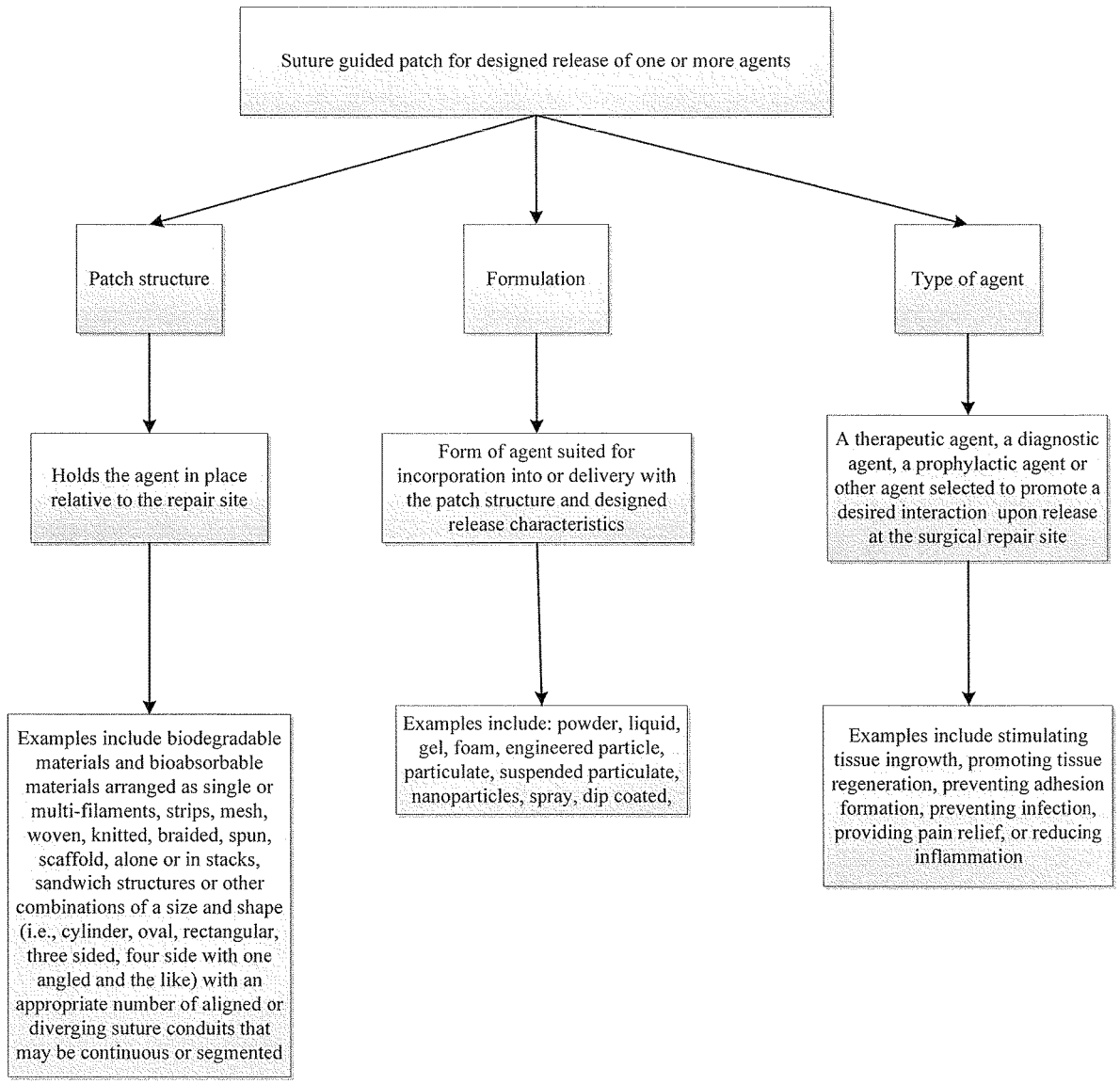
FIG. 7 is a table summarizing three main characteristics of suture guided patches.

FIG. 7 is a table summarizing various properties of suture guided patches including patch structure, as well as the various formulation and types of agents provided as patch delivered materials.

Suture Guided Patches Having a Single Suture Conduit

Various alternative embodiments of the present suture guided patch invention are embodied as disclosed and illustrated in the attached FIGS. 8-20 and accompanying description. In one aspect of the present invention a suture guided patch is embodied in a suture sleeve that has a single suture conduit that surrounds a suture for incorporating and/or delivering chemical and/or biological agents to a suture site. The suture sleeve can be made from a biodegradable and/or permanent base material, be porous and/or configured as a scaffold to incorporate and deliver biologics to a site (i.e., patch delivered materials see outer surface 60 of FIG. 10). The suture sleeve can be used, by way of example and not by way of limitation, for any application that involves a suture or has the need for a delivery vehicle for delivering a chemical and/or biological agent e.g., rotator cuff repair, soft tissue repair, ACL reconstruction, quadriceps tendon repair, ankle tendon repair, etc. The suture sleeve is preferably delivered and assembled to the suture arthroscopically. Preferably, the suture sleeve is formed from collagen, submucosa or Marlex®, but can alternatively be formed from any other suitable material.

Figure 8:
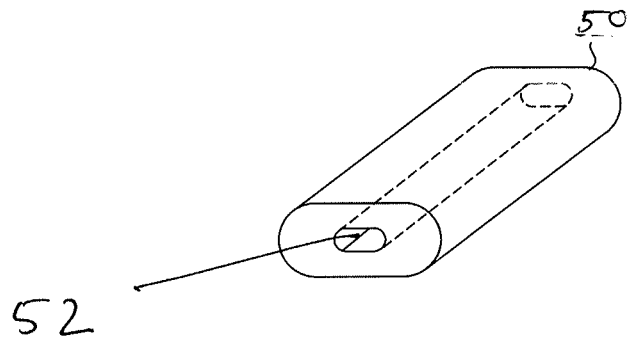
FIG. 8 is a perspective view of a suture guided patch having an oval form factor and a single suture conduit from the proximal end to the distal end.
Figure 9:
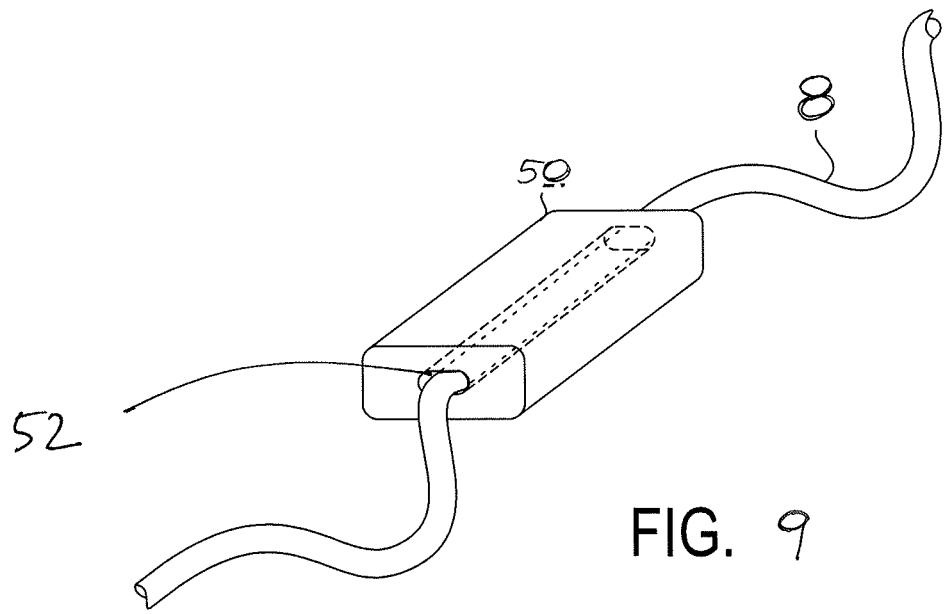
FIG. 9 is a perspective view of a suture guided patch having a rectangular form factor and a single suture conduit with a suture shown in an extending through the conduit from the proximal end to the distal end.
Figure 10:
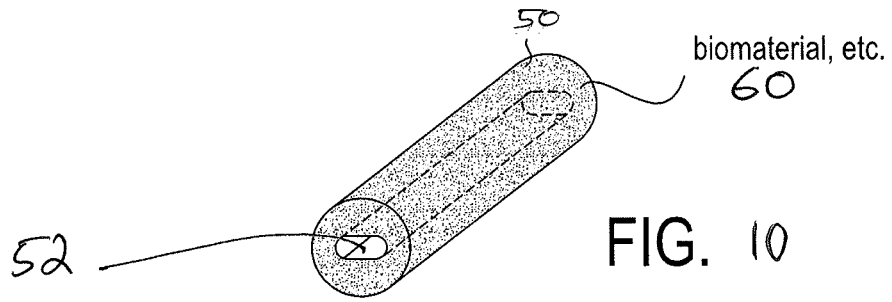
FIG. 10 is a perspective view of a suture guided patch having a cylindrical form factor and a single oval-shaped suture conduit from the proximal end to the distal end.

In accordance with another embodiment, the present invention is embodied as disclosed and illustrated in FIGS. 8, 9 and 10. FIG. 8 is a perspective view of a suture guided patch having an oval form factor and a single suture conduit from the proximal end to the distal end. FIG. 9 is a perspective view of a suture guided patch having a rectangular form factor and a single suture conduit with a suture shown in an extending through the conduit from the proximal end to the distal end. FIG. 10 is a perspective view of a suture guided patch having a cylindrical form factor and a single oval-shaped suture conduit from the proximal end to the distal end.

Figure 11:
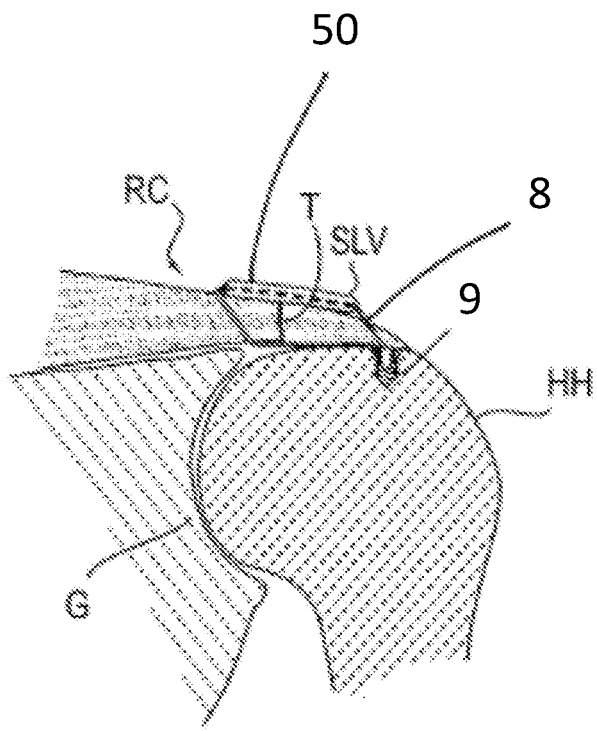
FIG. 11 is a side view of a patch delivered and secured over a repaired portion of a rotator cuff.
Figure 12:
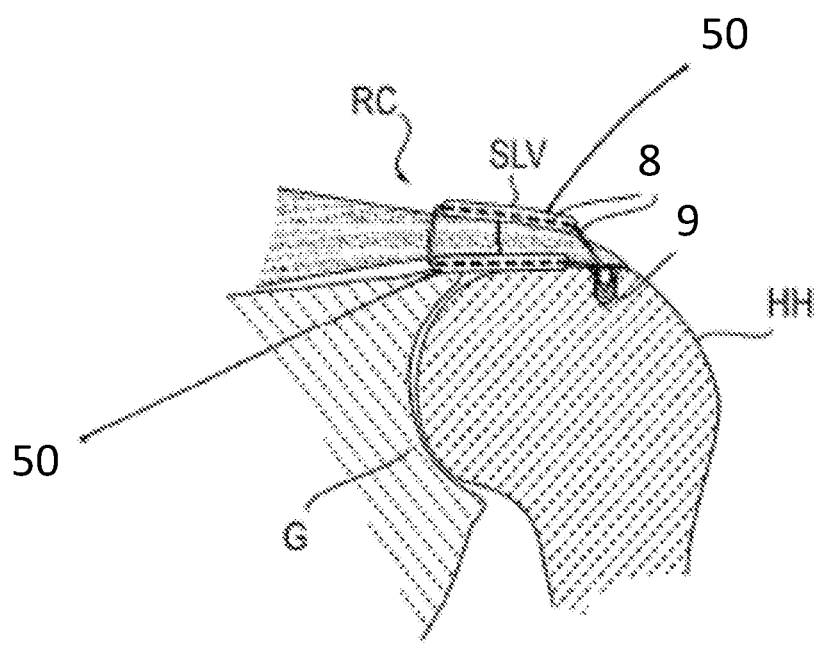
FIG. 12 is a side view of a pair of suture delivered patches in position and secured above and below a repaired portion of a rotator cuff.
Figure 13:
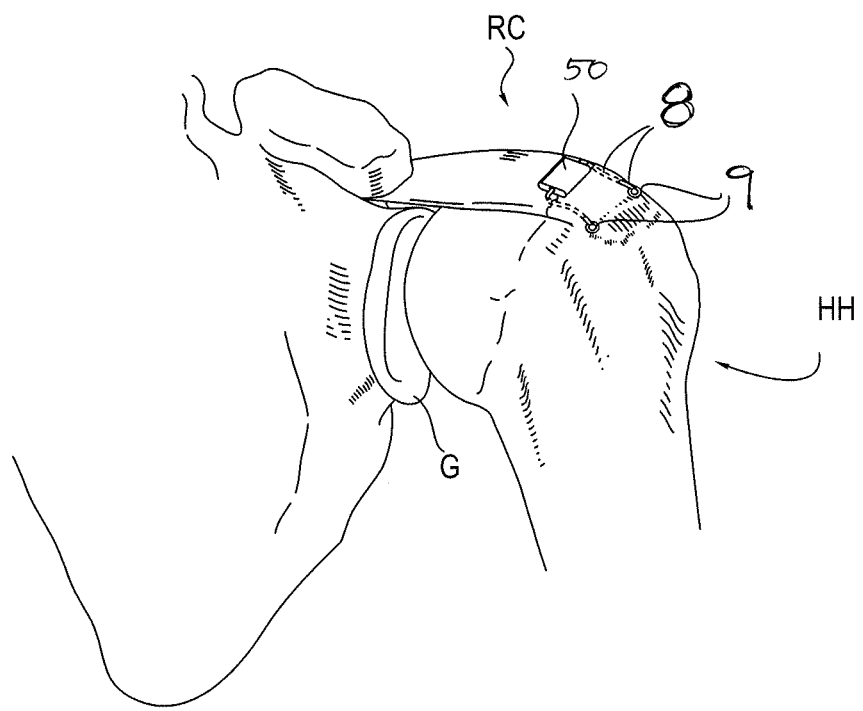
FIG. 13 is a perspective view of a suture patch as in FIG. 9 in place and secured above a repaired portion of a rotator cuff.

This and other embodiments may be used to augment the repair of the human rotator cuff and other soft tissue structures. The device can be applied arthroscopically or during open surgery. FIG. 11 is a side view of a patch delivered and secured over a repaired portion of a rotator cuff. FIG. 12 is a side view of a pair of suture delivered patches in position and secured above and below a repaired portion of a rotator cuff. FIG. 13 is a perspective view of a suture patch as in FIG. 9 in place and secured above a repaired portion of a rotator cuff.

The suture guided patch includes a biodegradable material. The material can be a hybrid of a porous material and a material that provides strength to the construct. Such as, for example, a PLA or PGA mesh and strips of PLA or PGA. FIG. 20 is a top view of a suture patch of hybrid construction of an array of strips having one material that is porous for holding patch delivered materials and another material selected to provide overall structure and strength to the construct. The mesh can be infused with a solution that can be cells such as stem cells or growth factors or both (see materials 60 in FIG. 10). The device is shaped in rectangular form as shown in FIGS. 9, 13, 18, 19, and 20. There is a suture conduit 52 which is a hole in the center of the device that can accommodate a suture 8 as shown in FIG. 9. A shuttle tube 58 may be placed in the hole 52 to facilitate the passing of the suture through the center of the device. A shuttle tube 58 is shown in place in FIG. 18. The tube may then be removed after passing the suture. Suture guided patches or sleeves 50 may be linked together after they have been passed by passing a suture 8 through eyelets 62 located on both sides of the patch 50. The suture delivered patch may be preloaded with a material designed to promote healing of the tissue or material and/or cells may be added in the operating room (i.e., patch delivered materials).

Figure 14:
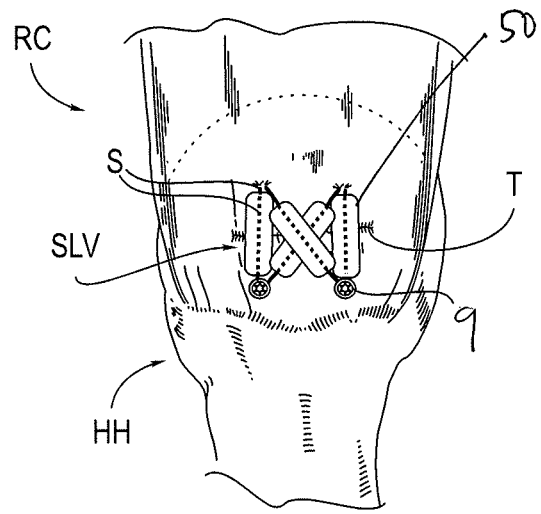
FIG. 14 is a top view of a rotator cuff repair using sutures from medial and lateral anchor rows and including four, single conduit suture guided patches to augment the repair.

FIG. 14 is a top view of a rotator cuff repair using sutures from medial and lateral anchor rows and including four, single conduit suture guided patches to augment the repair.

Figure 15:
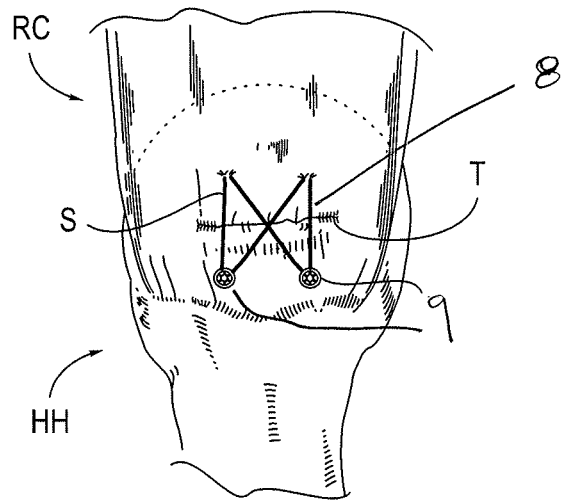
FIG. 15 is a top view of a rotator cuff repair using sutures from medial and lateral anchor rows showing the crossed suture pattern without any suture guided patches.

FIG. 15 is a top view of a rotator cuff repair using sutures from medial and lateral anchor rows showing the crossed suture pattern without any suture guided patches.

Figure 16:
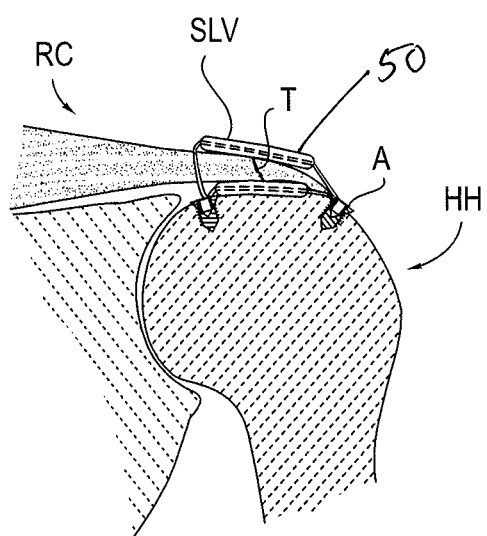
FIG. 16 is a side view of a rotator cuff repair using sutures from medial and lateral anchor rows and including single conduit suture guided patches delivered above and below the rotator cuff to augment the repair.

FIG. 16 is a side view of a rotator cuff repair using sutures from medial and lateral anchor rows and including single conduit suture guided patches delivered above and below the rotator cuff to augment the repair.

Figures 17, 18:
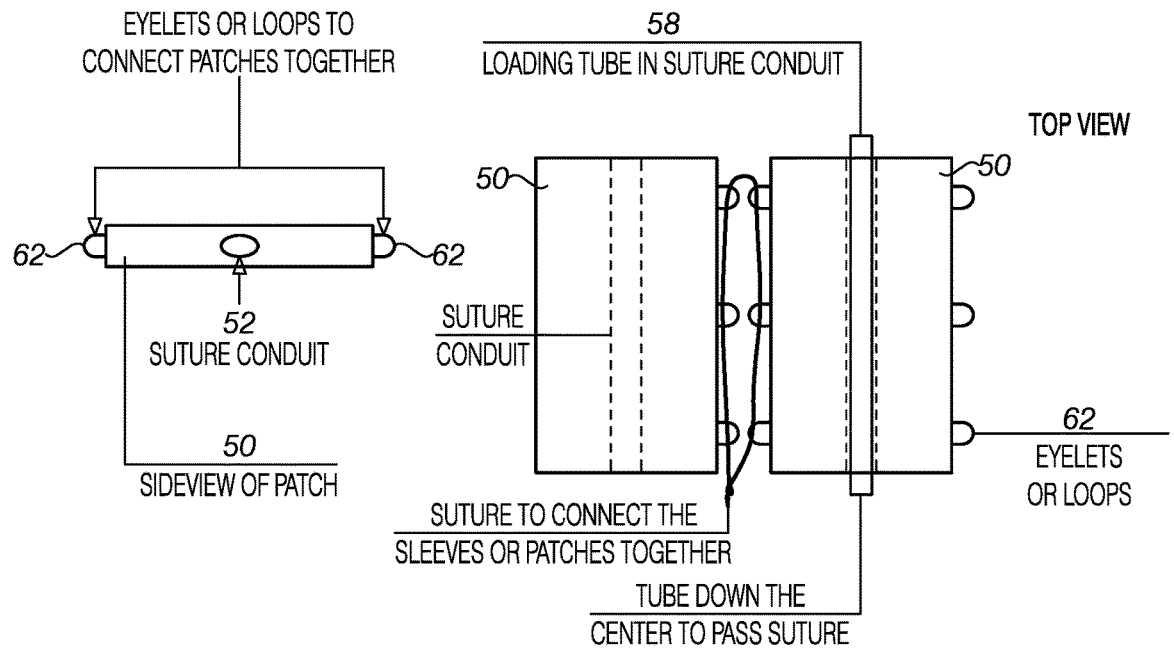
FIG. 17 is an end view of a suture guided patch having a rectangular form factor as in FIG. 9 including one or more eyelets along the sides for connecting to an adjacent suture guided patch.
FIG. 18 is a top view of two suture patches of FIG. 17 aligned side by side permitting engagement of the eyelets. Additionally, a loading tube is shown within a suture conduit of one of the patches.

Embodiments of the suture patch may be configured for being joined at the surgical site and include features for that purpose. FIG. 17 is an end view of a suture guided patch 50 having a rectangular form factor as in FIG. 9 including one or more eyelets 62 along the sides for connecting to an adjacent suture guided patch 50. FIG. 18 is a top view of two suture patches of FIG. 17 aligned side by side permitting engagement of the eyelets. Additionally, a loading tube 58 is shown within a suture conduit of one of the patches. The loading tube may be used to thread suture into a suture conduit formed within a patch or the tube may form the suture conduit or also function as a delivery tool to facilitate advancing the patch along the suture to the surgical site. One or more patches may then be arranged in the surgical site as needed. FIG. 19 is a top view of two suture patches attached to sutures between medial and lateral row anchors on a rotator cuff. The patches are shown aligned to permit side by side engagement using eyelets 62 or other structures provided for that purpose.

In still another aspect, a pair of continuous or segmented suture conduits may be arranged (i.e., aligned or diverging when viewed from proximal to distal) to provide two sides of a patch. These single conduit patches or two suture sleeves may be connected by attaching a woven scaffold or structure between and to them to be used to enhance the surgical repair of a damaged tendon to bone. As described above, the patch device can be made of biodegradable material or non-biodegradable material or a combination of the two. The device may be coated with a substance or a combination of substances thought to enhance the healing of a damaged tendon to bone as detailed in the patch delivered materials section above.

Suture Guided Patches Having Two Suture Conduits

Figure 26A:
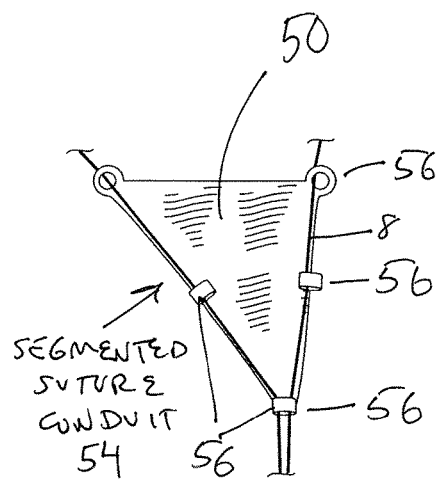
FIGS. 26A, 26B and 26C are top views of suture guided patches having overall shapes that are approximately triangular with one and wider than the other similar to the patch of FIG. 21.
Figure 26B:
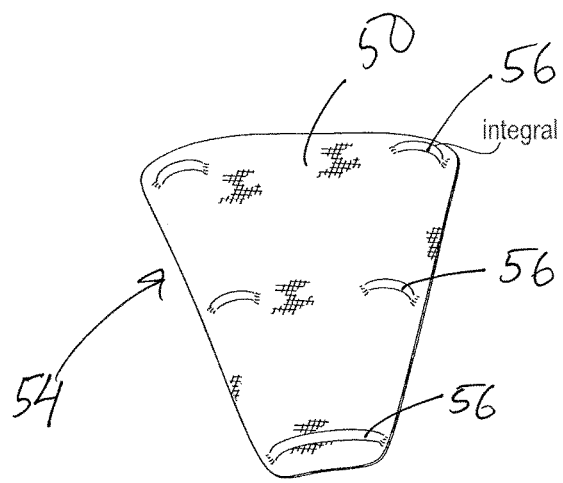
Figure 26C:
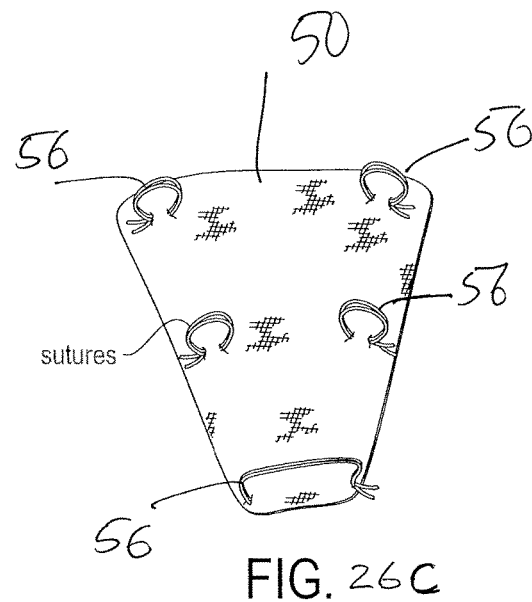

FIGS. 21 and 22 are top and side views respectively of a suture guided patch with 2 suture conduits in a generally triangular shape having a wide end and a narrow end. FIGS. 26A, 26B and 26C are top views of suture guided patches having overall shapes that are approximately triangular with one and wider than the other similar to the patch of FIG. 21. FIGS. 26A, 26B and 26C also illustrate different types of segmented suture conduits.

Figure 27:
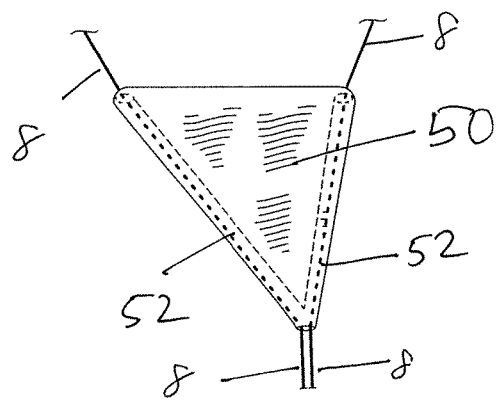
FIG. 27 is a top view of a suture guided patch having a pair of continuous suture conduits and an approximately triangular overall shape having one end wider than the other.

FIG. 27 is a top view of a suture guided patch having a pair of continuous suture conduits 52 and an approximately triangular overall shape having one end wider than the other. Segmented suture conduits 54 are shown in FIGS. 21, 22, 23, 26A, 26B, and 26C. Segmented suture conduits have a number of suture guides 56 spaced along the patch. As with previous embodiments, suture 8 is advanced from the proximal to distal end of the patch using the continuous conduit 52 or via the one or more loops 56 of a segmented conduit 54

An additional alternative embodiment includes a multi-sided device formed by joining two single conduit patches or two suture sleeves that are connected by a woven scaffold to be used to enhance the surgical repair of a damaged tendon to bone. This patch and the others above can be made of biodegradable material or non-biodegradable material or a combination of the two. The device may be coated with a substance or a combination of substances thought to enhance the healing of a damaged tendon to bone. Some examples of these substances include but are not limited to cells, growth factors and other blood products. The device may be utilized in either an arthroscopic repair or an open repair of a damaged tendon to bone. In an aspect of the embodiment of the invention, the device is used to enhance the repair of one or more rotator cuff tendon(s) in which two sutures from one or more medial anchor(s) are passed through the damaged tendon in a mattress fashion and are then passed sequentially through the two suture sleeves of the device, and finally said two sutures are secured to bone with a more laterally positioned anchor. In accordance with another aspect of the embodiment of the invention, the device is secured between one or more medially positioned and laterally positioned anchors and is used to bridge a gap during the repair of one or more damaged tendon(s) to bone. FIG. 23 is a top view of the patch of FIGS. 21 and 22 shown deployed on a rotator cuff between medial anchors and lateral anchors where the wide portion of the patch is positioned by the medial anchors.

As is illustrated in these embodiments, the suture guided patch can be configured to have a triangular shape, with one end wider than the other. Depending upon desired deployment into a surgical site, the patch may be deployed to engage with two medial anchors and a lateral anchor, or vice versa. According to the desired configuration, the patch larger end can be positioned medially and the smaller end secured laterally. The patch is configured to have either a continuous suture conduit 52 as shown in FIG. 27 or the suture conduit can be segmented 54 and be configured instead with a series of loops 56 through which the suture 8 passes. The patch can be configured to include a woven scaffold to which a suture conduit is added. As such, the patch can also be configured so that the suture 8 is threaded through the scaffold with filament loops as in FIG. 21, 22 and FIG. 26C or with thin hoops as in FIGS. 26A and 26B. As described below, there are many variations for providing suture conduits for suture guided patches.

In some embodiments, there may be provided a two pronged pusher to push the device through a cannula. The pusher or a patch positioning device may also be provided and can be shaped like a two pronged fork that is designed to push the device through an arthroscopic cannula after the suture guided patch has been loaded onto two sutures outside the body. The patch positioning device similar to the patch delivery tools described herein may be comprised of either plastic or metal and can be disposable or reusable in a surgical procedure depending on the material utilized. FIG. 24 is a top view of the patch of FIG. 21 with a two-pronged pusher tool engaged to a distal edge of the patch. FIG. 25 is a side view of the pusher tool shown in use in FIG. 24.

Exemplary Patch Method with Single Suture

FIGS. 28-32 provide an exemplary simplified example of the delivery of a suture guided patch to a surgical site of a suture based repair for a torn rotator cuff.

Figure 28:
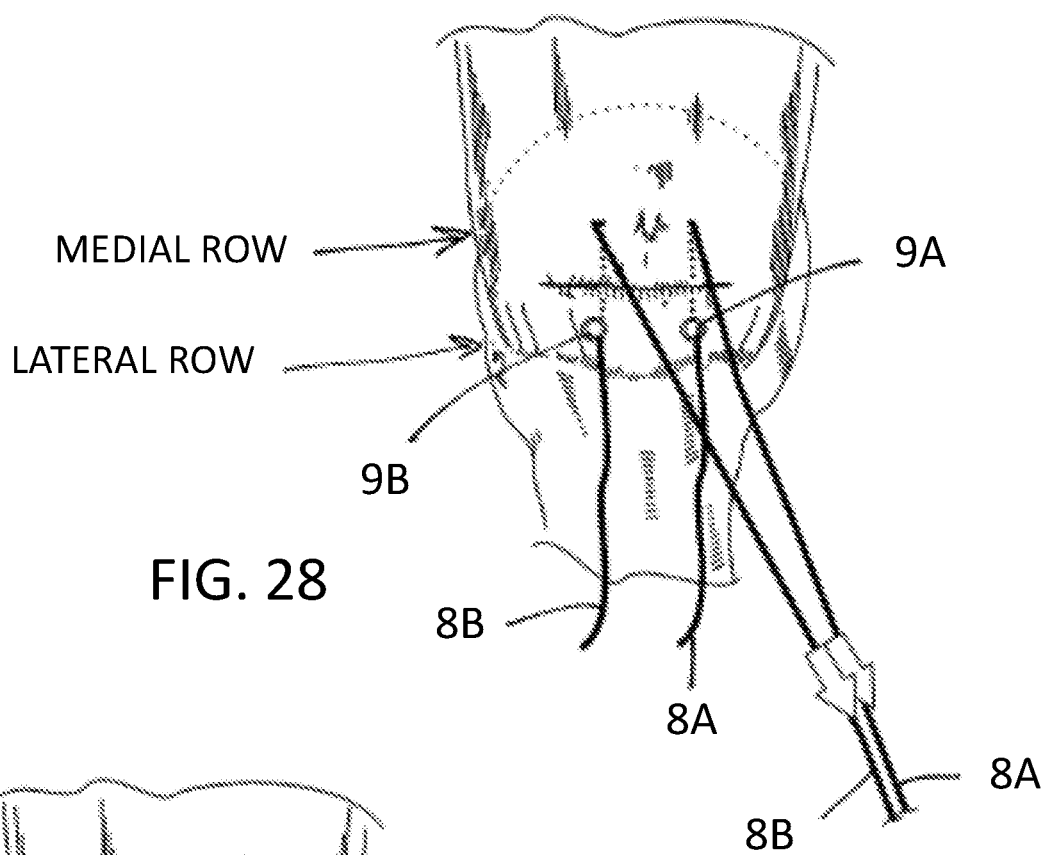
FIG. 28 illustrates a top down view of a two suture anchor repair of a rotator cuff with two sutures crossed and moved outside of the body.

FIG. 28 illustrates a top down view of a two suture anchor repair of a rotator cuff. First, two bone anchors (9A, 9B) are placed in a medial position on the greater tuberosity. In this simplified example, each anchor has suture 8 threaded through it. In this simple example, there is one strand per anchor for total of two strands. Next, both strands are then passed from underneath the rotator cuff tendon to the top of the tendon with a suture passer. These strands form a row about 1.2 cm from the cut edge of the tendon.

Figure 29:
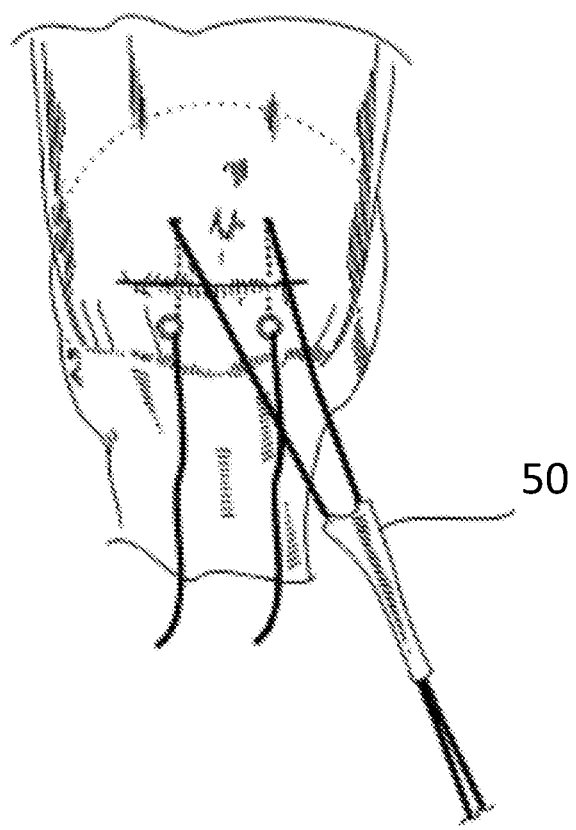
FIG. 29 is the surgical view of FIG. 28 with the two suture anchors loaded into the suture conduits of a suture guided patch with the patch being advanced towards a surgical site.

Next, as shown in FIG. 28 the strands 8A, 8B are then crossed: strand 8A from anchor 9A is paired with strand 8B from anchor 9B. After crossing, these 2 strands are brought together outside the body through a cannula with an 8 mm diameter. Next, outside of the body, these two sutures 8A, 8B are threaded through the two continuous suture conduits in a suture guided patch 50. In this embodiment, the suture patch is loaded with the widest end (here the distal end) facing towards the body (in a distal direction towards the surgical site) with the narrow portion (here the proximal portion) directed away from the body or in a proximal direction. Thereafter, as shown in FIG. 29, the patch 50 is then advanced along the two sutures 8A, 8B as the sutures move along the suture conduits. Patch advancement continues to the point where the distal end of the patch reaches the place where the sutures 8A, 8B emerge from the top surface of the rotator cuff tendon.

Figure 30:
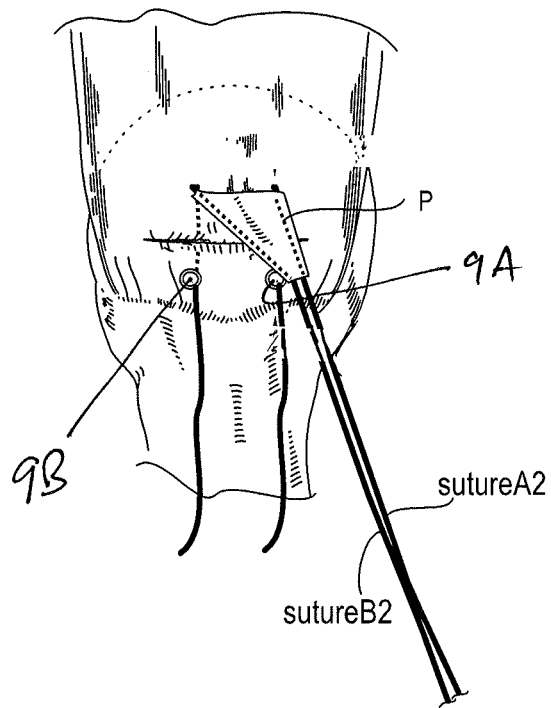
FIG. 30 is the surgical view of FIG. 29 where the distal end or widest end of the patch is positioned in the surgical site where the sutures emerge from the rotator cuff.
Figure 31:
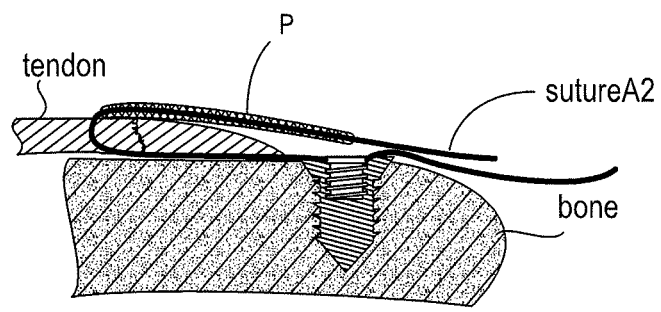
FIG. 31 is a cross section view of the patch placement within the surgical site as shown in FIG. 30.
Figure 32:
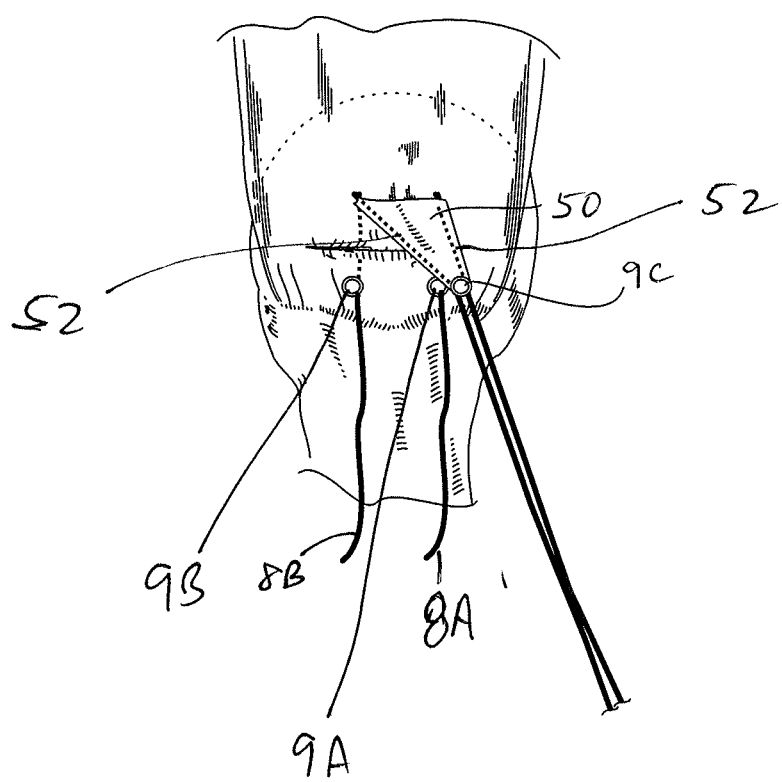
FIG. 32 illustrates a top down view of a two suture anchor repair of a rotator cuff as shown in FIG. 30 with the narrow end or the proximal end of the patch secured by anchoring the two sutures within the patch suture conduits to a third bone anchor in the greater tuberosity.

At this point, as best seen in FIGS. 30 and 31, the patch is sitting on the top surface of the rotator cuff tendon. Next, the sutures are then passed through a free anchor A3 outside the body. The anchor A3 is threaded along sutures 8A, 8B and is then inserted into the bone on the lateral aspect of the greater tuberosity as shown in FIG. 32. As appreciated by the location of the anchor A3 in FIG. 32 and the lateral edge of the patch 50 in FIG. 31, in alterative patch embodiments, a longer patch may be selected for any number of possible advantages, depending upon surgeon preference and patient needed. A longer patch may still have the same medial position but would allow the same patch position to have the patch pleated or gathered along the sutures thereby adding additional material to the site if needed or to allow more of the surgical site to be covered such as to permit additional coverage of the rotator cuff tendon or to permit anchor A3 to be positioned more laterally along the lateral aspect of the greater tuberosity. With the illustrative embodiment, the finished construct is shown in the top view of FIG. 32 as having 2 sutures holding down the medial aspect of the rotator cuff at 2 points, holding down the lateral aspect of the rotator cuff at 1 point and a triangular patch sitting on top of the cuff held in place using the 2 sutures within the provided suture conduits.

Exemplary Patch Method with Two Tail Suture

Figure 33:
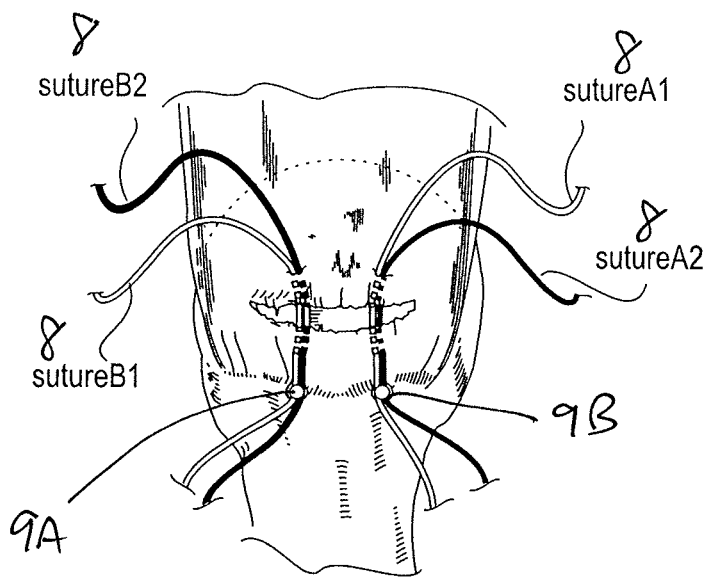
FIG. 33 is a top down view of two bone anchors placed in a medial position on the greater tuberosity each one having two sutures for a total of four stands shown having been passed from underneath the rotator cuff tendon to the top of the tendon with a suture passer.
Figure 34:
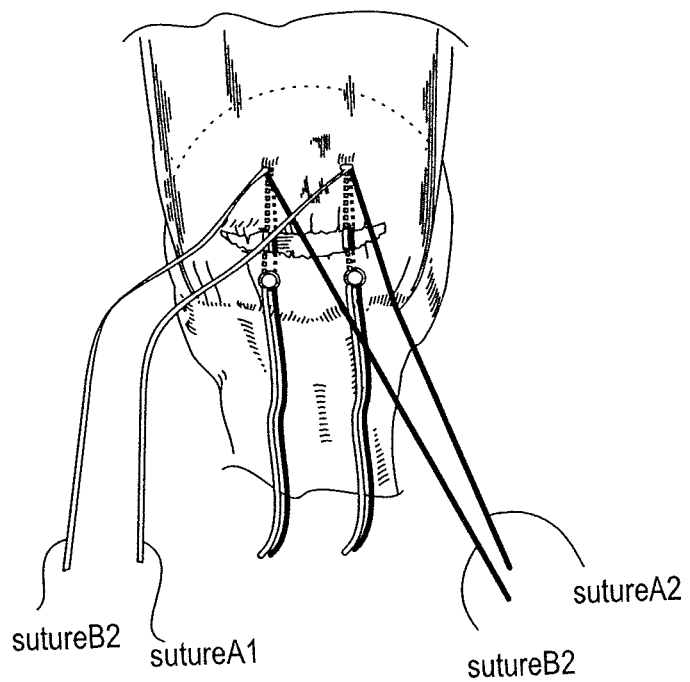
FIG. 34 illustrates a top down view of the two suture anchor repair of a rotator cuff as shown in FIG. 33 with one strand from each of the two suture anchors crossed and moved outside of the body.
Figure 35:
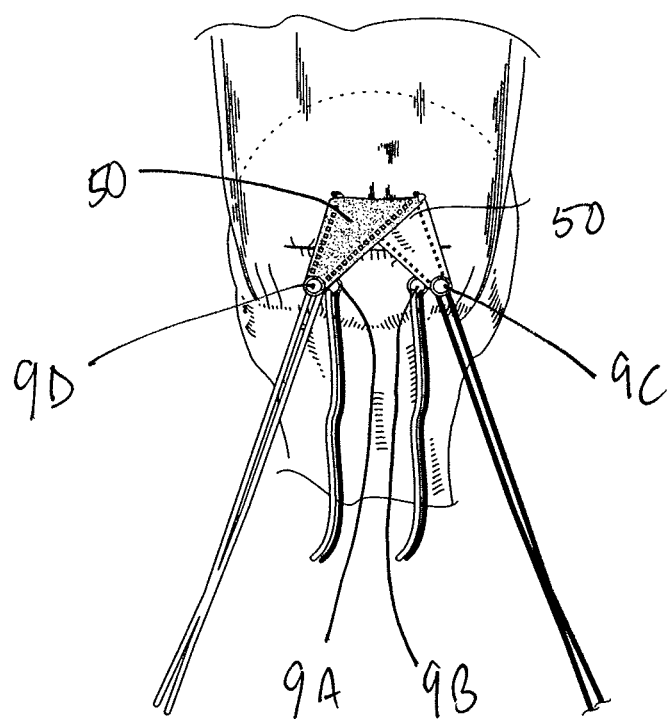
FIG. 35 illustrates a top down view of a two suture anchor repair of a rotator cuff as shown in FIG. 33 after passing two crossed sutures of the four suture strands through the suture conduits of a first patch and the remaining two crossed sutures through the suture conduits of a second patch. Both patches are shown with the narrow end or the proximal end of the patch secured by anchoring the two sutures within the patch suture conduits to a third bone anchor in the greater tuberosity.

FIGS. 33-38 illustrate a two suture anchor delivery of two suture guided patches at a surgical site for a suture based repair of a torn rotator cuff. First, two bone anchors placed in a medial position on the greater tuberosity. In this example, there are two strands per anchor for total of four strands. FIG. 33 shows the four strands after having been passed from underneath the rotator cuff tendon to the top of the tendon with a suture passer. These strands form a row about 1.2 cm from the cut edge of the tendon. Next, as shown in FIG. 34, the strands are then crossed: 1 strand from anchor A is paired with 1 strand from anchor B. As described above in FIGS. 28-32, after crossing, these 2 strands are brought together outside the body through a cannula with an 8 mm diameter. Next, outside of the body, these 2 sutures are threaded through two continuous suture conduits in a suture guided patch. In this embodiment, the suture patch is loaded with the widest end (here the distal end) facing towards the body (in a distal direction towards the surgical site) with the narrow portion (here the proximal portion) directed away from the body or in a proximal direction. Thereafter, the patch is then advanced along the two sutures as the sutures move along the suture conduits. Advancement continued to the point where the sutures emerging from the top surface of the rotator cuff tendon. At this point, the patch is sitting on the top surface of the rotator cuff tendon. Next, the sutures are then passed through the lateral row anchor and secured. The process is repeated for the other two sutures to be crossed, inserted into a patch suture conduit and delivered to the surgical site and anchored. The suture repair with two suture guided patches is shown in FIG. 36. As a result, the finished construct has sutures holding down the medial aspect of the rotator cuff at 2 points, holding down the lateral aspect of the rotator cuff at 2 points with overlapping triangular patches sitting on top of the cuff each held in place using the 2 sutures within the provided suture conduits.

Figure 37:
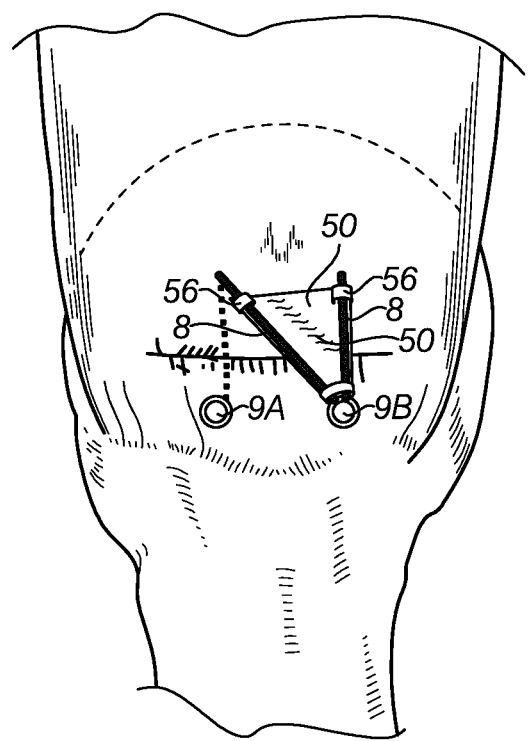
FIG. 37 is a top down view of patch cuff repair as in FIG. 36 showing an alternative suture guided patch having a segmented suture conduit and the use of a lateral anchor to secure the narrow or proximal end of the patch.

FIG. 37 is a top down view of patch cuff repair as in FIG. 36 showing an alternative suture guided patch having a segmented suture conduit and the use of a lateral anchor to secure the narrow or proximal end of the patch.

FIG. 38 is a top down view at the conclusion of the alternative suture patch repair of FIG. 37 with two suture guided patches on the rotator cuff repair. This view also illustrates the suture within the segmented suture conduits of both patches as well as the use of the lateral row anchors instead of adding third anchors as in FIG. 36.

Additional Details of Suture Guided Patches

A suture guided patch is a device used to promote healing at a suture surgical repair site. A suture guided patch has an overall shape, a proximal end and a distal end. There is at least one suture conduit along the patch sized to allow passage of a suture and permit relative movement of the patch along a suture disposed within the suture conduit. In use, when the patch is positioned to promote healing at the surgical repair site, a suture disposed within the suture conduit extends along the patch beyond the proximal end and beyond the distal end.

Suture guided patches include a general shape or form factor and at least one suture conduit. The suture conduit is aligned to the patch form factor to produce the desired orientation of the patch in the surgical site upon delivery using the sutures anchored in the surgical site. The dashed lines on each of the exemplary patches in FIGS. 39A-39D are used to show location and can indicate the position of either continuous or segmented suture conduits. A suture conduit is a continuous suture conduit if it extends from the proximal end to the distal end of the patch. In contrast, a suture conduit is a segmented suture conduit when two or more suture guide structures are spaced along the patch to align the suture disposed within the two or more suture guide structures. The suture guide structures are provided along the patch relative to the proximal end and a distal end of the patch depending on the pathway of the suture relative to the patch such as aligned or divergent.

FIG. 39A is a top view of a suture guided patch having a single suture conduit and a generally rectangular form factor.

FIG. 39B is a top view of a suture guided patch having two aligned suture conduits and a generally rectangular form factor. FIG. 39C is a top view of a suture guided patch having two aligned suture conduits and a generally rectangular form factor where the spacing of the suture conduits is selected to coincide with the spacing of two suture anchors. The exemplary suture guided patches of FIGS. 39B and 39C illustrate aligned suture conduits because the suture conduits are about the same spacing at the proximal end of the patch as at the distal end of the patch.

FIG. 39D is a top view of a triangular shaped suture guided patch having two suture conduits generally aligned with two sides of the triangle. The suture conduits in FIG. 39D are divergent suture conduits because the suture conduits are closer at the narrow end of the patch (proximal end) and further apart at the wider end (distal end). Divergent suture conduits have different spacing at the proximal and distal ends of a suture guided patch.

Figure 40A:
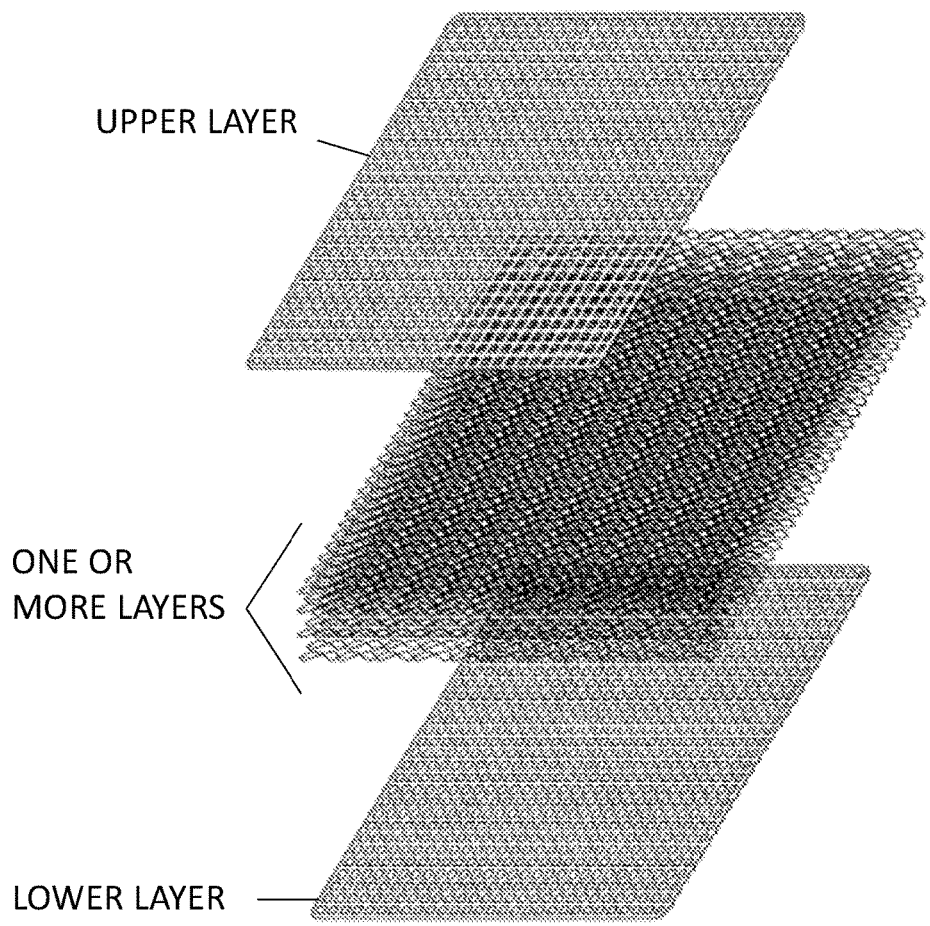
FIG. 40A is an exploded view of a suture guided patch having an upper layer and a lower layer with several layers of material between the upper and the lower layer.
Figure 40B:
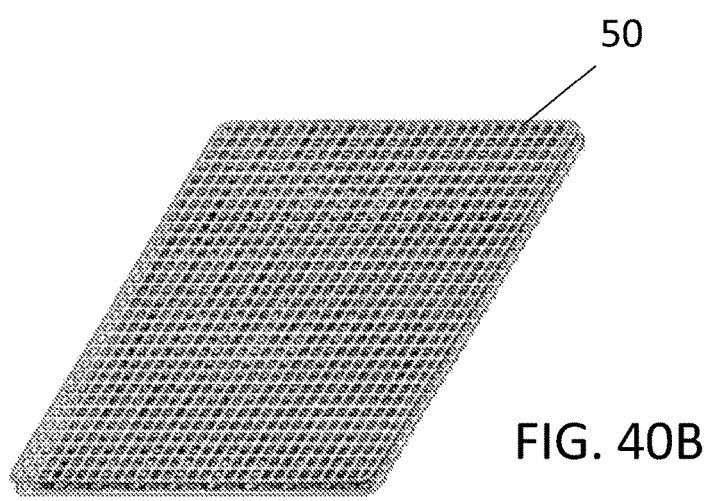
FIG. 40B is a perspective view of the layers of FIG. 40A assembled into a structure suited for use as a suture guided patch.

Construction of various suture patches including multiple layers, stacks, and sandwich structures may be appreciated with reference to FIGS. 40A and 40B. FIG. 40A is an exploded view of a suture guided patch having an upper layer and a lower layer with several layers of material between the upper and the lower layer. The various layers may include one or more layers of a non-woven mesh, a woven mesh or a knitted multifilament mesh. The various structures and arrangements of the components of the patch are made from materials that are bioabsorbable. In some embodiments, the patch is constructed of a biodegradable material having a hybrid of a porous material and a material that provide strength construct. One exemplary construction of the patch is formed from a PLA or PGA mesh and strips of PLA or PGA are provided for support.

FIG. 40B is a perspective view of the layers of FIG. 40A assembled into a structure suited for use as a suture guided patch. In some embodiments, a suture guided patch comprises two or more layers of material. The suture guided patch may be configured to deliver a suture delivered material in a wide variety of constructions. In one aspect, a portion of the patch folded into a plurality of pleats. In some embodiments, when the patch is deployed into the surgical site at least a portion of the plurality pleats remain. In some suture guided patch embodiments, the patch includes a scaffold sandwiched between outer layers of a non-woven mesh, a woven mesh or a knitted multifilament mesh. The one or more layers of the patch are assembled or joined into a unitary structure using a variety of suitable processes for the types of materials used. The materials or layers in a patch may be assembled by stitching the layers together with fibers, bioabsorbable fibers, or suture, or by joined together by cementing, bonding, embroidering or by thermal processing such as sealing or welding.

In one embodiment, the suture guided patch is configured for designed release of a patch delivery material. In one embodiment, at least one of the two or more layers of material is selected to carry a patch delivery material. The patch delivery material for a specific suture guided patch is selected to promote a desired interaction including an onset, an increase, a decrease or a cessation of a related therapeutic, pharmacodynamic, biologic or other effect upon release at the surgical repair site. In some configurations, when the patch is in position at the suture surgical repair site the layer selected to carry a patch delivery material is directly adjacent to the repair site. In some other configurations, when the patch is in position at the suture surgical repair site the layer selected to carry a patch delivery material is separated from the surgical repair site by another of the two or more layers of the patch. In various different configurations, a suture guided patch has an upper layer and a lower layer and a layer between the upper layer and the lower layer, wherein one or more of the upper layer, the lower layer and the layer between the upper layer and the lower layer is configured to maintain a patch delivery material according to a selected designed time release of the patch delivery material.

Figure 41A:
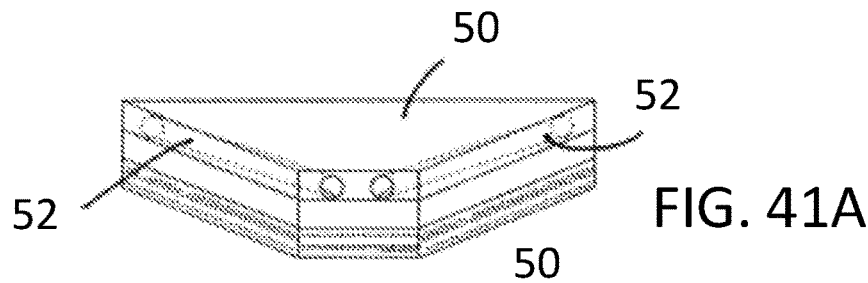
FIGS. 41A, 41B, 41C and 41D are perspective end views of a multiple layer suture guided patch each one having a pair of continuous suture channels in a different layer of the multiple layer structure.
Figure 41B:
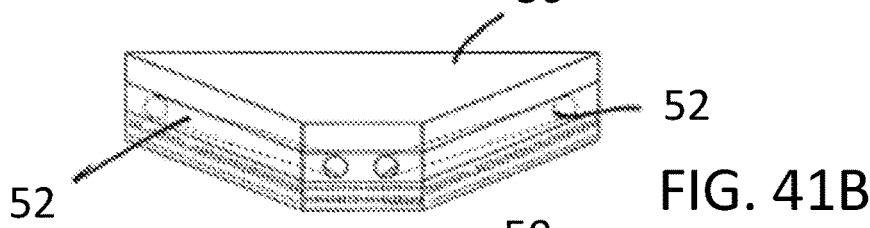
Figure 41C:
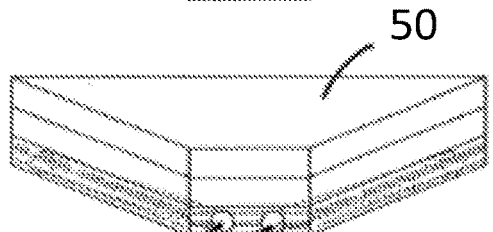
Figure 42A:
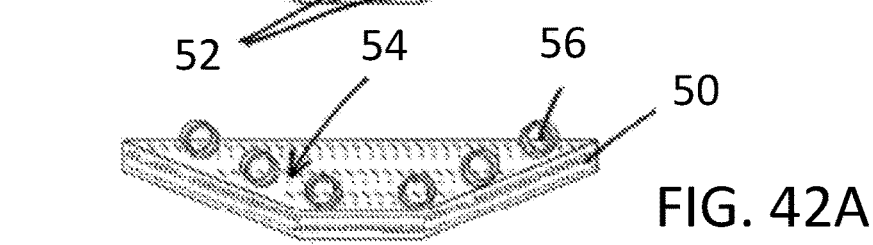
FIGS. 42A-42E illustrate perspective end views of a suture guided patch each illustrating the location and type of different segmented suture conduits.
Figure 42B:
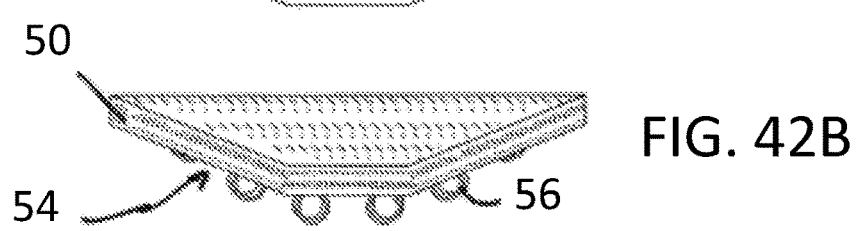
Figure 42C:
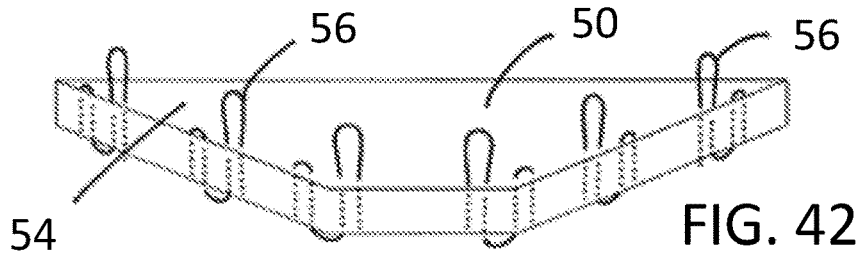
Figure 42E:
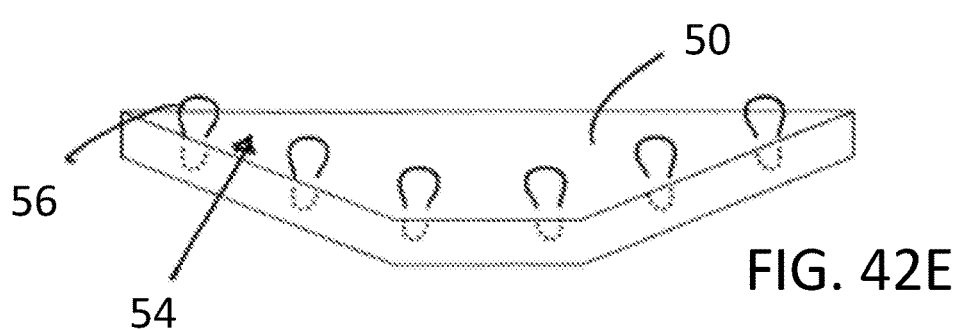
Figure 41D:
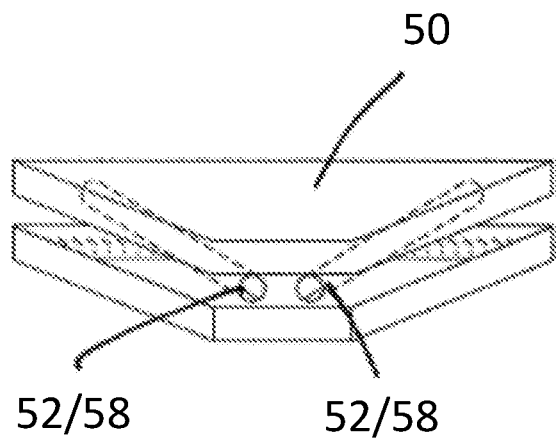
Figure 42D:
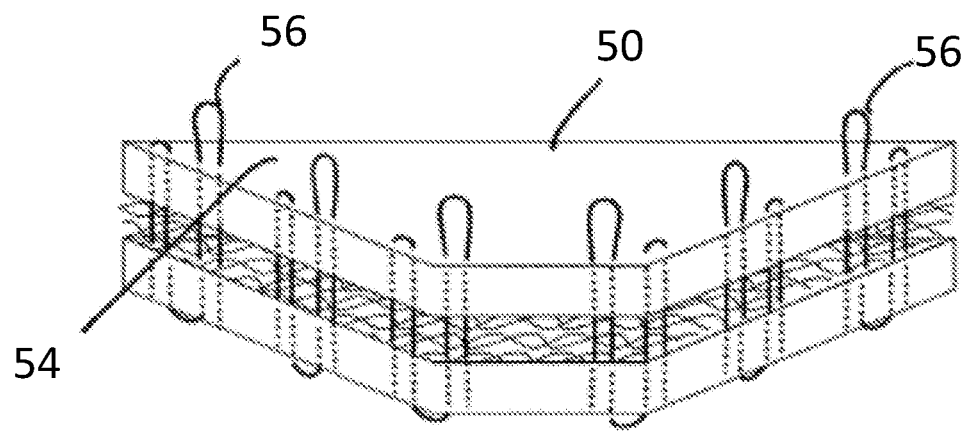

The one or more suture conduits of a suture guided patch may be provided in a number of different arrangements depending upon the particular patch design implemented. A number of different aspects of the various alternative configurations of a four sided suture guided patch are appreciated with reference to FIGS. 41A-42E. Suture conduits may be continuous as shown in FIGS. 41A-41D or segmented as in FIGS. 42A-42E. The segmented conduits of FIGS. 42A, 42C and 42D and 42E also illustrate a suture conduit extending along an outer surface of the patch. Additionally, one or more suture conduits may be provided on, in or within an upper layer as shown in FIGS. 41A, 42A, 42C, 42D and 42E. In other embodiments, one of more suture conduits may be provided on, in or within the lower layer as shown in FIGS. 41C and 42B. In other embodiments, one of more suture conduits may be provided on, in or within a layer between the upper layer and the lower layer as shown in FIGS. 41B and 41D. In some embodiments, the suture conduit is provided from a loop or portion of material used to secure together the various layers of material as in FIGS. 42C and 42D. Alternatively, loops of material or structure may be added to a patch to form suture conduit guides as shown in FIGS. 42A, and 42B.

Figure 43A:
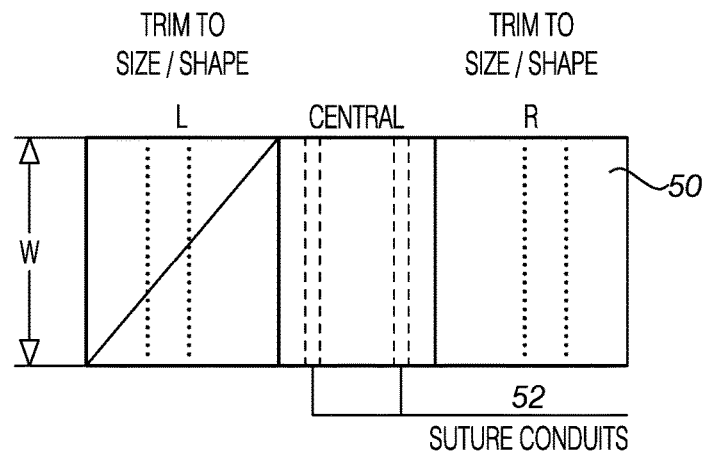
FIG. 43A illustrates a top down view of a suture guided patch for use in the process of FIG. 74 to select and process a patch before delivery to the surgical site.
Figures 43B, 43C, 43D:
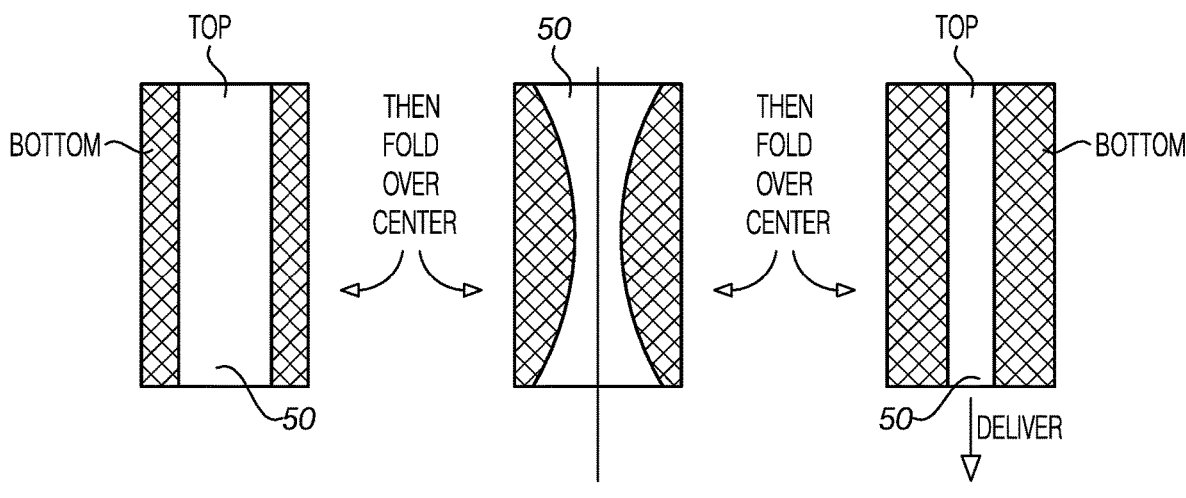
FIGS. 43B, 43C and 43D illustrate top views of different trimming, shaping and folding operations on the patch of FIG. 43A.

Additional aspects of suture guided patches may be appreciated by reference to FIGS. 43A-46. FIG. 43A illustrates a top down view of a suture guided patch for use in the process of FIG. 74 to select and process a patch before delivery to the surgical site. FIGS. 43B, 43C and 43D illustrate top views of different trimming, shaping and folding operations on the patch of FIG. 43A. FIG. 43B has rectangular edges folded on the left and the right sides of the patch. FIG. 43C has a patch that has been trimmed to have rounded flaps. This patch is also shown with a delivery tool—such as the two prong tool described above—that may be used to unfold and adjust the position of sized, trimmed or folded patches upon delivery to the surgical site. FIG. 43D is another variation of a trimmed and folded patch.

Figures 43E, 43F:
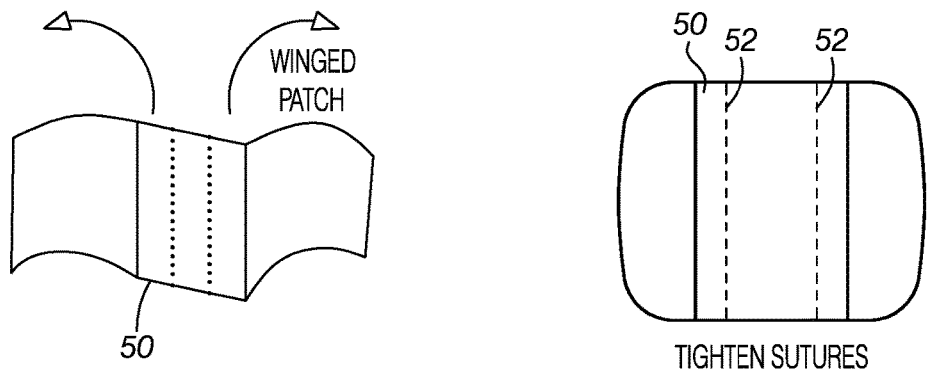
FIG. 43E is a perspective view of a folded patch being unfolded at the surgical site.
FIG. 43F is a top down view of deployed patch that had been previously trimmed and sized prior to deployment to a surgical site.

FIG. 43E is a perspective view of a folded patch being unfolded at the surgical site showing how any folded panels or sides are unfolded in order so that the patch is not damaged.

FIG. 43F is a top down view of deployed patch that had been previously trimmed and sized prior to deployment to a surgical site.

Figure 44:
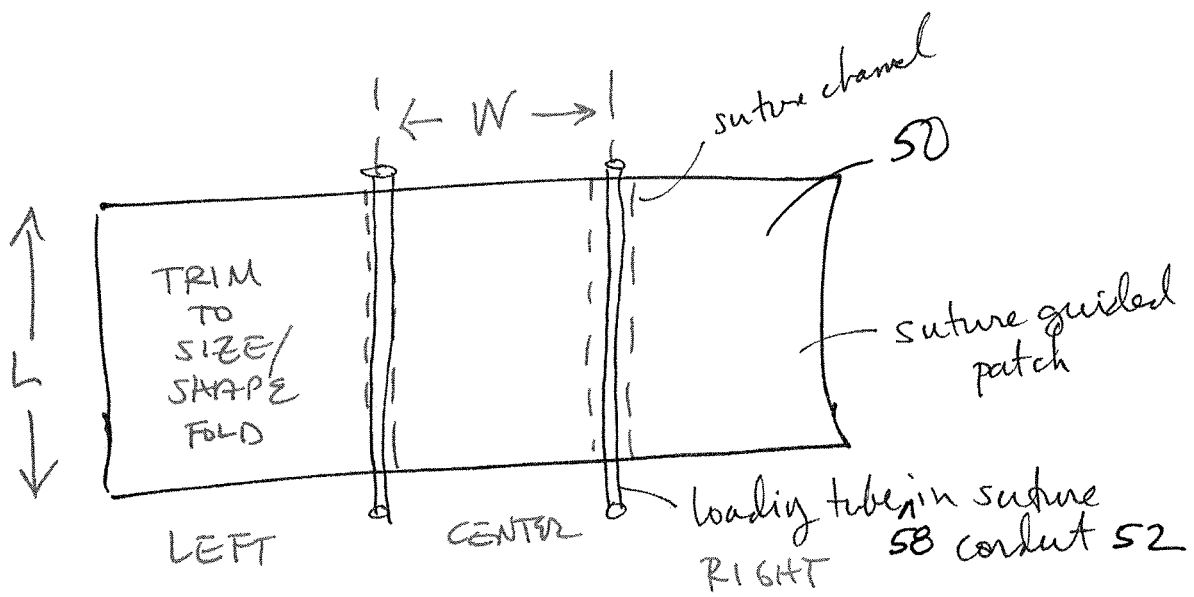
FIGS. 44, 45 and 46 illustrate top down views of patches having centrally positioned suture conduits for a selection of aligned, divergent or either aligned or divergent suture conduits, respectively.
Figure 45:
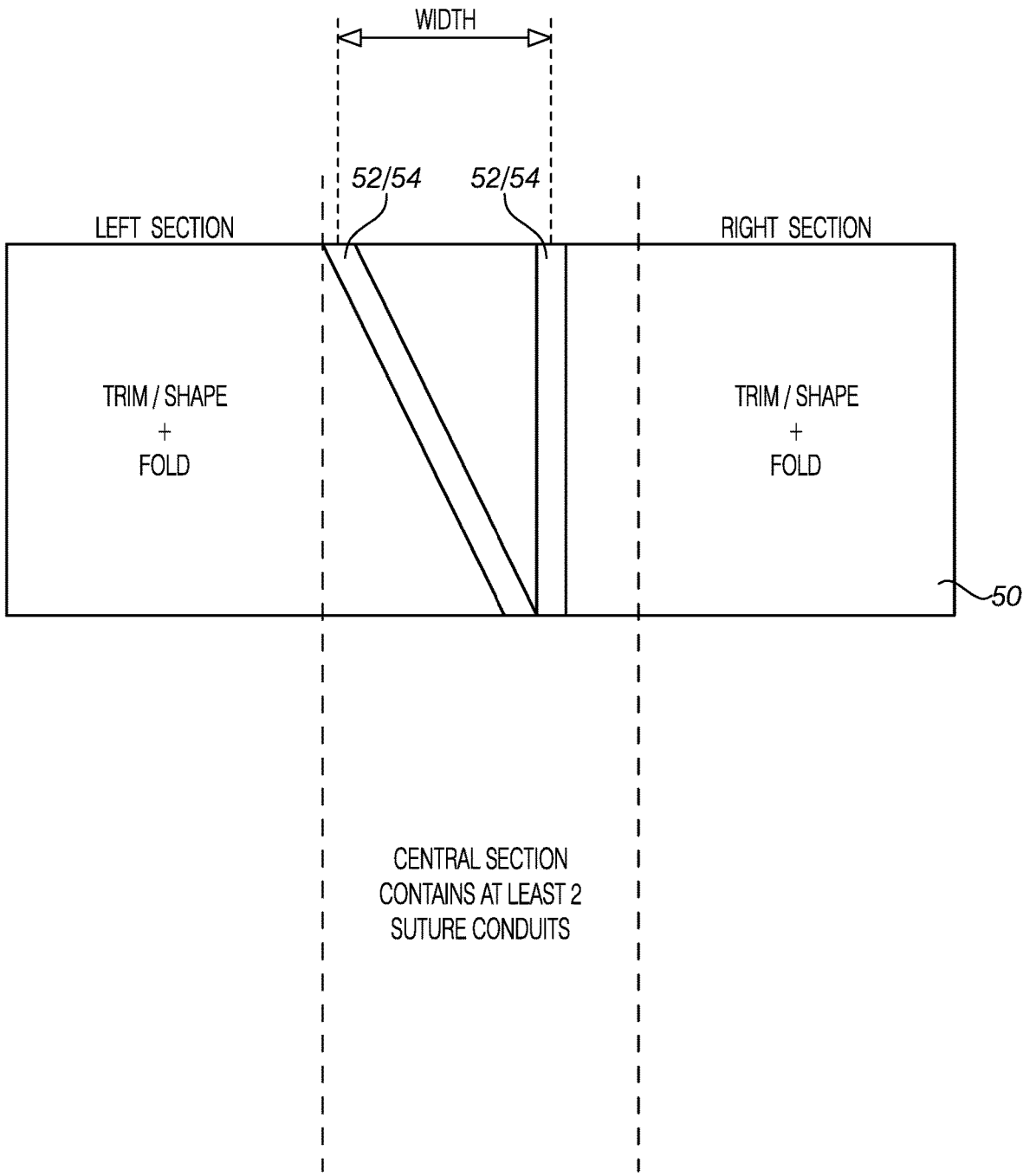
Figure 46:
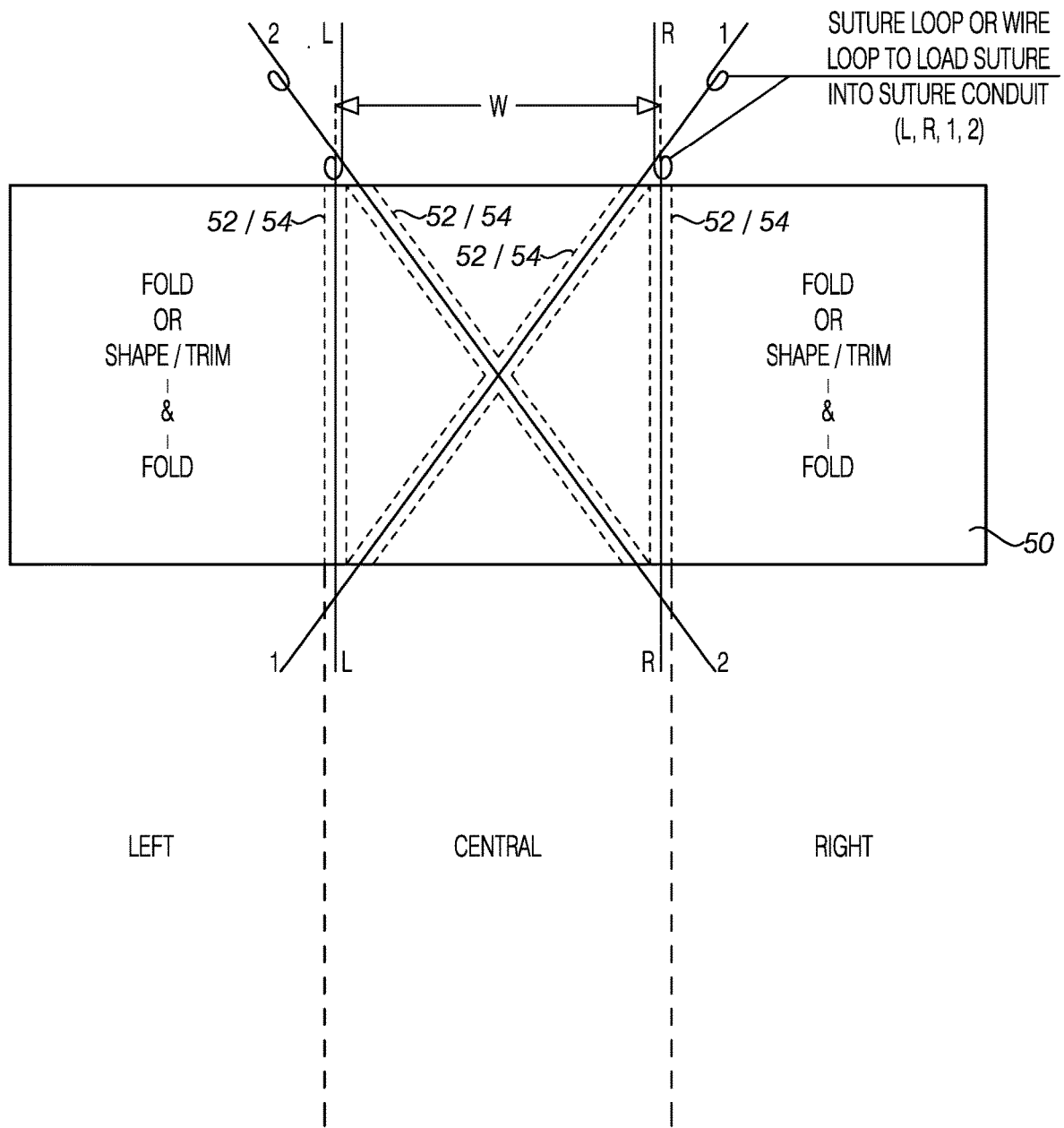

Align the same lines as FIG. 43A, FIGS. 44, 45 and 46 illustrate top down views of patches that may be trimmed, sized or shaped based on surgeon preference or patient need. Each of these embodiments illustrates having centrally positioned suture conduits. Other placements of the suture conduits along the left or the right sections may be useful for some specific embodiments, anatomical sites or anchor positions. FIG. 44 is a rectangular patch having aligned suture conduits. FIG. 44 also shows loading tubes in place within the suture conduits to quickly load the sutures into the conduits. Additionally, the tubes are shown oversized so that the loading tube can be cut in place during any timing, shaping or sizing operations. FIG. 45 illustrates a similar patch suited for trimming, sizing or shaping. This illustrative embodiment includes divergent suture conduits. Divergent conduits are suited to crossed suture delivery as described above. FIG. 46 illustrates a hybrid patch design. This patch has a size selected for any desired shaping, sizing or trimming operations. Additionally, this patch includes both aligned and divergent suture conduits. In use the suture loading wires may be used to pull the sutures into the desired suture conduit orientation. The other unused suture pulls may be removed.

Exemplary Suture Guided Patch Delivery Tools

FIGS. 47A-67 illustrate the details of the design and use of various exemplary suture patch delivery tools and devices. A number of different delivery tools may be utilized to assist in the delivery of the various embodiments of the suture guided patch. In one aspect, the sutures are loaded into a continuous suture conduit that is either part of the patch or is provided by a separate loading tube inserted into the patch. In either case, the suture remains within the patch after delivery: within the suture conduit of one and within the aperture formed by the loading tool in the other. In either of these examples, a push rod with a distal end adapted to engage a distal portion of the patch may be provided. One example is the two pronged fork described above. Additionally, the end of the push rod may be adapted for engagement with a pocket or receiver in the edge of the patch.

Other delivery tool configurations are also provided to facilitate the advancement of the patch along the sutures. In addition, as patches are devised for using in the delivery methods described herein having stowed and deployed configurations, embodiments of the delivery tool provide additional movement needed to aid some patch embodiments in the transition to the deployed condition. Some patch embodiments will transition by virtue of the divergent travel path towards the anchors and still others will move at least partially upon exiting the reduced diameter of a working channel of a scope or a delivery tool. The ability of the patch to transition from stowed to deployed will vary depending upon a number of factors such as the materials and structures used to construct the patch as well as the behavior of the patch once the patch delivered material is incorporated and prepared for use. A layer may be added to portions of the patch to permit folding and limit adhesion of the patch.

In some embodiments, a suture guided patch is provided in a loading cartridge. Suture loading elements such as looped lines or rods or may be inserted into the suture conduits to permit loading the patch onto the sutures while remaining in the loading cartridge. The cartridge may hold the patch in a stowed condition or otherwise position the patch within the cartridge to receive or incorporate or activate, as needed, a patch delivered material. The cartridge may be a separate component that is part of a delivery tool, or a separate component. FIG. 47B shows a loading cartridge embodiment coupled to a patch delivery tool. The cartridge provides one or more loading ports as suited to the introduction of a patch delivered material. Additionally, the cartridge may be adapted to hold the patch in a desired orientation or position or condition to enable loading of biologic materials or other agents requiring specific loading techniques.

The various embodiments that follow provide details of exemplary moveable leg patch delivery tools for delivering one or more suture guided patches to a surgical site. The step of loading a suture guided patch onto a movable leg patch delivery device will vary but each ensures that the patch and the tool may be advanced along the sutures to the surgical site. As a result, the sutures are loaded into a patch suture conduit and in position for use with the patch delivery device. Once appropriately loaded, the patch may be advanced along the one or more sutures towards the surgical site with the assistance of the delivery tool. After removal of the tool, the sutures remain within one or more suture conduits of the patch.

Additionally, depending upon the embodiment of the delivery device, the movement of the patch from the stowed condition is produced at least in part by the separation of the moveable legs. The legs may be biased or provided with flexible joints for this purpose. Additionally or optionally, the delivery device legs may include flexible sections positioned proximal to the patch loading position that permit the distal portions of the legs to separate as the tool and patch are advanced along the sutures. The amount of flexibility in the delivery device legs may be selected based on the amount of movement desired for a patch deployment or to allow movement in response to the suture pathway towards spaced apart anchors. In some embodiments, the delivery tool may be used for positioning the deployed patch within the surgical repair site. Once the use of the patch delivery device is completed, the device is removed from the surgical site.

In some embodiments the delivery tool may separate upon removal or may be removed as a single unit. If the delivery tool does not separate on removal, the delivery tool is removed from the surgical site by withdrawing it from the surgical site with one or more sutures remaining within the one or more suture conduits of the patch. If, the delivery tool does separate for removal, then the user will remove components of the delivery tool in sequence from the surgical repair site. At the conclusion of the sequence one or more sutures will be left remaining within the one or more suture conduits of the patch. Finally, if a positioning rod is provided or used during the patch deployment process, then the positioning rod is also removed from the surgical site.

Figure 73:
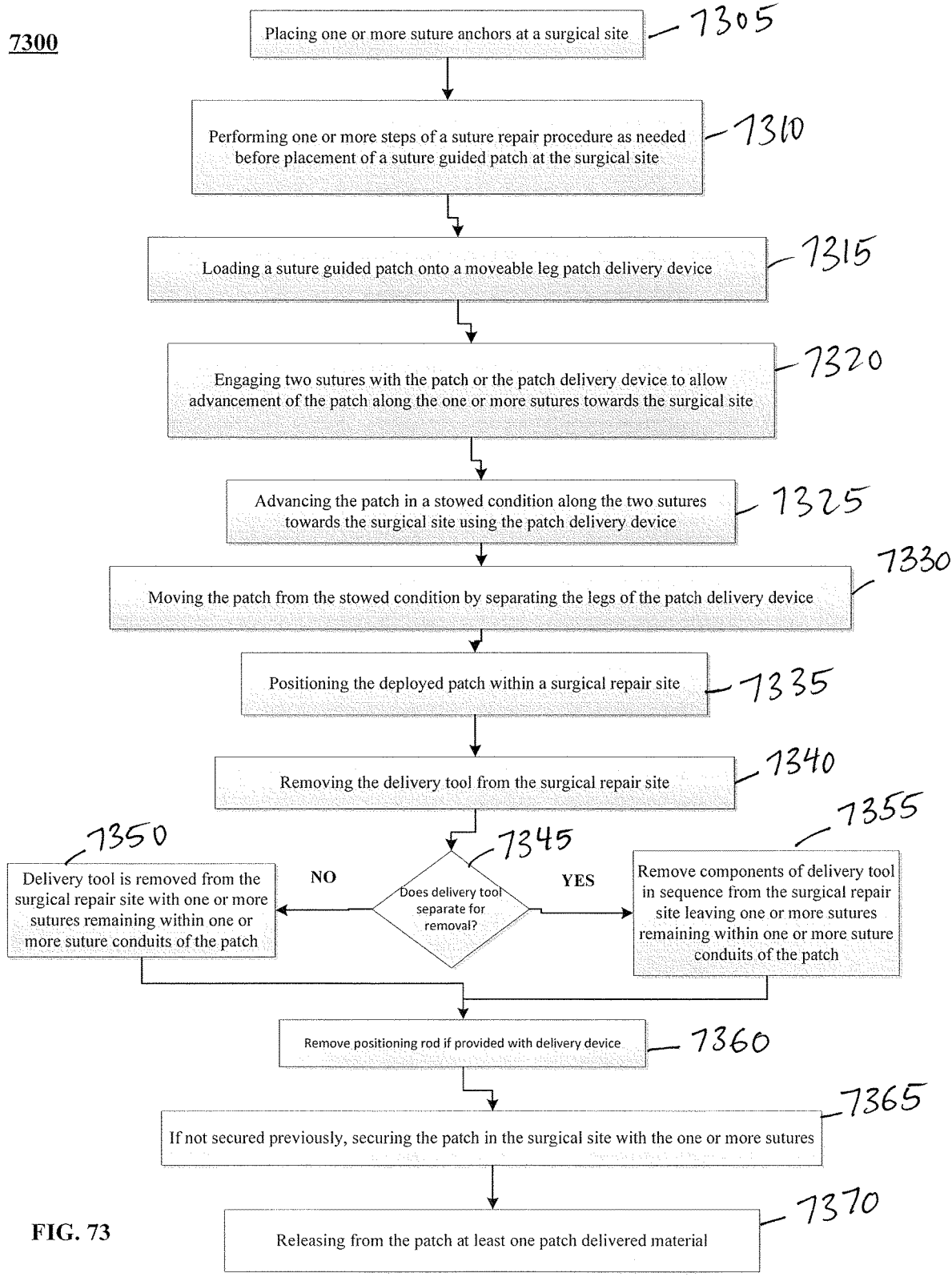
FIG. 73 is a flow chart of an exemplary surgical method for the use of an exemplary moveable leg patch delivery tool for delivering a suture guided patch to a surgical site.

The use of the delivery tool may be appreciated with reference to the various suture guided patch deployment methods as described in FIGS. 14, 16, and 28-38 above. In addition, the use of patch delivery tools may be better appreciated with reference to FIG. 73. FIG. 73 is a flow chart of a method 7300 of an exemplary surgical method using an exemplary moveable leg patch delivery tool.

Figure 47A:
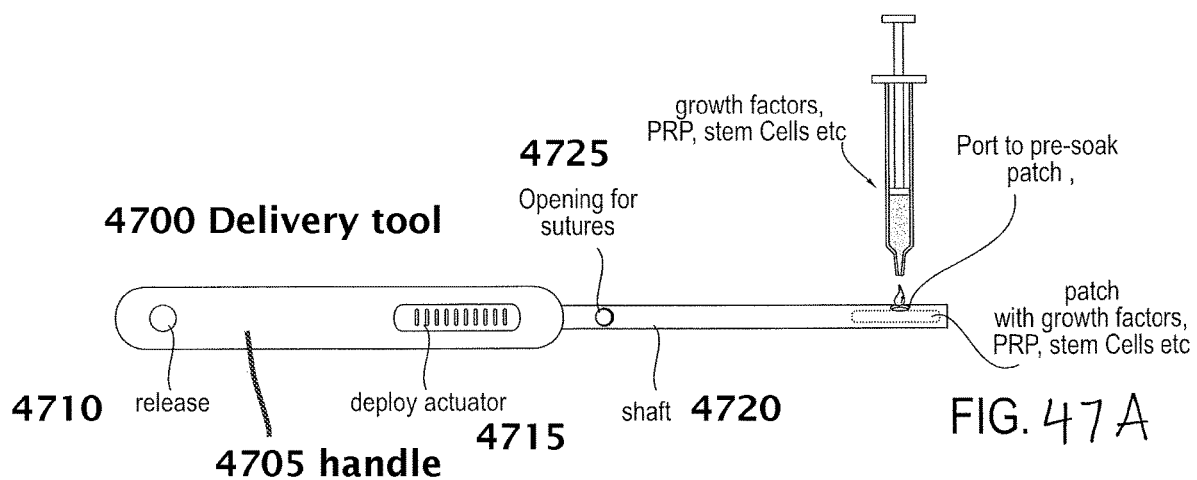
FIG. 47A is a top view of a suture patch delivery tool having a handle and an arm projecting from the handle a patch loaded into the distal end. This view also shows the addition of one or more patch delivered materials via a port in the distal end of the tool.
Figure 47B:
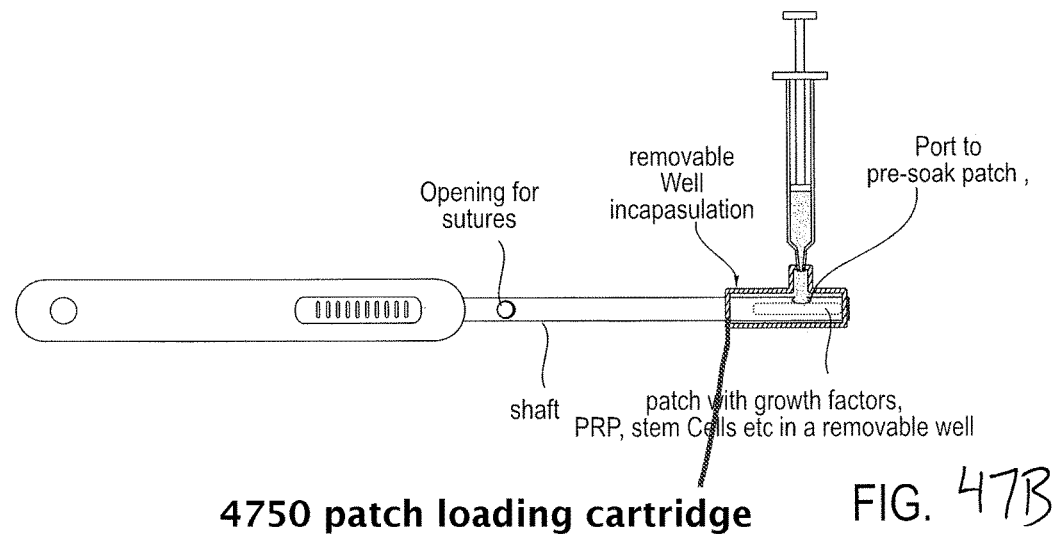
FIG. 47B is a top view of the suture patch delivery tool of FIG. 47A with a patch within a loading cartridge coupled to the patch delivery tool This view also shows the addition of one or more patch delivered materials via a port in the loading cartridge.

FIG. 47A is a top view of a suture patch delivery tool having a handle and an arm projecting from the handle a patch loaded into the distal end. This view also shows the addition of one or more patch delivered materials via a port in the distal end of the tool.

FIG. 47B is a top view of the suture patch delivery tool of FIG. 47A with a patch within a loading cartridge coupled to the patch delivery tool This view also shows the addition of one or more patch delivered materials via a port in the loading cartridge.

Figure 48A:
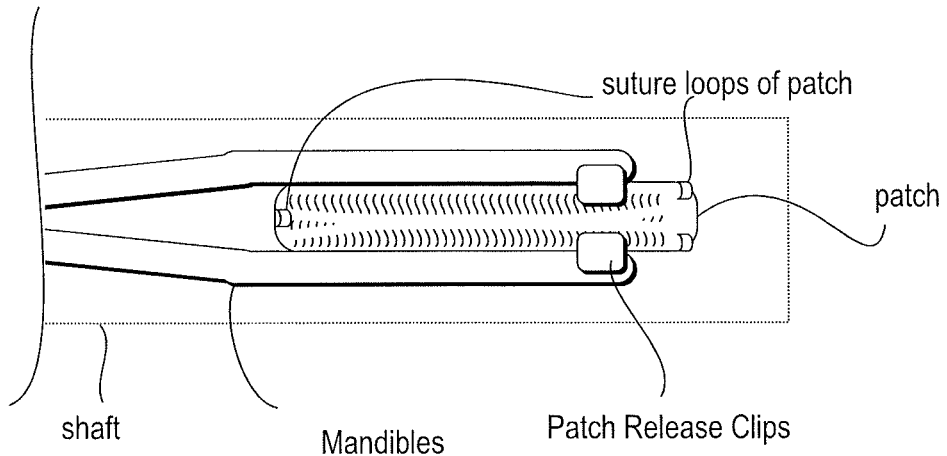
FIG. 48A is a top view of a pincer like mandible or patch release clips at the end of each of the arms engaged with a suture guided patch. Also shown in this view of the stowed patch are three suture loops one at the proximal end and two at the distal end.

FIG. 48A is a top view of a pincer like mandible or patch release clips at the end of each of the arms engaged with a suture guided patch. Also shown in this view of the stowed patch are three suture loops one at the proximal end and two at the distal end.

Figure 48B:
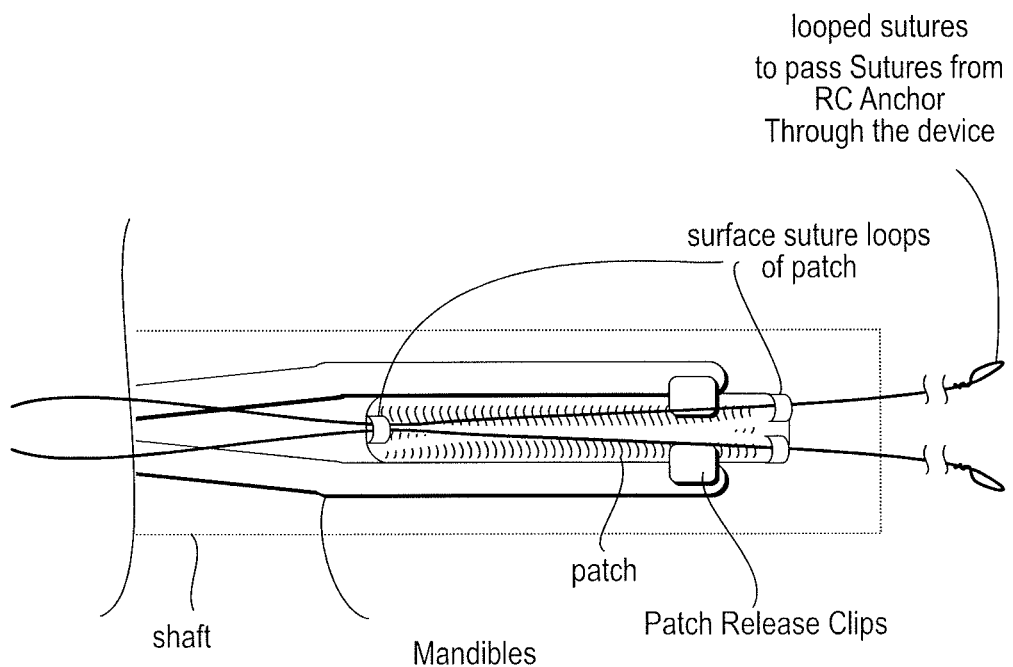
FIG. 48B is a top view of the delivery tool and stowed patch of FIG. 48A showing looped sutures threaded through each of the suture loops.

FIG. 48B is a top view of the delivery tool and stowed patch of FIG. 48A showing looped sutures threaded through each of the suture loops.

Figure 49:
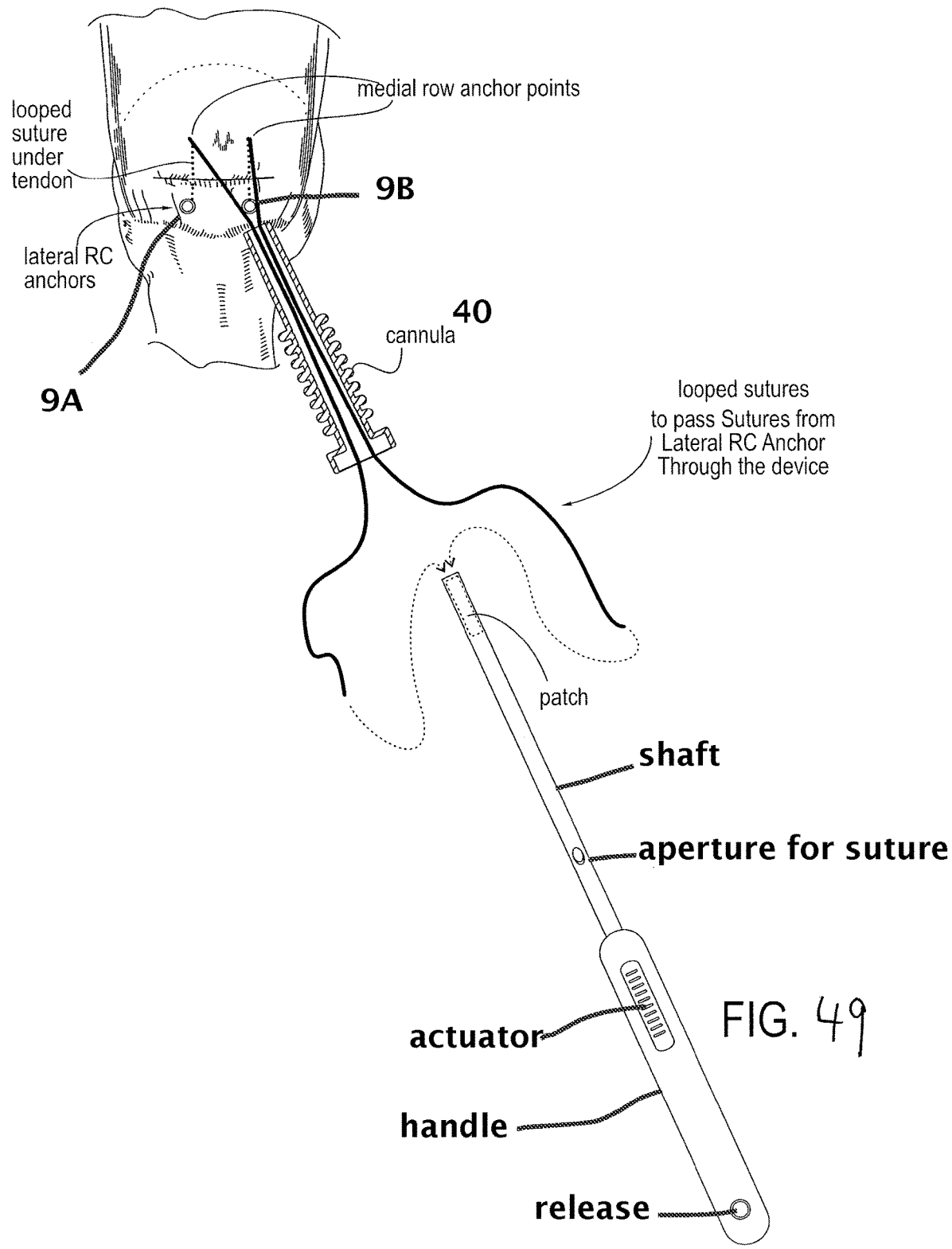
FIG. 49 is a top view of the exemplary surgical site of FIG. 29 with the crossed sutures passed outside the body and ready for loading into the delivery tool using the looped sutures of FIG. 48B.

FIG. 49 is a top view of the exemplary surgical site of FIG. 29 with the crossed sutures passed outside the body and ready for loading into the delivery tool using the looped sutures of FIG. 48B.

Figure 50:
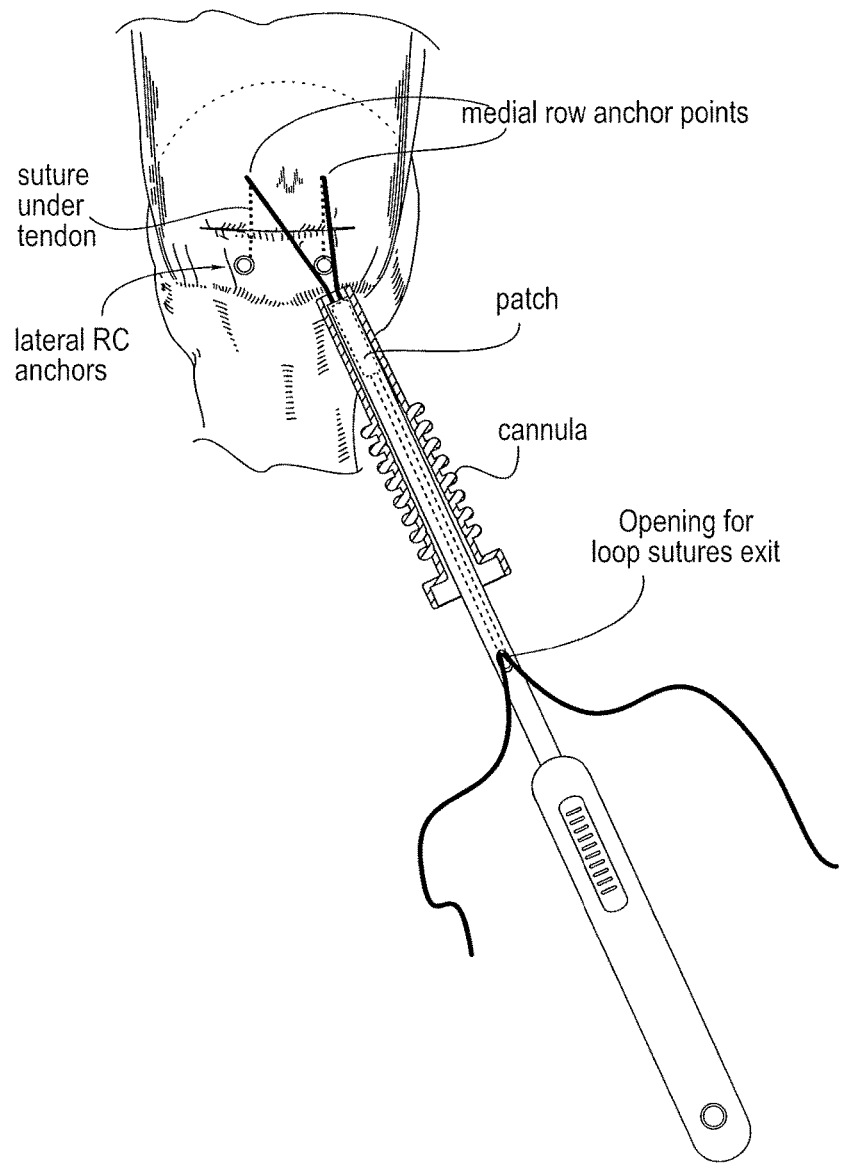
FIG. 50 is a top view of the surgical site of FIG. 49 with the crossed sutures passed outside the delivery tool and the delivery tool used to advance the patch delivery tool and the patch distally towards the surgical site and just prior to the tool and patch exiting the working channel.

FIG. 50 is a top view of the surgical site of FIG. 49 with the crossed sutures passed outside the delivery tool and the delivery tool used to advance the patch delivery tool and the patch distally towards the surgical site and just prior to the tool and patch exiting the working channel.

Figure 51:
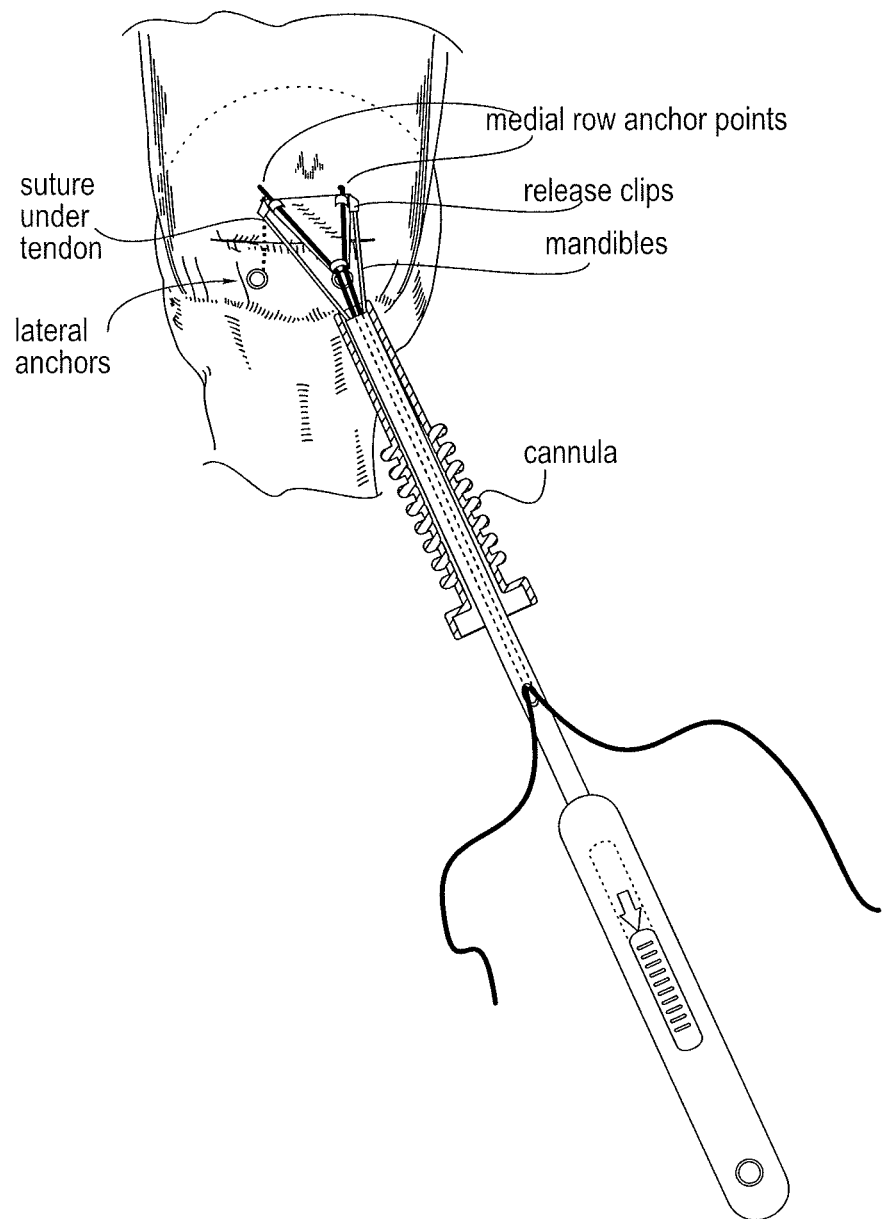
FIG. 51 is a top view of the surgical site of FIG. 50 after the patch and delivery tool have been advanced beyond the working channel by operation of the deploy actuator. Operation of the deploy actuator moved the patch and the tool along the sutures to position the distal end of the patch at the medial anchors as in FIG. 30.

FIG. 51 is a top view of the surgical site of FIG. 50 after the patch and delivery tool have been advanced beyond the working channel by operation of the deploy actuator. Operation of the deploy actuator moved the patch and the tool along the sutures to position the distal end of the patch at the medial anchors as in FIG. 30.

Figure 52:
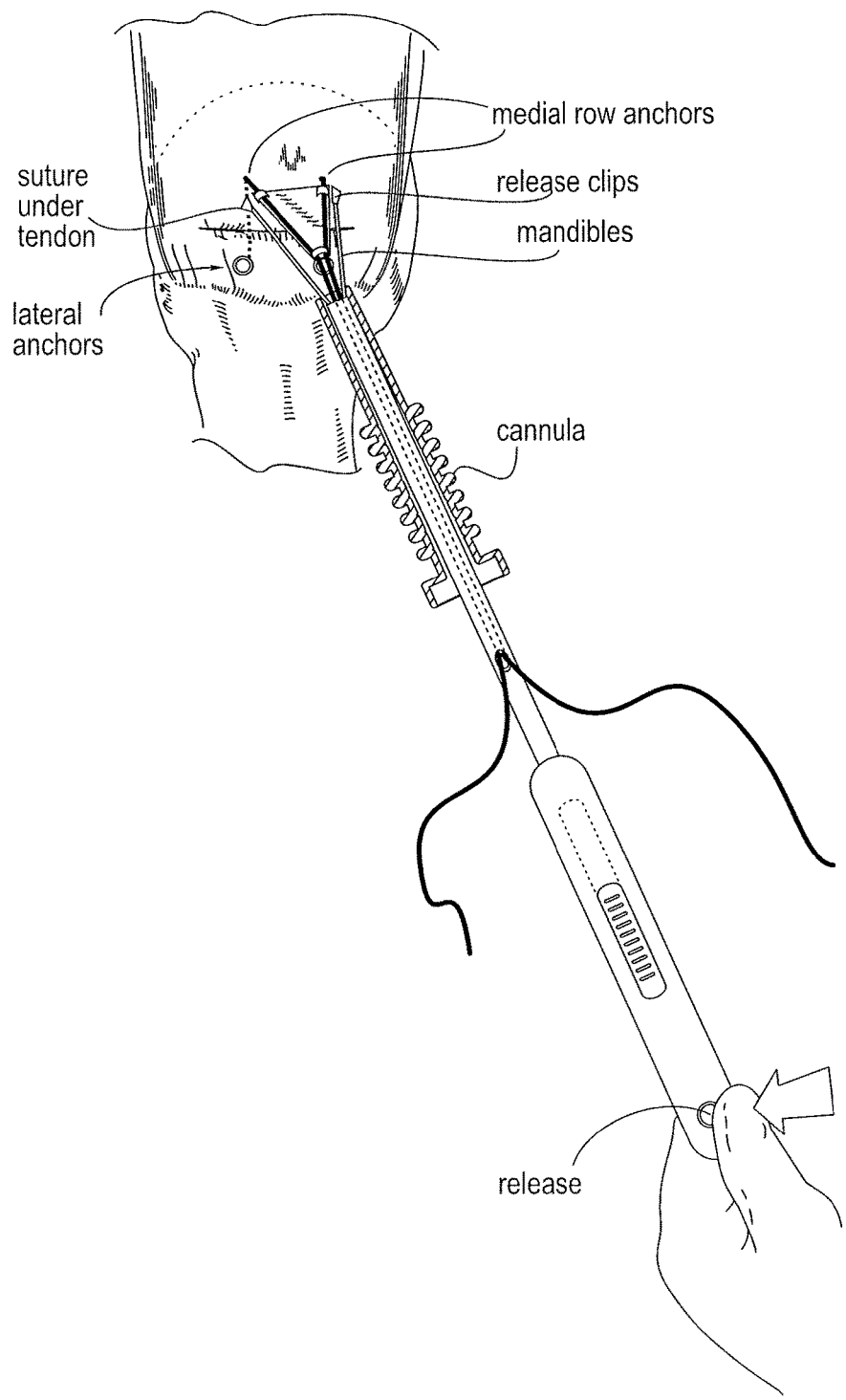
FIG. 52 is a top view of the surgical site of FIG. 51 after operation of the release button to open the mandibles or patch clips to separate the patch from the delivery tool.

FIG. 52 is a top view of the surgical site of FIG. 51 after operation of the release button to open the mandibles or patch clips to separate the patch from the delivery tool.

FIGS. 53A, 53B and 53C are top views of a moveable biased leg patch delivery tool with a patch having a cuff or pocket to engage the distal ends of the biased legs. FIG. 53A shows the tool and patch advanced along the sutures and exiting a working channel with the biasing action of the legs moving the distal end of the patch from a stowed condition.

FIG. 53B is a top view of the surgical site of FIG. 53A with the distal portions of the patch and legs of the delivery tool advanced to the suture anchors. The sutures pass through a loop in the proximal end of the patch. FIG. 53C is a top view of the surgical site in FIG. 53B with the legs of the delivery device withdrawn proximally so as to disengage from the pockets or cuffs of the patch.

FIGS. 54A, 54B and 54C are top views of a delivery tool configured to utilize a suture arranged about a portion of an anchor acting as a pulley. The pulling suture is wrapped about the anchor and attached to a distal portion of the patch as best seen in FIG. 54A. FIG. 54A also shows the tool and patch advanced along the sutures and exiting a working channel with the patch moving from a stowed condition. FIG. 54B is a top view of the surgical site of FIG. 54A with the distal portions of the patch advanced to the suture anchors. FIG. 54C is a top view of the surgical site in FIG. 54B with the pull suture separated from the anchor and withdrawn proximally leaving the distal portion of the patch at the medial anchors.

Figures 55A, 55B:
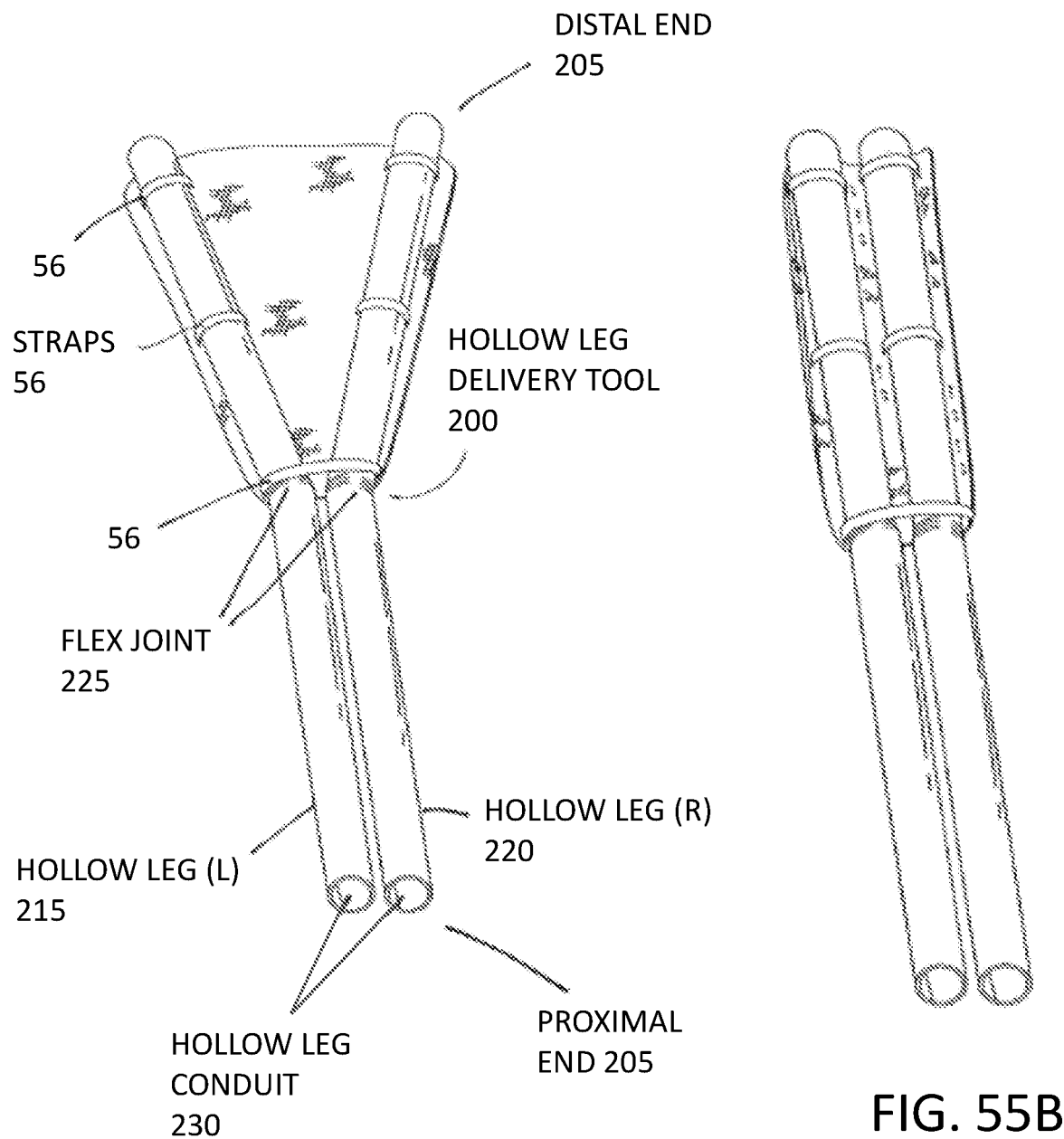
FIGS. 55A and 55B are top down views of an exemplary moveable hollow leg patch delivery tool for delivering a suture guided patch to a surgical site. The suture conduit loops of the guided patch are shown loaded on the distal end of the hollow legs.

FIGS. 55A and 55B are top down views of an exemplary moveable hollow leg patch delivery tool for delivering a suture guided patch to a surgical site. The suture conduit loops of the guided patch are shown loaded on the distal end of the hollow legs. FIG. 55B illustrates the hollow leg device and patch in a stowed condition. FIG. 55A illustrates the hollow leg device and patch in a deployed condition.

Figure 56:
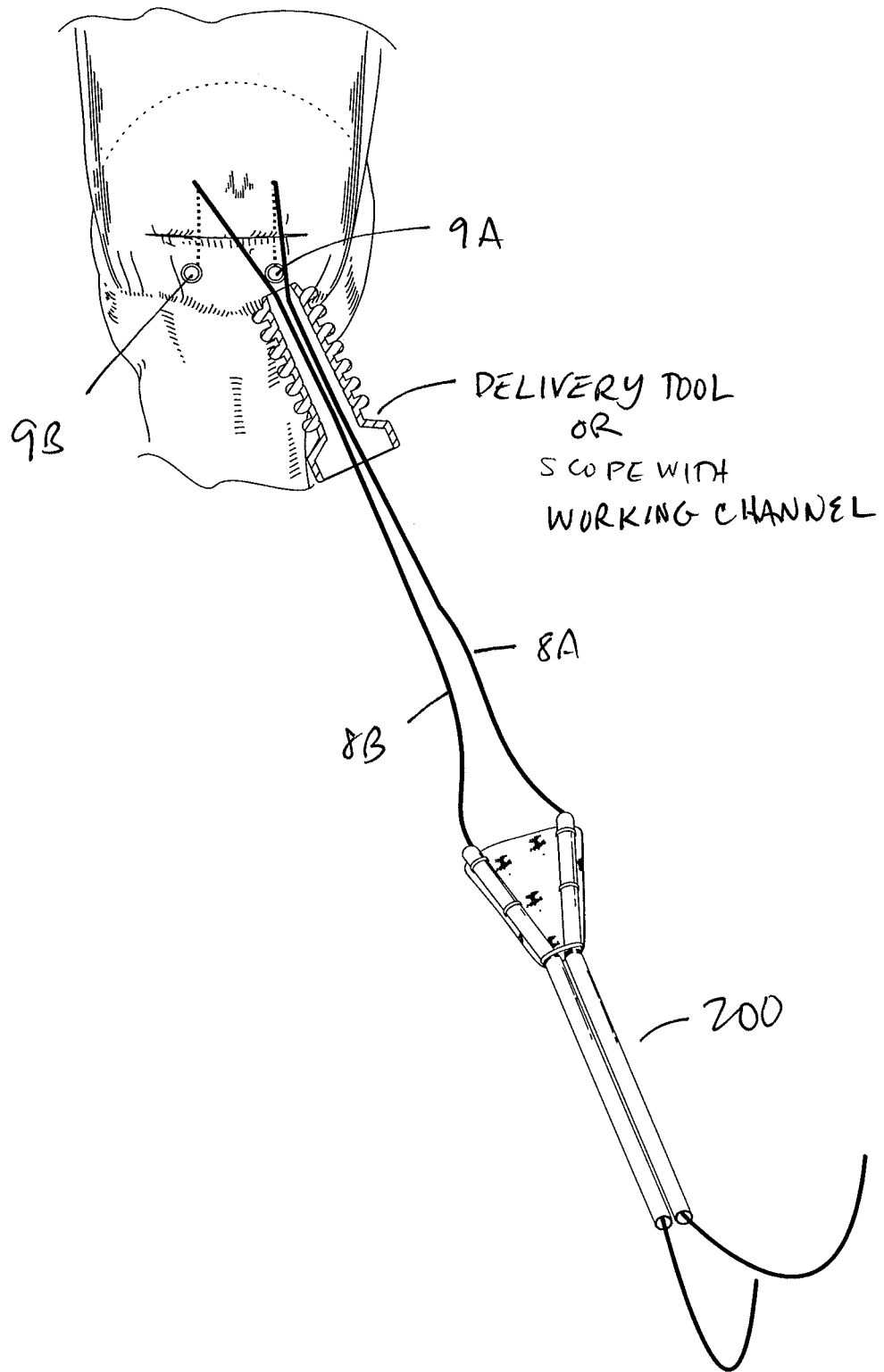
FIG. 56 is a view of the surgical site similar to that of FIG. 49 with the crossed sutures outside the body. This view shows the sutures passed completely through the hollow legs of the delivery device. The patch on the distal end of the delivery device is shown in a deployed condition.

FIG. 56 is a view of the surgical site similar to that of FIG. 49 with the crossed sutures outside the body. This view shows the sutures passed completely through the hollow legs of the delivery device. The patch on the distal end of the delivery device is shown in a deployed condition.

Figure 57:
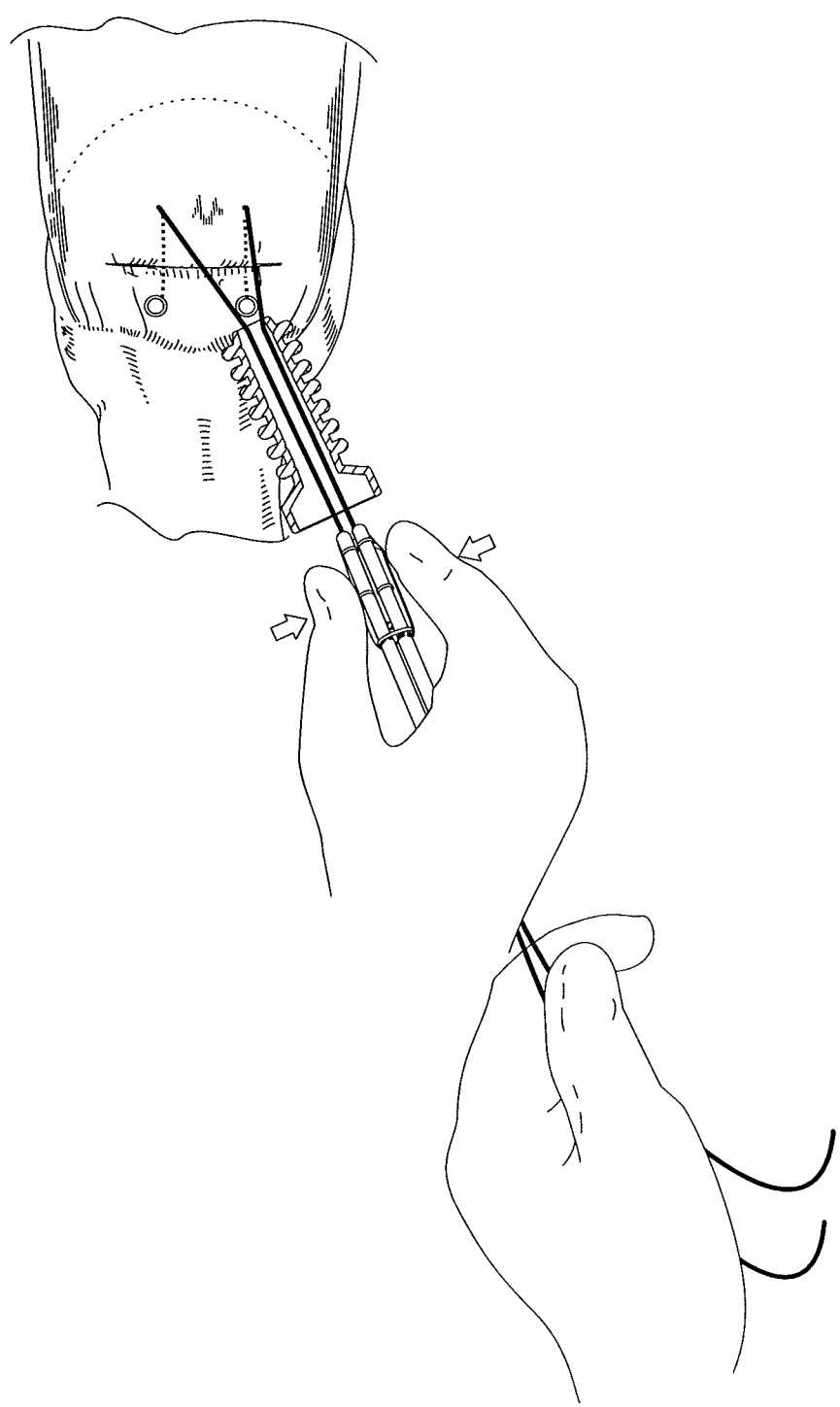
FIG. 57 is a view of the surgical site of FIG. 56 the hollow legs of the delivery device moved together and placing the patch in a stowed condition. Optionally, the patch may be loaded onto the delivery device stowed and then the sutures passed through the hollow legs as shown in FIG. 56. This view also show the stowed patch and closed legs of the delivery device prior to introducing the loaded delivery device into a working channel for delivery to the surgical site.

FIG. 57 is a view of the surgical site of FIG. 56 the hollow legs of the delivery device moved together and placing the patch in a stowed condition. Optionally, the patch may be loaded onto the delivery device stowed and then the sutures passed through the hollow legs as shown in FIG. 56. This view also show the stowed patch and closed legs of the delivery device prior to introducing the loaded delivery device into a working channel for delivery to the surgical site.

Figure 58:
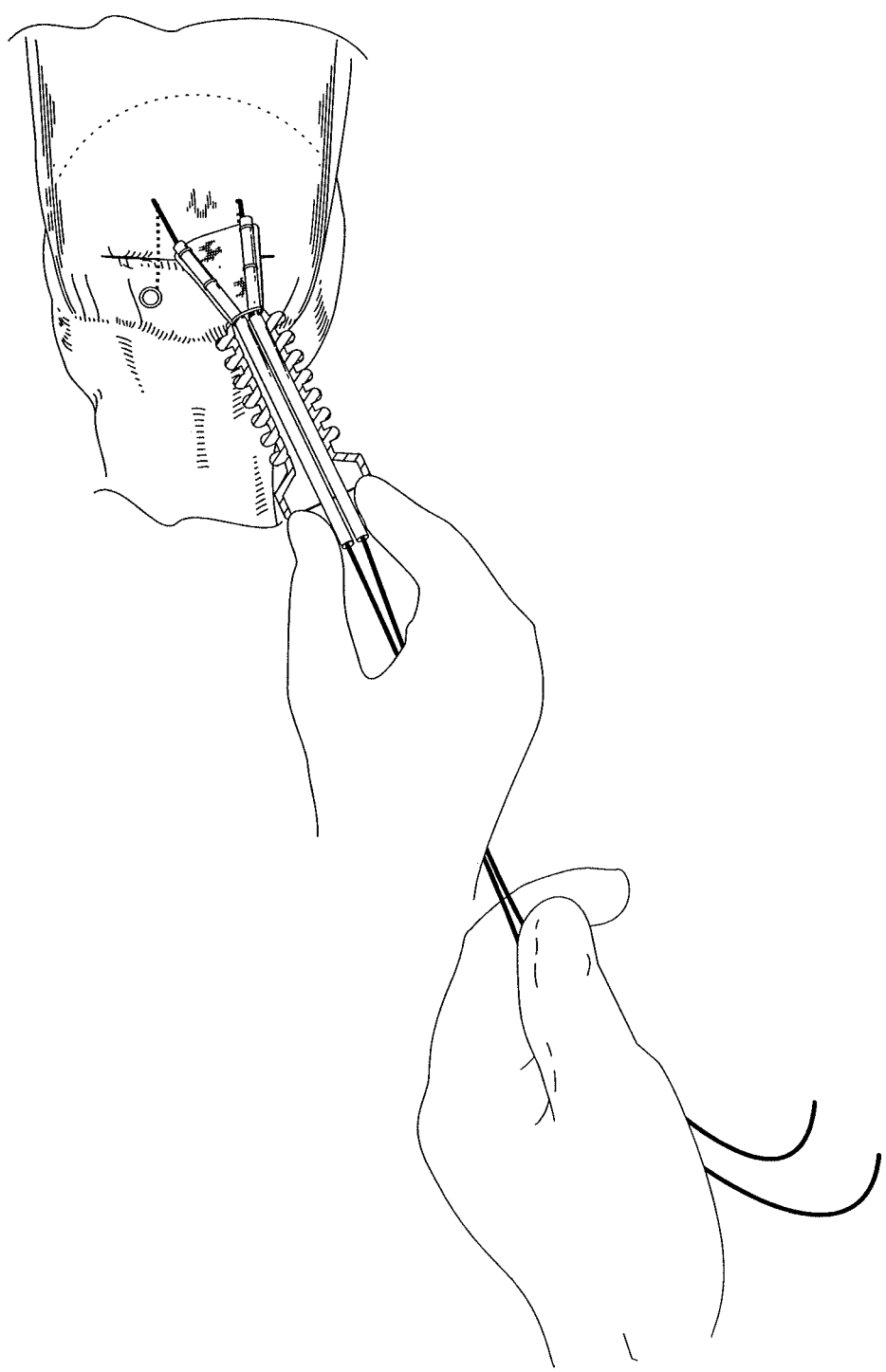
FIG. 58 is a view of the surgical site of FIG. 57 after the delivery device and the patch have been advanced through and exited the working channel of a scope or cannula and moved into a deployed condition. The distal end of the patch is also shown in an position approaching the anchors.

FIG. 58 is a view of the surgical site of FIG. 57 after the delivery device and the patch have been advanced through and exited the working channel of a scope or cannula and moved into a deployed condition. The distal end of the patch is also shown in an position approaching the anchors.

Figure 59:
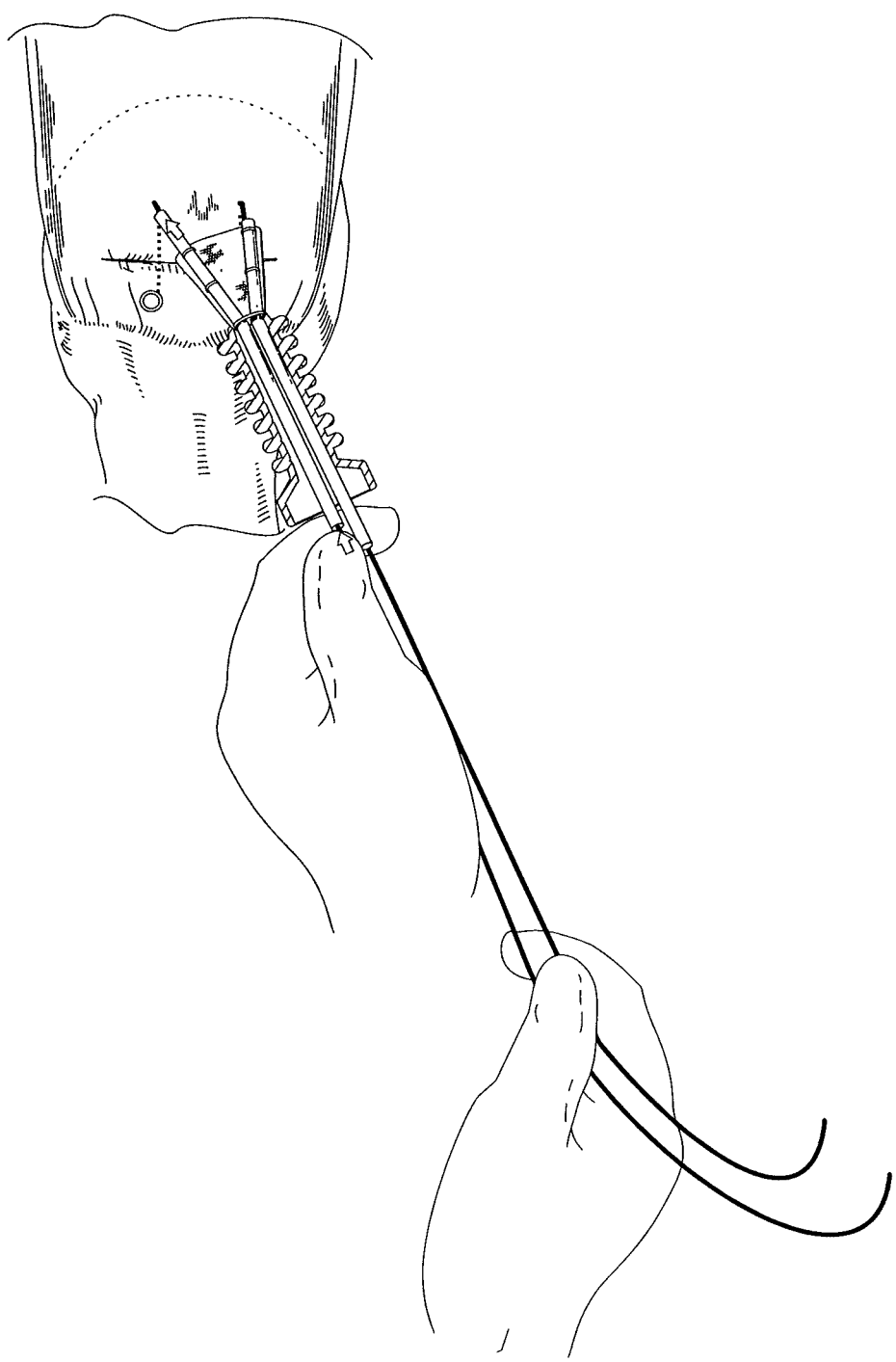
FIG. 59 is a view of the surgical site of FIG. 58 illustrating one leg of the delivery device moving to adjust a portion of the patch relative to the anchor or the surgical site.

FIG. 59 is a view of the surgical site of FIG. 58 illustrating one leg of the delivery device moving to adjust a portion of the patch relative to the anchor or the surgical site.

Figure 60:
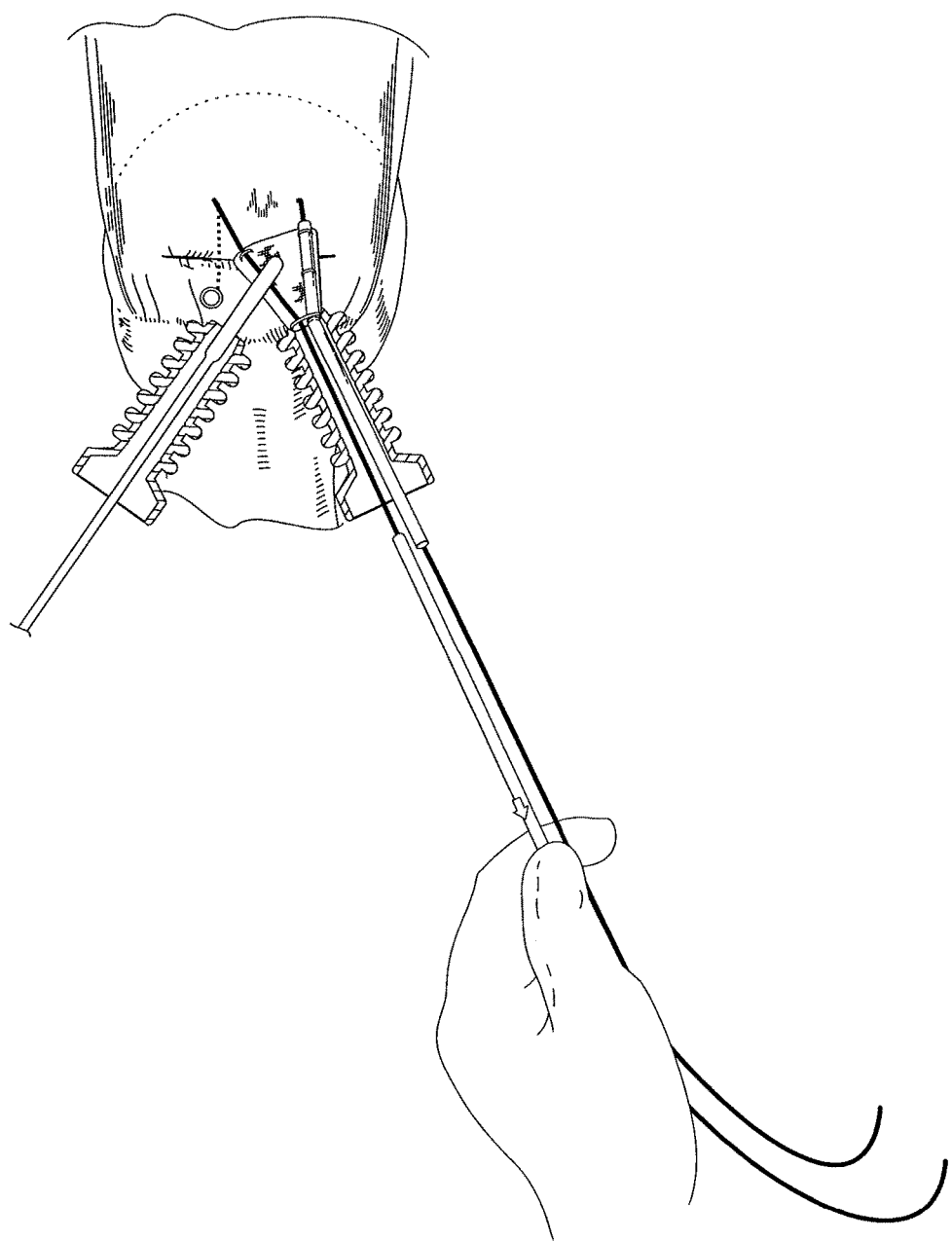
FIG. 60 is a view of the surgical site of FIG. 58. This view also shows an embodiment of the delivery tool where the tool separates for removal from the surgical site after delivery of the patch. The left leg of the tool is shown withdrawn from the body with the right leg in place at the surgical site. An optional tool is shown in this view that is used to hold the patch in the deployed position relative to the anchors or the surgical site while the device is withdrawn or to adjust the patch after tool withdrawal. This view shows the optional tool provided via another surgical access but the tool may be provided along with the delivery device in other configurations.

FIG. 60 is a view of the surgical site of FIG. 58. This view also shows an embodiment of the delivery tool where the tool separates for removal from the surgical site after delivery of the patch. The left leg of the tool is shown withdrawn from the body with the right leg in place at the surgical site. An optional tool is shown in this view that is used to hold the patch in the deployed position relative to the anchors or the surgical site while the device is withdrawn or to adjust the patch after tool withdrawal. This view shows the optional tool provided via another surgical access but the tool may be provided along with the delivery device in other configurations.

Figure 61:
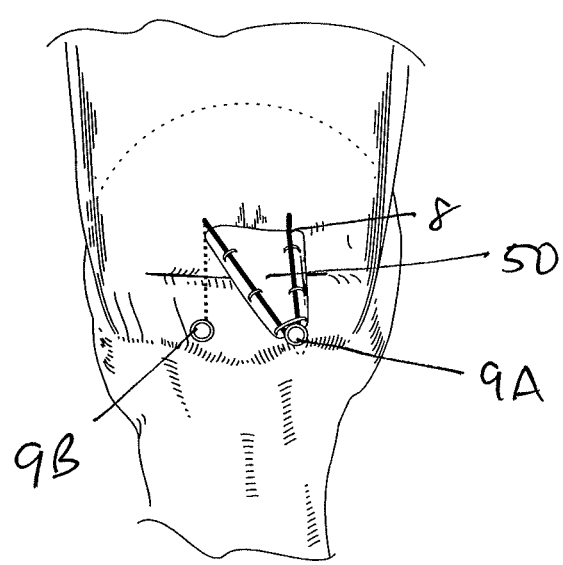
FIG. 61 is a top down view of the surgical sites of FIG. 58 after removal of the delivery tool and securing the patch in the surgical site.

FIG. 61 is a top down view of the surgical sites of FIG. 58 after removal of the delivery tool and securing the patch in the surgical site.

Figure 62:
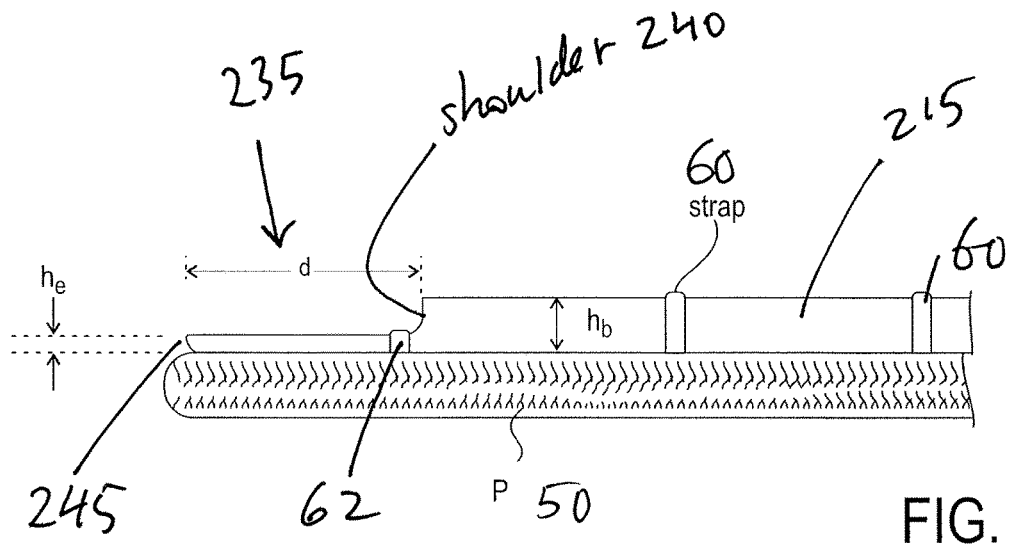
FIGS. 62 and 63 are side and top down views respectively of a hollow leg loaded onto the suture guides of a patch. The distal most end of the hollow leg is reduced to produce a shoulder to engage one of the suture loops to aid movement of the patch along the sutures. These views also show a distal most suture guide loop that is sized to the reduced portion of the hollow leg while additional suture guide loops are sized to the outer dimension of the proximal hollow leg. The patch is illustrated with one reduced size suture loop in the reduced area. Additional suture loops may be provided along the reduced area towards the distal end.
Figure 63:
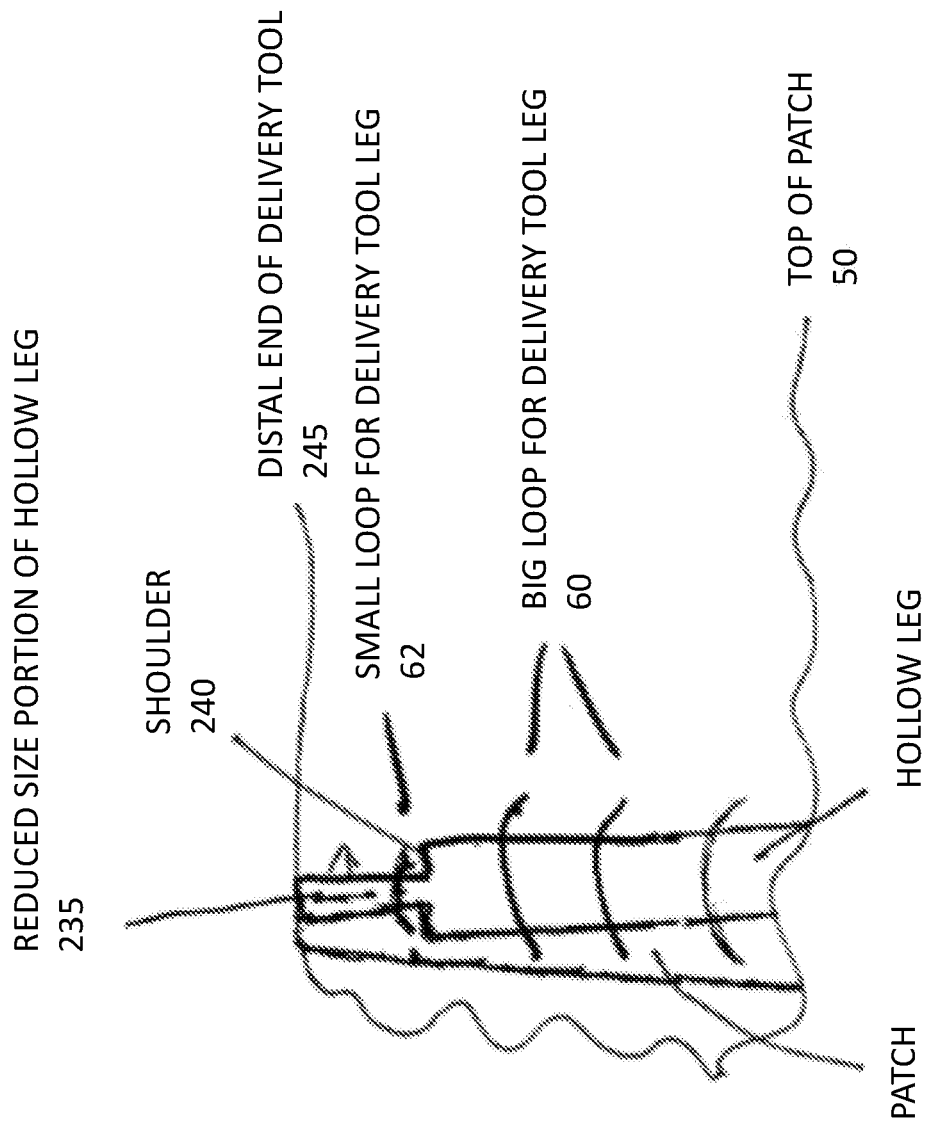

FIGS. 62 and 63 are side and top down views respectively of a hollow leg loaded onto the suture guides of a patch. The distal most end of the hollow leg is reduced to produce a shoulder to engage one of the suture loops to aid movement of the patch along the sutures. These views also show a distal most suture guide loop that is sized to the reduced portion of the hollow leg while additional suture guide loops are sized to the outer dimension of the proximal hollow leg. The patch is illustrated with one reduced size suture loop in the reduced area. Additional suture loops may be provided along the reduced area towards the distal end.

Figure 64:
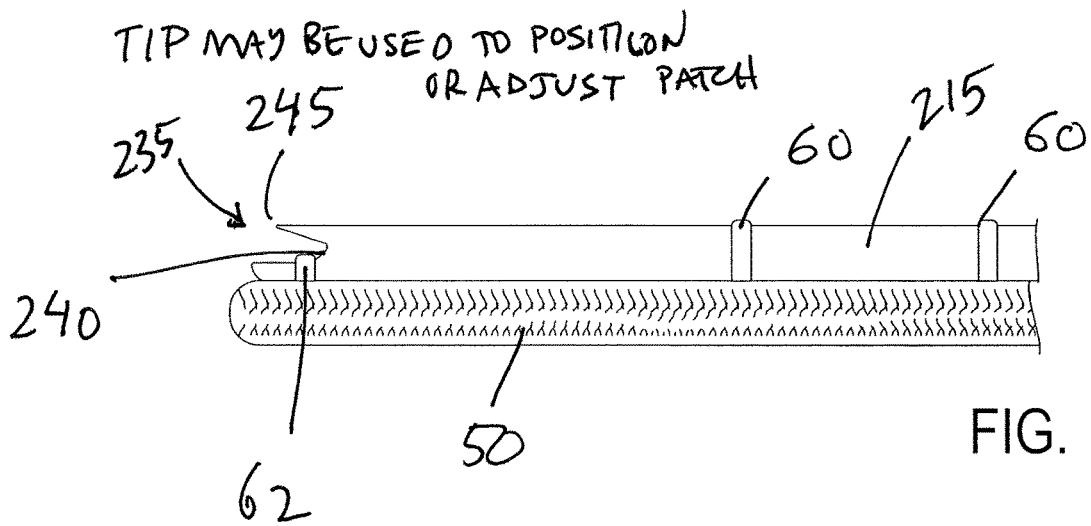
FIG. 64 is a side view of a patch loaded onto a reduced distal end hollow leg as in FIG. 62. This view also illustrates a different length of setback from the distal end of the patch to the shoulder. The upper portion of the reduced area is also provided with a shaped tip to permit use of the hollow leg as a positioning tool after or during patch delivery.

FIG. 64 is a side view of a patch loaded onto a reduced distal end hollow leg as in FIG. 62. This view also illustrates a different length of setback from the distal end of the patch to the shoulder. The upper portion of the reduced area is also provided with a shaped tip to permit use of the hollow leg as a positioning tool after or during patch delivery.

Figures 65A, 65B:
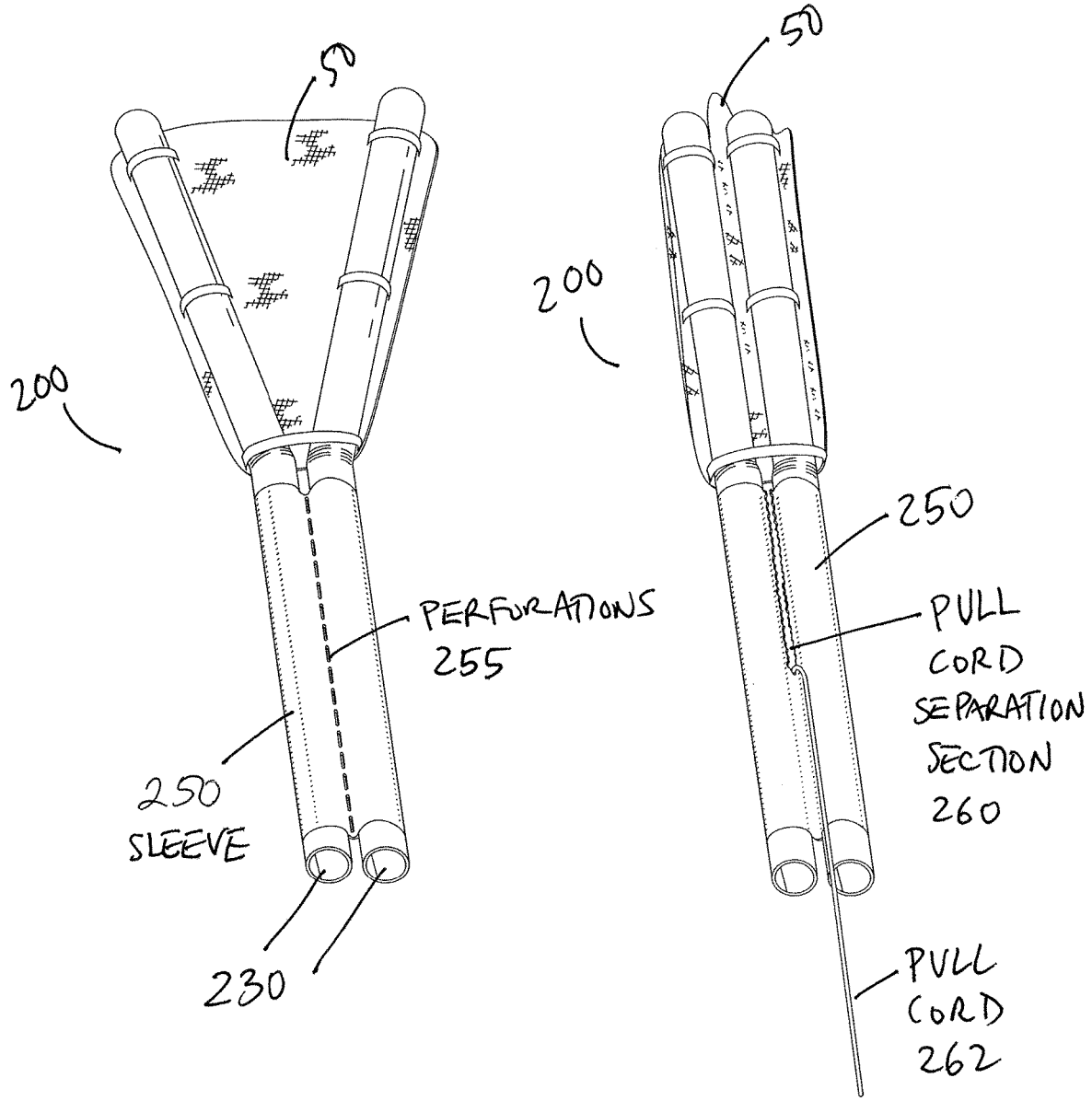
FIGS. 65A and 65B are perspective views of two hollow leg delivery tool embodiments configured to have the legs separate after patch delivery and for withdrawal from the surgical space. A sleeve positioned around the proximal portion of the legs to maintain the legs in position during delivery is shown in each view.

FIGS. 65A and 65B are perspective views of two hollow leg delivery tool embodiments configured to have the legs separate after patch delivery and for withdrawal from the surgical space. A sleeve positioned around the proximal portion of the legs to maintain the legs in position during delivery is shown in each view. FIG. 65A illustrates the sleeve having a perforated segment between each of the proximal portions of the tool. FIG. 65B illustrates a rip cord provided in the sleeve being pulled to separate the legs for removal.

FIG. 66 is a top down view of a hollow leg delivery device that includes a positioning tool or rod. This view shows the delivery tool and patch in a deployed condition with the positioning tool coupled to a distal portion of the patch.

FIG. 67 is a top down view of a hollow leg delivery device that includes a positioning tool or rod adapted to engage with a pocket or cuff provided on the patch as shown in FIGS. 53A-53C. This view shows the delivery tool and patch in a stowed condition with the positioning tool within the pocket or cuff of the patch.

In still another aspect, the hollow leg delivery device 200 may be adapted for use as a measuring device useful in estimating the sizes and spacing of relevant portions of the suture based surgical repair site. These measurements or sizing estimates may then be used in the selection of a patch from a selection of pre-set patches of different dimensions. Additionally or optionally the measurement and estimation tools may provide input for use in one or more patch selecting and preparing methods 7400 in FIG. 74 or one of FIGS. 43A to 50. In one aspect, the patch measurement and estimating device is adapted to measure the distance between the two medial anchors and the distance between the medial row anchors and lateral row anchors. In one embodiment, a leg of the delivery device or other suitable tube is adapted to receive a suture from the surgical site. The tube or leg would then slide down the suture to the anchor. In one embodiment, the suture is a suture from the medial row. The tube should have circular windows spaced at different lengths. Exemplary spacing for the windows includes 0.5, 1.0, 1.5 and 2.0 cm. The tube would include two windows at each length on opposite sides of the tube. In another embodiment, a measuring device to measure the distance between the 2 medial anchors would be 2 hollow leg flexible tubes such as the legs of the device 200. The legs are joined together as described herein. A string or filament or suture of known length is attached to the distal most end of each of the legs. The string or filament is attached so as to limit the maximum amount that the distal ends of the legs are separated. Then, sutures from the medial anchors to be used for suture guided patch delivery would be passed though the hollow leg conduits. The bendable leg measurement device is than advanced along the suture as would be done during delivery of a patch. Advancement of the hollow legs of the measurement device continues through the cannula until the distal ends touch the medial anchors. At this point, the distal end of the hollow legs is at the maximum width. The string or filament length may be set to the maximum width for a patch in the deployed configuration. In this way a potential patch size may be tested with the string size prior to loading onto the sutures. If the test string was set at 2.0 cm for example, then when in place at the medial anchors, so long as the string was not too taught, then one can confirm that a patch sized for deployment to a 2.0 cm delivery spacing would fit between the 2 medial anchors. Other sizes may be used or the measurement tools may be configured for use with the patch sizes included in a pre-set size patch kit.

Exemplary Surgical Methods Incorporating Suture Guided Patches

FIGS. 68-74 provide additional details of surgical methods where one or more steps of a suture repair workflow is modified to incorporate one or more of the various embodiments of suture guided patches described herein.

FIG. 68 is a flow chart of an exemplary surgical method for placing a suture guided patch in a surgical site (method 6800). Method 6800 begins at step 6805 by placing one or more suture anchors of the surgical site. Next, at step 6810, performing one or more steps of a suture repair procedure is needed before placement of a suture guided patch at the surgical site. Next, at step 6815, inserting a suture used in the suture repair procedure through a suture conduit of the suture guided patch. Thereafter, there is the step of advancing the patch along the suture (step 6820). Next, at step 6825, is the step of securing the patch in the surgical site with the suture. Finally, there is the step of releasing from the patch at least one patch delivered material. (step 6830).

Figure 69:
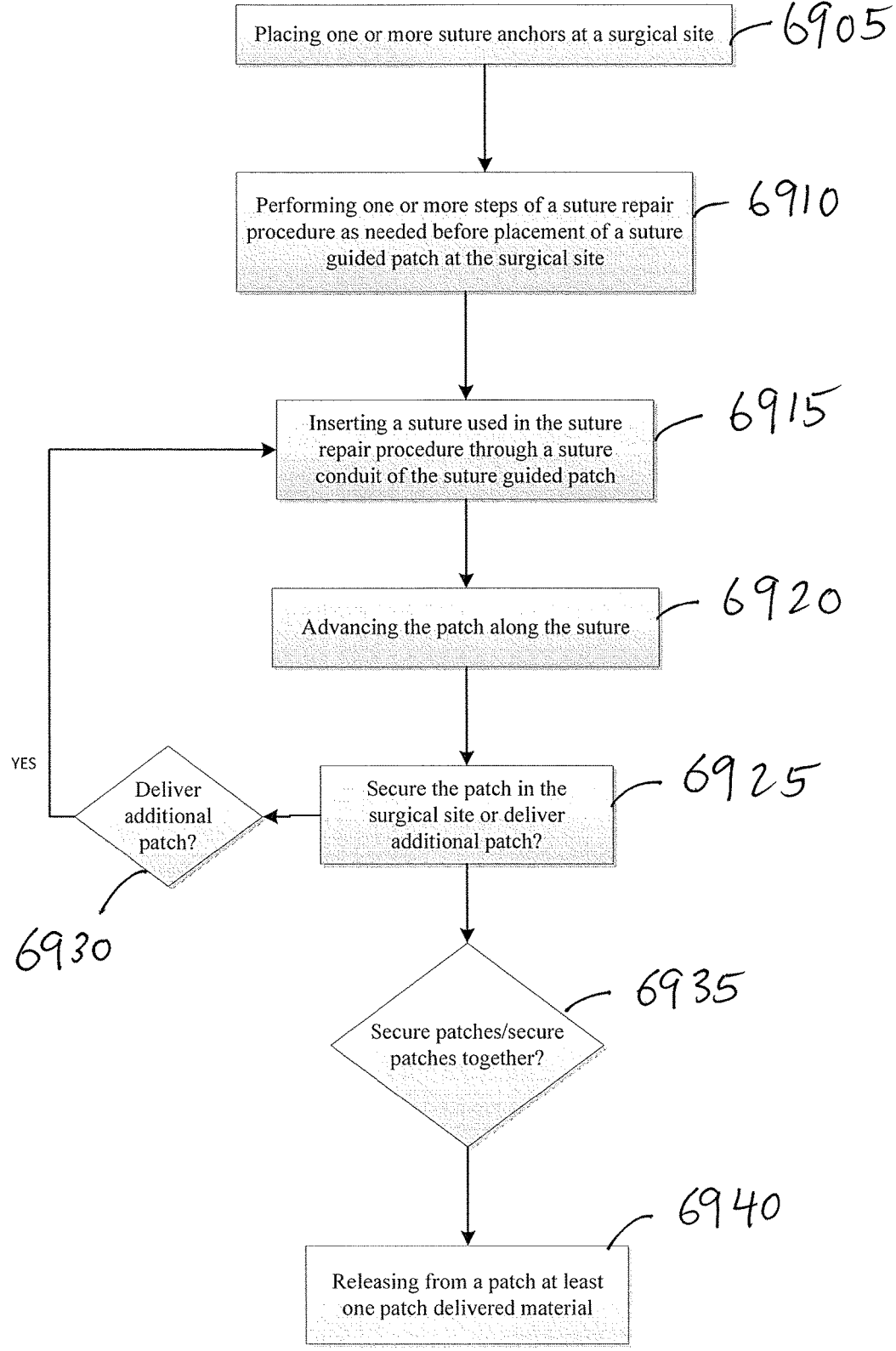
FIG. 69 is a flow chart of an exemplary surgical method for placing 2 or more suture guided patches in a surgical site.

FIG. 69 is a flow chart of an exemplary surgical method 6900 for placing 2 or more suture guided patches in a surgical site. First, at step 6905, there is the step of placing one or more suture anchors at the surgical site. Next, at step 6910, there is the step of performing one or more steps of the suture repair procedure as needed before placement of a suture guided patch at the surgical site. Thereafter, there is a step of inserting a suture used in the suture repair procedure through a suture conduit of the suture guided patch (Step 6915) and then advancing the patch along the suture (step 6920). At this point, the surgeon may choose to secure the patch in the surgical site (step 6925 YES) or wait to secure all or another patch so that all patches are secured simultaneously after being delivered. If the surgeon determines that additional patches are to be delivered by answering yes step 6930 then the process repeats at step 6915 by inserting another suture guided patch or delivery to the surgical site. After all patches are delivered, the patches may be secured together (as shown in FIGS. 18, 19, 36 and 38) or using other suitable techniques (step 6935). Finally, there is the step of releasing from the patch at least one patch delivered material. (step 6940).

Figure 70:
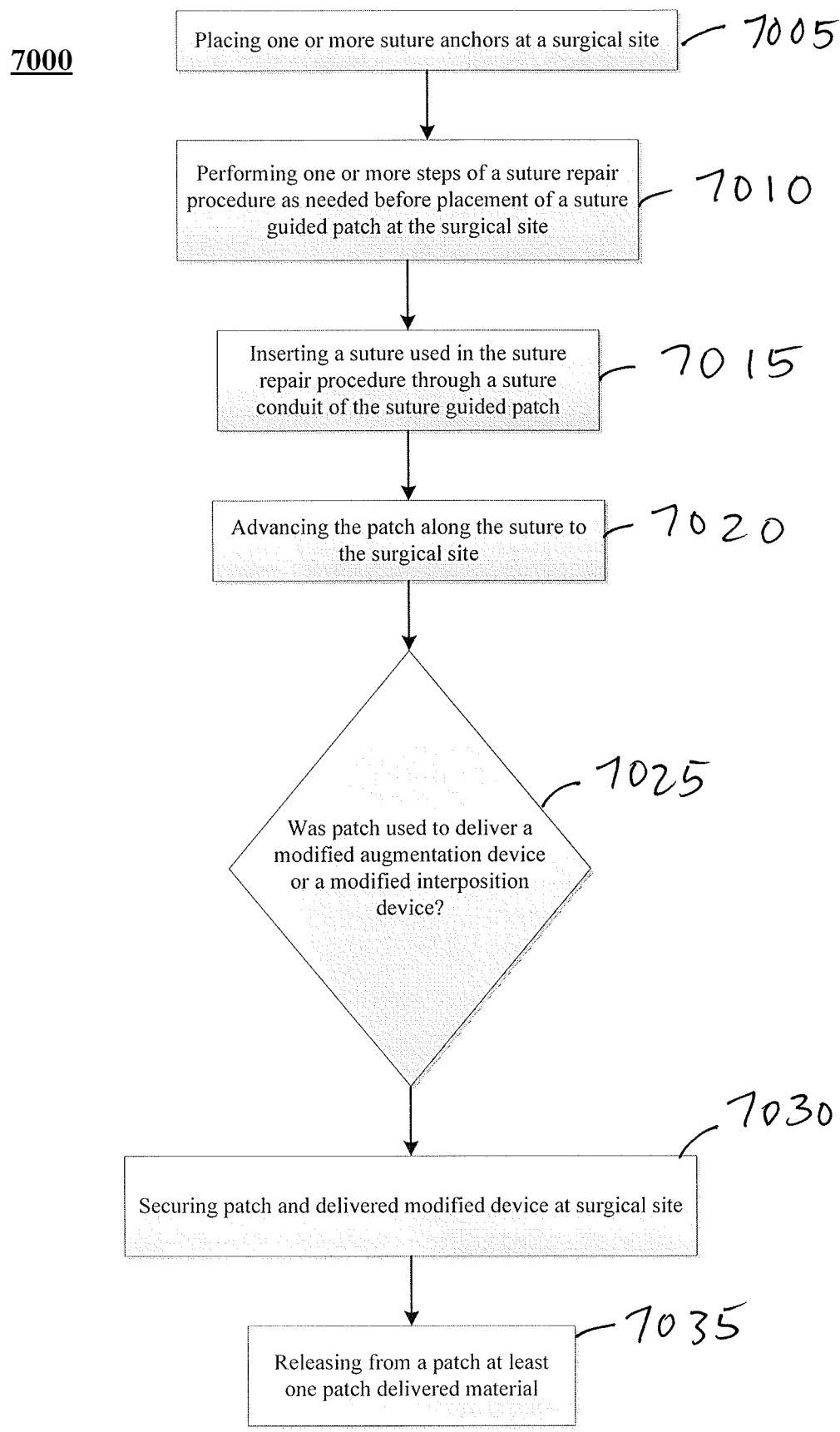
FIG. 70 is a flow chart of an exemplary surgical method for placing a suture guided patch in a surgical site including the use of a patch for the delivery of a modified augmentation device or a modified interposition device.

FIG. 70 is a flow chart of an exemplary surgical method for placing a suture guided patch in a surgical site including the use of a patch for the delivery of a modified augmentation device or a modified interposition device. A modified augmentation device or a modified interposition device may be coupled in an appropriate manner to a suture guided patch adapted for the purpose such as by using the techniques described above with regard to FIGS. 43A-46. Thereafter, at step 7005, there is the step of placing one or more suture anchors at the surgical site. Next, at step 7010, there is the step of performing one or more steps of the suture repair procedure as needed before placement of a suture guided patch at the surgical site. Thereafter, there is a step of inserting a suture used in the suture repair procedure through a suture conduit of the suture guided patch (Step 7015) and then advancing the patch along the suture to the surgical site (step 7020). When an embodiment of the suture guided patch is used to provide an augmentation or interposition device (step 7025 is yes) then both the augmented device and the patch are secured as appropriate to the surgical site (7030). Finally, there is the step of releasing from the patch at least one patch delivered material. (step 7035) which may have a specially devised material release profile for use in conjunction with the modified device.

Figure 71:
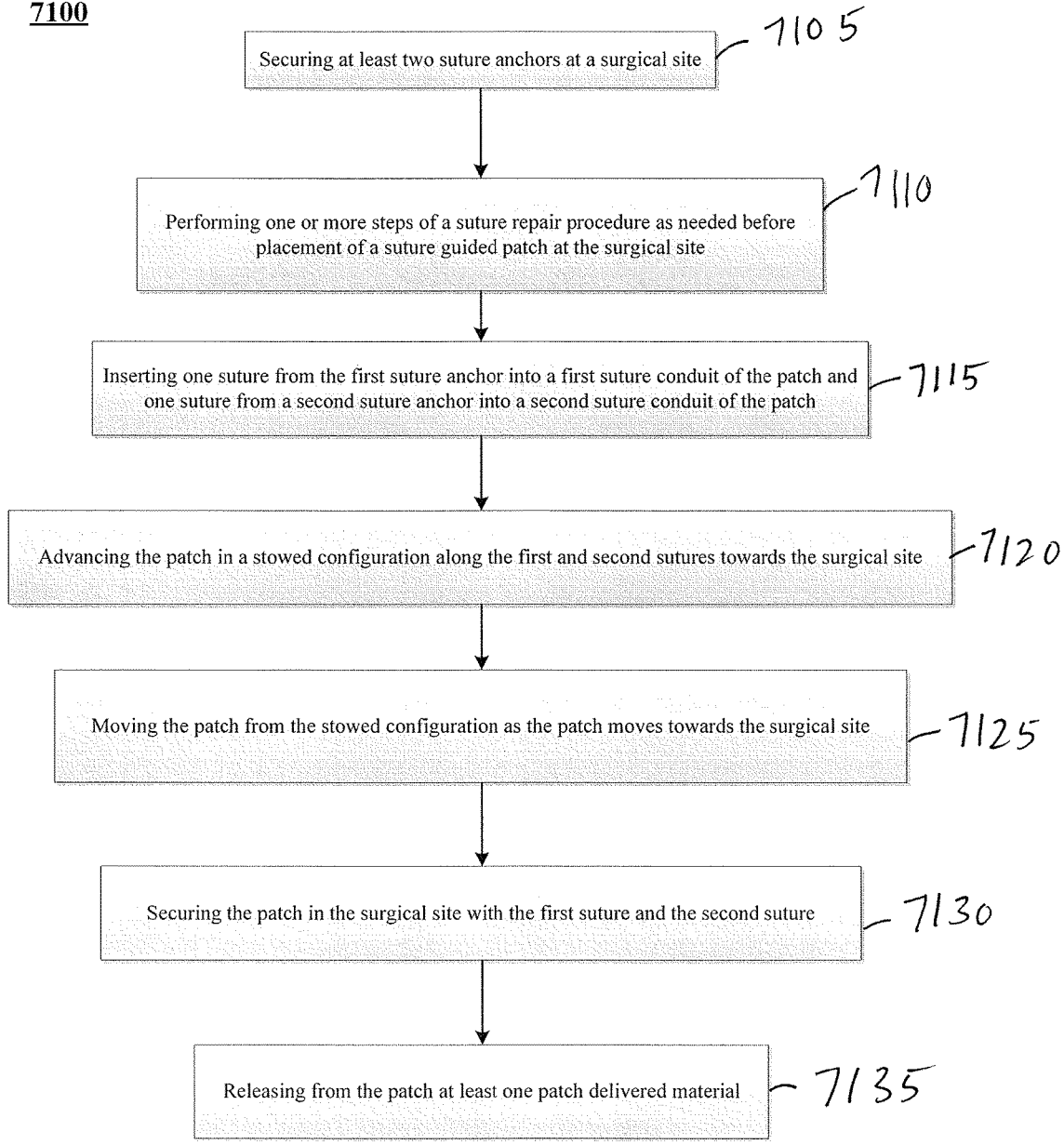
FIG. 71 is a flow chart of an exemplary surgical method of the movement from a stowed condition of a suture guided patch being delivered to a surgical site.

FIG. 71 is a flow chart of an exemplary surgical method 7100 of the movement from a stowed condition of a suture guided patch being delivered to a surgical site. At step 7105 there is the step of securing at least 2 suture anchors in a surgical site. Next, at step 7110 there is the step of performing one or more steps of the suture repair procedure as needed before placement of the suture guided patch at the surgical site. Next, at step 7115, there is the step of inserting one suture from the $1^{st}$ suture anchor into a $1^{st}$ suture conduit of the patch and one suture from a $2^{nd}$ suture anchor into a $2^{nd}$ suture conduit of the patch. Thereafter, at step 7120, there's the step of advancing the patch and stowed configuration along the $1^{st}$ and $2^{nd}$ sutures towards the surgical site. Next, at step 7125, is the step of moving the patch from the stowed configuration as the patch moves towards the surgical site. Is to be appreciated that the step may be accomplished in a number of different ways. One way the patch moves from the step configuration is simply by having the patch loaded in compression within the working channel of the instrument used to deliver the patch. As the patch moves out of the working channel, the patch moves from the stowed configuration. In another example, the patch may be urge to move as it advances along the suture conduits because the suture conduits are oriented in a diverging path whereby as the suture conduits move towards the suture anchors the patch will be moved along with the conduits into a deployed configuration. Thereafter, at step 7130, is the step of securing the patch in the surgical site with the $1^{st}$ suture and the $2^{nd}$ suture. Here as with the other methods the suture used to deliver the patch and that remains within the suture conduits of the patch is used to secure the patch at the surgical site. Next, at step 7135, depending upon the specific design release profile of the patch, there's the step of releasing from the patch at least one patch delivered material.

Figure 72:
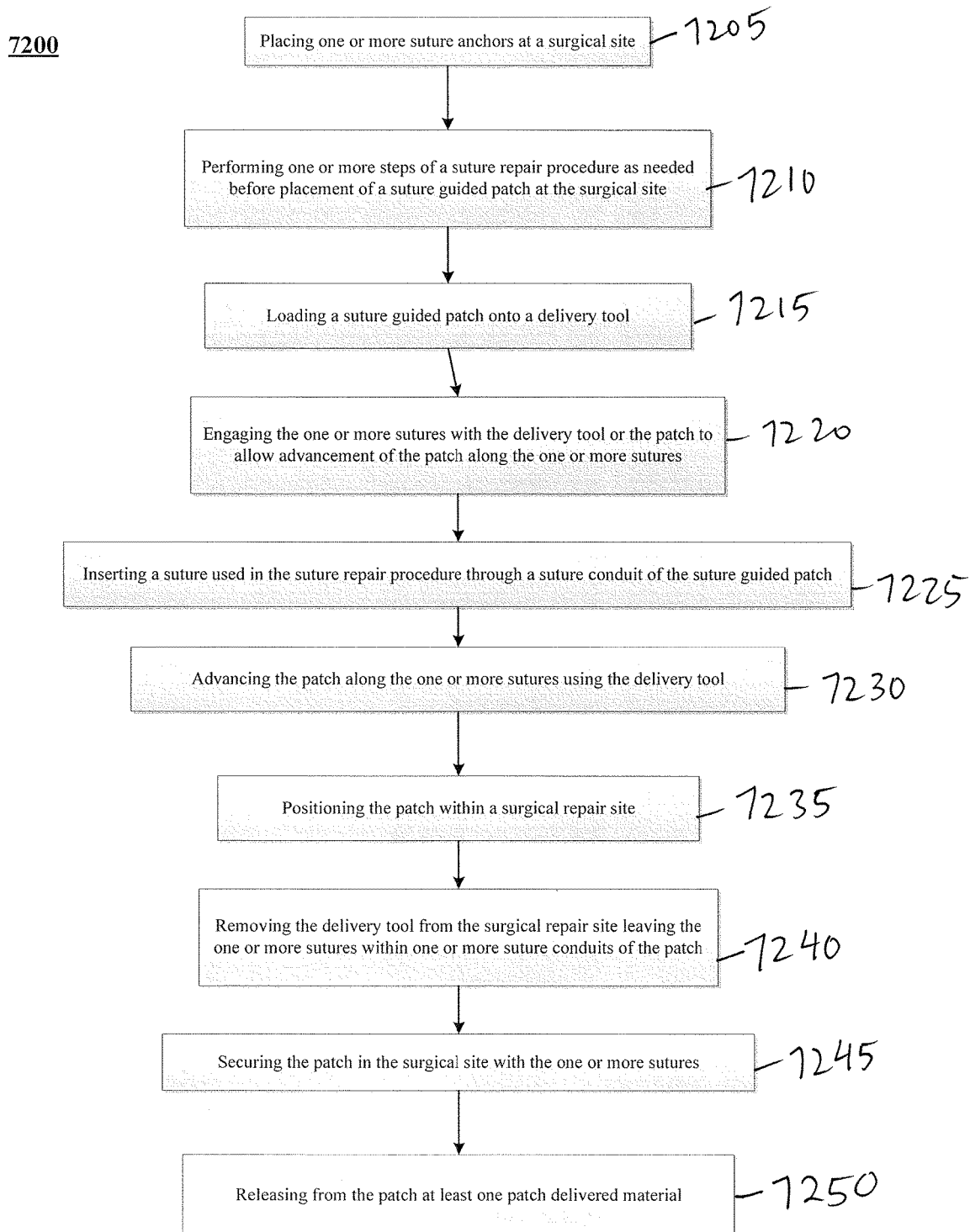
FIG. 72 is a flow chart of an exemplary surgical method for the use of an exemplary patch delivery tool for delivering a suture guided patch to a surgical site.

FIG. 72 is a flow chart of an exemplary surgical method 7200 for the use of an exemplary patch delivery tool for delivering a suture guided patch to a surgical site. At step 7205 there is the step of securing at least 2 suture anchors in a surgical site. Next, at step 7210 there is the step of performing one or more steps of the suture repair procedure as needed before placement of the suture guided patch at the surgical site. Next, at step 7215, is the step of loading a suture guided patch onto a delivery tool. Next, at step 7220, is the step of engaging the one or more sutures with the delivery tool or the patch to allow advancement of the patch along the one or more sutures. Next, at step 7225, is the step of inserting a suture used in the suture repair procedure through a suture conduit of the suture guided patch. Next, at step 7230, is the step of advancing the patch along the one or more sutures using the delivery tool. Next, at step 7235, is the step of positioning the patch within the surgical repair site. Next, at step 7240, is the step of removing the delivery tool from the surgical repair site leaving the one or more sutures within the one or more suture conduits of the patch.

Next, at step 7245, securing the patch in the surgical site with the one or more sutures. Next, releasing from the patch at least one patch delivered material (step 7250).

Further to the exemplary delivery method 7200 in FIG. 72 and with reference to FIG. 58, as the suture delivered device and hollow leg delivery tool advance along the sutures and through the delivery cannula, the hollow legs of the device will separate as the individual sutures lead to each of the individual suture anchors 9A,9B. The action of the legs of the hollow leg delivery device to open will also transition the patch from the stowed condition into a delivered condition. In the delivered condition, at least one side of the patch corresponds to the spacing between adjacent suture anchors. Thereafter, the hollow leg delivery tool is withdrawn leaving the suture delivered patch in place. Next, the completion of the suture repair procedure is completed by anchoring the sutures that are along the patch to the appropriate location within the surgical field. As a result of the anchoring of the sutures, the suture delivered patch is also secured in place. The process is repeated for additional suture anchors and patches depending upon the desired surgical outcome. While described with specific mention of the hollow leg delivery device embodiments, the flexible legs and suture following movement of the delivery device and the patch occurs as well in the embodiments and illustrative patch delivery in FIGS. 51 & 53A-53C.

FIG. 73 is a flow chart of an exemplary surgical method 7300 for the use of an exemplary moveable leg patch delivery tool for delivering a suture guided patch to a surgical site. As with the prior methods, one or more sutures anchors are placed (step 7305) and one or more steps of the procedure are performed as necessary (step 7310). Next, at step 7315, there is a step of loading a suture guided patch onto a movable leg patch delivery device. Next, at step 7320, is the step of engaging two sutures with the patch or the patch delivery device to allow advancement of the patch along the one or more sutures towards the surgical site. Next, at step 7325, is the step of advancing the patch in the stowed condition along the 2 sutures towards the surgical site using the patch delivery device. Next, at step 7330, is the step of moving the patch from the stowed condition by separating the legs of the patch delivery device. Next, at step 7335, is the step of positioning the deployed patch within the surgical repair site. Next, is the step of removing the delivery tool from the surgical repair site, step 7340. In some embodiments the delivery tool may separate upon removal or may be removed as a single unit. This decision point is reflected at step 7345. If the delivery tool does not separate on removal, the answer at step 7345 is no and the method continues at step 7350. The delivery tool is removed from the surgical site with the one or more sutures remaining within the one or more suture conduits of the patch. If, the delivery tool does separate for removal, step 7345 is yes, then the method proceeds at step 7355. In the step the user will remove components of the delivery tool in sequence from the surgical repair site. At the conclusion of the sequence one or more sutures will be left remaining within the one or more suture conduits of the patch. Next at step 7360, the positioning rod if used during the use of the delivery device or if provided with the delivery device is also removed from the surgical site. (see FIGS. 24, 66 and 67). Next, at step 7365, if not secured previously, the patch is secured in the surgical site with the one or more sutures that remain within suture conduits of the patch. Thereafter, while remaining at the surgical site according to the designed release profile, there's the step of releasing from the patch at least one patch delivered material. (Step 7370).

Figure 74:
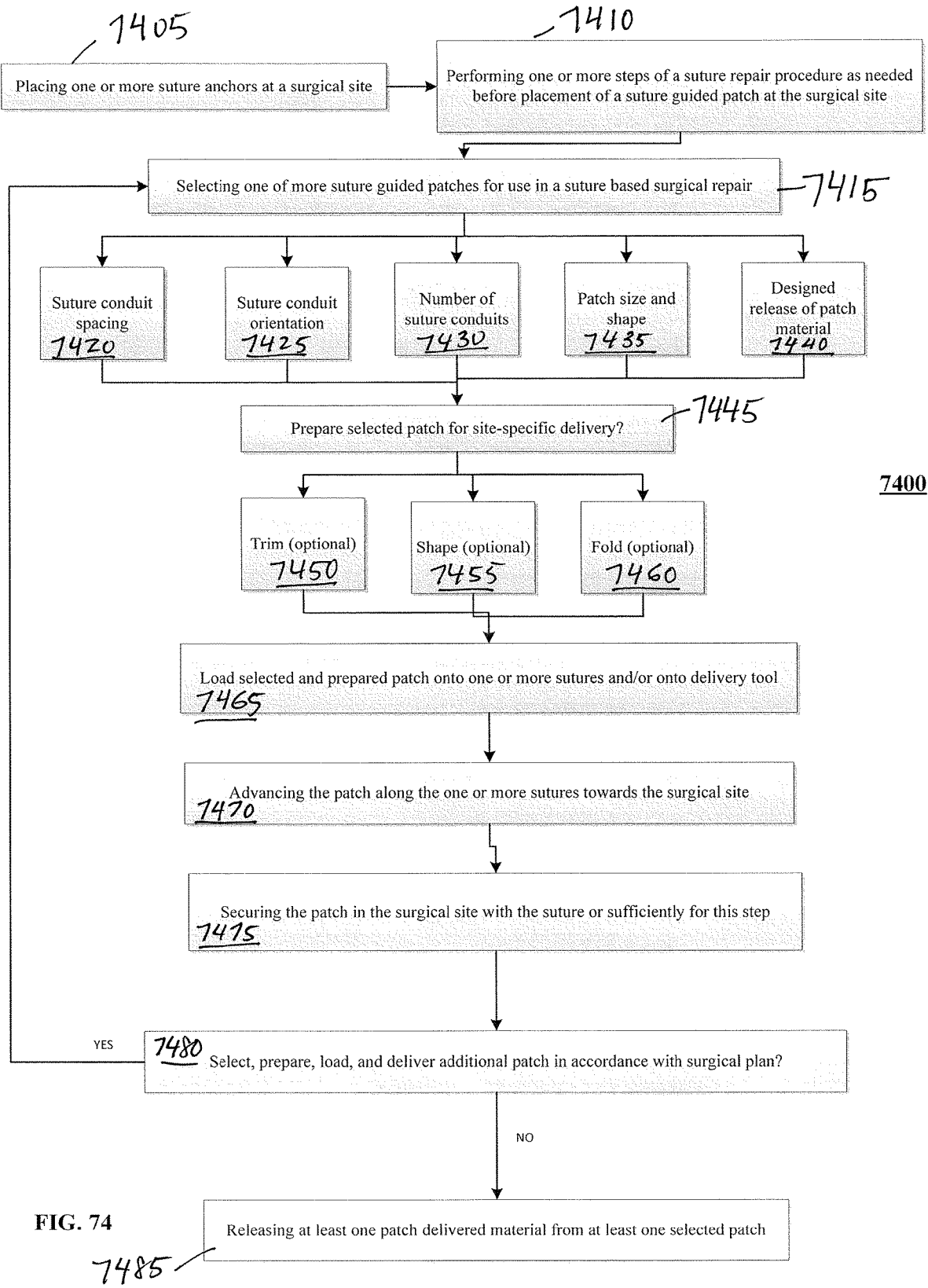
FIG. 74 is a flow chart of an exemplary surgical method for selecting and optionally preparing a selected patch for suture guided delivery to a surgical site.

FIG. 74 is a flow chart of an exemplary surgical method for selecting and optionally preparing a selected patch for suture guided delivery to a surgical site. In order to provide additional flexibility for the use of suture delivered patches, a number of different patch types and sizes may be provided to the surgeon or adaption to a particular surgical case or patient need. As with the prior methods, method begins by placing one or more suture anchors at a surgical site. (Step 7405). Next, one or more steps of a suture repair procedure are performed as needed before the placement of the suture guided patch at the surgical site. (Step 7410). Next, the surgeon selects one or more suture guided patches for use in the suture-based surgical repair. (Step 7415). The process of selecting includes the surgeon evaluation of our number of different factors of a particular suture guided patch. Among the exemplary characteristics upon which to make this selection are suture conduits spacing (step 7420), suture conduit orientation (step 7425), number of suture conduits (step 7430), patch size and shape (step 7435), and designed release of patch material (step 7440). Next, as a result of the selection process above, is the step of preparing the selected patch for site-specific delivery (step 7445). Here, the patch may be optionally adapted for the particular surgery or repair being performed. By way of example, a selected patch may be trimmed (step 7450), shaped (step 7455) or folded one or more times (step 7460). In one embodiment, the suture guided patches may come in a standard width, such as 1.0 cm, 1.5 cm or 2.0 cm or more than the width between adjacent suture anchors but be supplied in a standard length, such as a length sufficient for most surgical applications, for example 10 cm or less depending upon surgical need and surgeon preference. As part of step 7450, the patch would then be cut to the desired length once the desired preset with was selected. Additionally, with regard to the shaping step 7455, patches of different shapes may be provided with a different area of coverage whereby after selecting the particular shape of patch for use it may then be trimmed according to step 7450 or folded according to 7460 in order to that the particular need of a surgical site repair. (See FIGS. 43A-46 above). In this way, a suture guided patch may be trimmed or shaped to size starting from a standard shaped areas (all in square centimeters) of 1.0, 1.5, 2.0, 2.5, 3.0, 3.5, 4.0 or others depending on surgical needs. Thereafter, at step 7465, the selected and prepared patch is loaded onto one or more sutures and/or a delivery tool, as desired. Next, at step 7470 the patch is advanced along the one or more sutures towards the surgical site. Afterwards, the patch is secured in the surgical site or sufficiently secured or any additional patches or steps to be taken at the surgical site for securing this patch. (Step 7475). Next, at step 7480, the method then proceeds or the additional selection preparation loading and delivery of any additional patches according to the surgical plan. If more patches are to be delivered the process continues by returning to the selecting step 7415. If all patches have been delivered according to the surgical plan, then the answer at step 7480 is no surgery is completed and according to the designed release profile of the patch, at least one patch lived material will be released from the patch (step 7485).

While the above embodiments have described primarily for use with the repair of the rotator cuff of the shoulder, it is to be appreciated that the surgical repair patches, tools and suture anchor delivery methods described herein may be adapted to a wide variety of soft tissue repair of ligaments and joints such as, for example:

Shoulder—
  Capsular stabilization
  Bankart repair
  Anterior shoulder instability
  SLAP lesion repairs
  Capsular shift or capsulolabral reconstructions
  Acromioclavicular separation repairs
  Deltoid repairs
  Biceps tenodesis
Foot and Ankle
  Hallux valgus repairs
  Medial or lateral instability repairs/reconstructions
  Achilles tendon repairs/reconstructions
  Mid and forefoot reconstructions
  Metatarsal ligament/tendon repairs/reconstructions
  Bunionectomy
Elbow
  Ulnar or radial collateral ligament reconstruction
  Lateral epicondylitis repair
  Biceps tendon repair
Hand and Wrist
  Collateral ligament repair
  Scapholunate ligament reconstruction
  Volar plate reconstruction
  Tendon transfers in phalanx
Hip
  Acetabular labral repair
Knee
  Extra-capsular repairs
    Medial collateral ligament
    Lateral collateral ligament
    Posterior oblique ligament
  Patellar realignment and tendon repairs
  Illiotibial band tenodesis
  VMO advancement
  Joint capsule closure In still other embodiments, various augmentation devices and interposition devices may also be modified for use with the suture guided techniques described herein.

"Augmentation device (or graft)" as used herein refers to a material that can be used to strengthen a rotator cuff repair. For example, a surgeon may enhance the strength of a rotator cuff repair made with sutures by incorporating a reinforcing material into the repair. In one aspect, and augmentation device is modified according to the principles described herein to permit suture guided delivery of the modified augmentation device. The modified augmentation device may include a dedicated suture channel, a continuous suture channel, and intermittent suture channel or joined to an embodiment of a suture guided patch whereby the suture guided patch provides for suture guided delivery of the modified augmentation device.

"Interposition device (or graft)" as used herein refers to a material that is used to bridge a gap (or defect) between the end of a tendon and its bony insertion site. In one aspect, and interposition device is modified according to the principles described herein to permit suture guided delivery of the modified interposition device. The modified interposition device may include a dedicated suture channel, a continuous suture channel, and intermittent suture channel or joined to an embodiment of a suture guided patch whereby the suture guided patch provides for suture guided delivery of the modified interposition device.

Augmentation and interposition devices, modified for advantageous suture-based delivery techniques described herein may, in certain embodiments, be formed as comprising PHAs, and more specifically poly-4-hydroxybutyrate and copolymers thereof, which are absorbable, and to methods for making and delivering such devices for the repair of rotator cuff tears and other tendon or ligament repairs, have been developed. In one embodiment, the devices comprise PHA fibers that provide high initial strength and prolonged strength retention when implanted in vivo, and may incorporate other PHA components, such as PHA non-woven textiles, or other materials that are biocompatible. These devices should be at least partly porous, ideally with pore sizes of at least 10 microns, and be suitable to encourage tissue in-growth.

The modified augmentation and interposition devices should degrade over time following implantation, and improve the long-term outcome of rotator cuff repair. Preferably the devices degrade to non-inflammatory metabolites that are already present in the body. The devices may be replaced by new tissue as they are remodeled in vivo. During the early stages of the remodeling process it is desirable for the devices to retain sufficient strength to provide an effective repair. While desiring not to be bound by theory, it is believed that the augmentation and interposition devices may permit a patient to undergo more aggressive rehabilitation than would have been possible without the use of the devices, for example, when compared to a primary suture repair alone.

The various embodiments of the modified augmentation and interposition devices have many common characteristics, those of ordinary skill will appreciate that the size and shape of the devices will be dependent upon the particular tendon or ligament being repaired, the type of surgical procedure used, size of the defect to be repaired, or of the repair to be augmented. The modified augmentation and interposition devices may be approximately the same size as the defect, but may also be larger or smaller. Alternatively, the augmentation and interposition device may be cut, trimmed or tailored by the surgeon to fit the defect in such a way as to not comprise the functionality of the device.

As a result, in one advantageous aspect, the suture patches described herein are configured to be incorporated directly and effortlessly into the surgical workflow that already includes the use of anchored sutures for suture repair. The surgical and patch delivery methods described above in FIGS. 68-74 may also be modified to include additional or optional steps from other described methods or conventional surgical techniques appropriate to suture-based surgical repairs. For example, the suturing construct with splice tails as illustrated and described in U.S. Pat. No. 8,834,521 FIGS. 1A-1D and FIGS. 7-12 can be modified as described herein to add one or more embodiments of a suture guided patch. In yet another variation, the various double row construct techniques described in US Patent Publication 2010/0249834 FIGS. 2-4 can be modified as described herein to add one or more embodiments of a suture guided patch. In still additional aspects, the various suture guided patches and techniques described herein may also be incorporated into the surgical workflow that includes other fasteners or retainers such as described in U.S. Patent Application Publication 2003/0130694. By way of example and not limitation, the use of additional patches of different size or shape, methods and sequence for securing patches, selection an order of the delivery of patches depending upon the desired type, ratio or amount of a designed release of patch delivered materials and other variations depending upon a number of factors including patient specific needs surgical protocols, indications for use in surgeon preference.

Additionally or optionally, through the use of the modified augmentation and interposition devices described above, suture-based surgical workflows may now incorporate suture guide patches alone or in combination with one or both of the modified augmentation devices or interposition devices described above.

As is appreciated by the details provided herein, the various patch embodiments can be manufactured to permit delivery into the joint through small diameter cannulas utilizing an embodiment of the delivery tool described herein while observing through an arthroscope. In these cases, the patches must be flexible, and of a size and shape that permits them to be deployed through a cannula. Prior to delivery, the patches may be compressed, folded, stretched or otherwise placed under tension and stowed appropriately on a suture guided delivery tool. If desired, the suture guided delivery tool may comprise shape memory materials that cause the tool to open or expand after passing through the cannula while traversing along the suture. For example, in an embodiment of the hollow leg delivery tool, the hollow legs may comprise shape memory joints that cause the legs of the device devices to spring open upon after passage through the cannula. These memory materials may be made from a PHA material, another absorbable material, or from a permanent material such as nitinol.

Additionally or alternatively, additional various details for strength or reinforcing materials, porous materials, compositions, construction, patch delivered materials are provided in: U.S. Pat. Nos. 8,016,883; 8,361,113, 6,080,192; 7,082,337; 7,357,810; 8,876,864; 8,231,653, 8,277,458, 6,514,274, United States Patent Application Publication US 2007/0123984; United States Patent Application Publication 2008/0027470; United States Patent Application Publication 2013/0066370; United States Patent Application Publication 2014/0277449; United States Patent Application Publication 2011/0091515, United States Patent Application Publication 2012/0265219, each of which is incorporated herein by reference in its entirety.

Additionally or alternatively a patch or layer or overall design or construction of a patch may include aspects of the scaffold and other details of the use of one or more of or a plurality of directionally oriented bioresobable polymer films according to the various embodiments described in U.S. Pat. No. 8,226,715. In one aspect directional orientation is aligned with the axis of the suture, a major axis of the patch, a minor axis of the patch or at an angle with respect to one of the above.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A surgical patch to promote healing at a surgical repair site, comprising:
 a patch having a proximal end, a distal end, a right side, a left side wherein the patch has a length between the proximal end and the distal end greater than a width between the right side and the left side, wherein the patch comprises:
  an upper layer,
  a plurality of intermediary layers, comprising:
   a first strength material layer extending along the length of the patch from the proximal end to the distal end, a first porous material layer extending along the length of the patch from the proximal end to the distal end,
a second strength material layer extending along the length of the patch from the proximal end to the distal end,
a second porous material layer extending along the length of the patch from the proximal end to the distal end, and
a lower layer; and
a suture conduit having a proximal end opening in the proximal end of the patch and a distal end opening in the distal end of the patch, the suture conduit extending completely through the patch along the length of the patch from the proximal end opening to the distal end opening, wherein the suture conduit is spaced apart from the left side and the right side of the patch, wherein the first strength material layer is positioned between the suture conduit and the right side of the patch and the second strength material layer is positioned between the suture conduit and the left side of the patch.

2. The surgical patch of claim 1, wherein the first porous material layer is positioned between the first strength material layer and the right side of the patch and wherein the second porous material is positioned between the second strength material layer and the left side of the patch.

3. The surgical patch of claim 1, wherein a width of each of the first strength material layer and the second strength material layer is less than a spacing between the suture conduit and the left side of the patch or the suture conduit and the right side of the patch.

4. The surgical patch of claim 1, wherein a width of each of the first porous material layer and the second porous material layer is less than a spacing between the suture conduit and the left side of the patch or the suture conduit and the right side of the patch.

5. The surgical patch of claim 1, wherein a width of each of the first support material layer and the second support material layer are about the same as a width from the left side of the patch to the right side of the patch.

6. The surgical patch of claim 1, wherein a width of each of the first porous material layer and the second porous material layer is about the same as a width from the left side of the patch to the right side of the patch.

7. The surgical patch of claim 1, wherein a width of the proximal end between the right side of the patch and the left side of the patch is the same as a width of the distal end between the right side of the patch and the left side of the patch.

8. The surgical patch of claim 1, the suture conduit further comprising: a suture conduit width sized to permit sliding passage of a suture through the suture conduit.

9. The surgical patch of claim 1, wherein the suture conduit is closer to the right side of the patch than to the left side of the patch.

10. The surgical patch of claim 1, wherein when the surgical patch is positioned to promote healing at the surgical repair site, a suture disposed within the suture conduit extends along the length of the patch beyond the patch proximal end and beyond the patch distal end.

11. The surgical patch of claim 1, wherein the suture conduit is a continuous suture conduit from the patch proximal end to the patch distal end.

12. The surgical patch of claim 1, the suture conduit further comprising a removeable suture guide structure within the suture conduit.

13. The surgical patch of claim 1, wherein the first strength material layer and the second strength material layer are made from materials that are bioabsorbable.

14. The surgical patch of claim 1, wherein the first porous material layer and the second porous material layer are bioabsorbable.

15. The surgical patch of claim 1, wherein the patch contains a human dermis material selected for use at the suture surgical repair site.

16. The surgical patch of claim 1, wherein the patch contains an autograft material, an allograft material, or a xenograft material selected for use at the surgical repair site.

17. The surgical patch of claim 1, wherein the length of the patch is a pre-set length selected from 1.5 cm, 2.0 cm and 2.5 cm.

18. The surgical patch of claim 1, wherein the width of the patch between the left side and the right side is selected to accommodate a surgical site suture anchor spacing from 0.8 cm to 1.5 cm.

19. The surgical patch of claim 1, wherein the first porous material layer or the second porous material layer contains a human dermis material selected for use at the surgical repair site.

20. The surgical patch of claim 1, wherein the first porous material layer or the second porous material layer contains a patch delivered material.

21. The surgical patch of claim 20, wherein the patch delivered material is any of a therapeutic agent, a diagnostic agent, or a prophylactic agent maintained within a portion of the first porous material layer or a portion of the second porous material layer as a liquid, a powder, a gel, a foam, a particulate media, a solid, a suspended solid, an engineered particle or a nanoparticle.

22. The surgical patch of claim 21, wherein the patch delivered material is a nanoparticle or the engineered particle, wherein the nanoparticle or engineered particle is selected from the group consisting of polymeric nanoparticles, metal nanoparticles, gold nanoparticles, PEG coated nanoparticles, liposomes, micelles, quantum dots, dendrimers, and nanoassemblies.

23. The surgical patch of device of claim 20, wherein the patch delivered material is selected to promote a desired interaction including stimulating tissue in-growth, promoting tissue regeneration, preventing adhesion formation, or preventing infection at the surgical site.

24. The surgical patch of claim 1, wherein the first strength material layer and the first porous material layer or the second strength material layer and the second porous material layer are a biodegradable material layered to form a hybrid structure to contain a patch delivered material with structural support strength.

25. The surgical patch device of claim 1, wherein the first porous material layer and the second porous material layer are formed from a PLA mesh or a PGA mesh and the first strength material layer and the second strength material layer are formed from a PLA strip or a PGA strip arranged to provide structural support of the surgical patch.

* * * * *